US007294616B2

(12) United States Patent
Lyssikatos et al.

(10) Patent No.: US 7,294,616 B2
(45) Date of Patent: Nov. 13, 2007

(54) CAPREOMYCIN DERIVATIVES AND THEIR USE AS ANTIBACTERIALS

(75) Inventors: Joseph P. Lyssikatos, Superior, CO (US); Steven Mark Wenglowsky, Boulder, CO (US)

(73) Assignee: Array BioPharma, Inc., Boulder, CO (US)

( * ) Notice: Subject to any disclaimer, the term of this patent is extended or adjusted under 35 U.S.C. 154(b) by 0 days.

(21) Appl. No.: 11/261,717

(22) Filed: Oct. 31, 2005

(65) Prior Publication Data

US 2006/0094644 A1    May 4, 2006

Related U.S. Application Data

(60) Provisional application No. 60/624,183, filed on Nov. 3, 2004.

(51) Int. Cl.
*A61K 38/12* (2006.01)
(52) U.S. Cl. .......................................... 514/11; 530/317
(58) Field of Classification Search .................... None
See application file for complete search history.

(56) References Cited

OTHER PUBLICATIONS

Dirlam, et al., Bioorganic and Medicinal Chemistry Letters, 1997, 7(9), 1139-1144.*
R.G. Linde II, "Cyclic Homopentapeptides 3. Synthetic Modifications to the Capreomycins and Tuberactinomycins: Compounds with Activity Against Methicillin-Resistant Staphylococcus Aureus And Vancomycin-Resistant Enterococci" Bioorganic & Medical Chemistry Letters, vol. 7, Oxford, GB, 1997.
J.P. Dirlam, "Cyclic Homopentapeptides 1. Analogs of Tuberactinomycins and Capreomycin with Activity Against Vancomycin-Resistant Enterococci and Pasteurella", Bioorganic & Medical Chemistry Letters, vol. 7, Oxford, GB, 1997.
Mu Wang, Steven J. Gould, "Biosynthesis of Capreomycin. 2. Incorporation of L-Serine, L-Alanine, and L-2,3-Diaminopropionic Acid" Journal of Organic Chemistry, vol. 58, 1993, pp. 5176-5180.
Steven J. Gould, "Biosynthesis of Capreomycin. 1. Incorporation of Arginine" Journal of Organic Chemistry, vol. 57, 1992, pp. 5214-5217.
International Preliminary Report On Patentability, date of mailing: May 18, 2007, (10 pages).

* cited by examiner

*Primary Examiner*—Anish Gupta
*Assistant Examiner*—Satyanarayana R. Gudibande
(74) *Attorney, Agent, or Firm*—John R. Moore

(57) ABSTRACT

The present subject matter relates to phenylurea capreomycin derivatives, and to metabolites and pharmaceutically acceptable salts and solvates thereof. The compounds of the present subject matter are useful as antibacterial agents for treating bacterial infections and for treating disorders caused by bacterial infections. The present subject matter also relates to pharmaceutical compositions containing such compounds and to methods of treating bacterial infections by administering such compounds. The present subject matter also relates to methods of preparing such compounds.

44 Claims, No Drawings

CAPREOMYCIN DERIVATIVES AND THEIR USE AS ANTIBACTERIALS

CROSS-REFERENCE TO RELATED APPLICATION

This application claims priority to U.S. Provisional Application Ser. No. 60/624,183, entitled "CAPREOMYCIN DERIVATIVES AND THEIR USE AS ANTIBACTERIALS" filed Nov. 3, 2004, which is incorporated herein by reference in its entirety.

TECHNICAL FIELD

The present subject matter provides phenylurea analogs of capreomycin and compositions comprising said analogs, which are useful as antibacterial agents for treating infections caused by Gram-positive or Gram-negative pathogens. The present subject matter also provides methods of treating bacterial infections.

BACKGROUND

Bacterial pathogens usually fall in one of two groups: Gram-positive or Gram-negative. Antibacterial agents (including antibiotics) often exhibit selective activity for either Gram-positive or Gram-negative pathogens. Antibacterial agents that target both classes of pathogens are regarded as having broad spectrum activity.

There are many known classes of antibacterial agents such as the penicillins and cephalosporins, tetracyclines, sulfonamides, monobactams, fluoroquinolones and quinolones, glycopeptides, aminoglycosides, polymixins, macrolides, lincosamides, trimethoprim and chloramphenicol. The mechanisms of action of these various classes of antibacterial agents vary.

Resistant strains have evolved/arisen among Gram-positive pathogens such as *Staphylococci, Streptococci, Mycobacteria* and *Enterococci*, making the eradication of these strains very difficult. Examples of such strains include methicillin-resistant *Staphylococcus aureus* (MRSA), methicillin-resistant coagulase negative *Staphylococci* (MRCNS), penicillin-resistant *Streptococcus pneumoniae* and multiply-resistant *Enterococcus faecium*.

Resistance to aminoglycosides, β-lactams (penicillins and cephalosporins) and chloramphenicol analogs is often expressed in pathogenic bacteria. This type of resistance is due to the bacteria-mediated modification of the antibacterial agent through either cleavage of the drug (as in the case with β-lactams) or formation of inactive derivatives (as in the case with aminoglycosides). As for the β-lactams, the resistance observed in clinical isolates is most commonly a result of the expression of "penicillinase" (a β-lactamase) that hydrolytically cleaves the β-lactam ring, thereby inactivating the antibacterial agent.

A more recent threat is the emergence of vancomycin-resistant (VRE) strains of enterococci (Woodford N., 1998, *J. Medical Microbiology*, 47(10):849-62). VRE strains are frequent causes of hospital-acquired infections and are unfortunately inherently resistant to most antibiotics. Vancomycin inhibits bacterial cell wall synthesis by binding to the terminal D-Ala-D-Ala residues of the cell wall peptidoglycan precursor. The high level vancomycin resistance of VRE isolates is termed VanA and is mediated by genes located on a transposable element which changes the terminal D-Ala-D-Ala residues to D-Ala-D-lac, thereby reducing the affinity for vancomycin.

Capreomycin is a cyclic homopentapeptide obtained from fermentation of *Streptomyces caprolus* (Herr, E. B., Jr., et al., 1960, *Proc. Ind. Acad. Sci.*, 69:134) and is produced as a four-component mixture, with capreomycin IA and IB present as major products, and IIA and IIB as minor ones. Capreomycin has potent activity against mycobacteria, with little activity against other genera of bacteria.

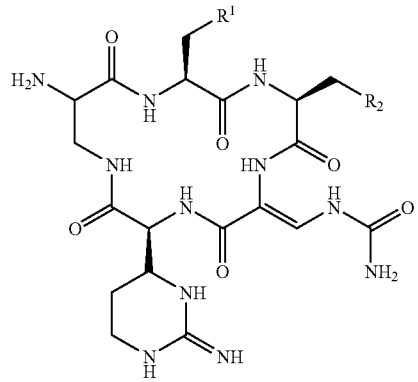

Capreomycin IA: $R^1$=OH, $R^2$=β-(S)-lysine amide
Capreomycin IB: $R^1$=H, $R^2$=β-(S)-lysine amide
Capreomycin IIA: $R^1$=OH, $R^2$=$NH_2$
Capreomycin IIB: $R^1$=H, $R^2$=$NH_2$ Capreomycin itself is used clinically as a second-line treatment for tuberculosis but is not efficacious against most Gram-positive bacteria (as in the case with *Staphylococcus*) or Gram-negative bacteria (as in the case with *Escherichia coli*). Certain alkyl-, cycloalkyl- and halogen-substituted phenylurea analogs of capreomycin have been demonstrated to be broad-spectrum (Gram-negative and Gram-positive) antibacterials, especially against resistant strains (Dirlam, et al., *Bioorganic and Medicinal Chemistry Letters*, 1997, 7(9), 1149-1152).

In light of the rapid emergence of multidrug-resistant bacterial pathogens, the development of antibacterial agents that are effective against both Gram-positive and Gram-negatives pathogens, irrespective of their resistance profiles, and particularly against VRE and MRSA, is urgently needed.

SUMMARY

The present subject matter relates to phenylurea analogs of capreomycin and the use thereof in the treatment of microbial infections in a mammal. More specifically, the present subject matter relates to compounds of the general Formula I

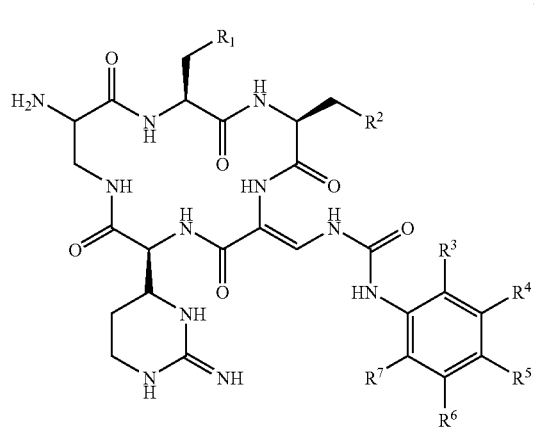

and solvates, metabolites, and pharmaceutically acceptable salts and prodrugs thereof, wherein:

R¹ is OH or H;

R² is NH₂ or

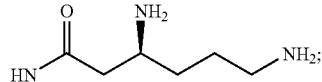

R³, R⁴, R⁵, R⁶ and R⁷ are independently selected from aryl, heteroaryl, X-aryl, X-heteroaryl, hydrogen, halogen, cyano, nitro, trifluoromethyl, difluoromethyl, fluoromethyl, fluoromethoxy, difluoromethoxy, trifluoromethoxy, azido, —OR⁸, SR⁸, —C(O)R⁸, —C(O)OR⁸, NR⁹C(O)OR¹³, —OC(O)R⁸, —NR⁹SO₂R¹³, —SO₂NR⁸R⁹, —NR⁹C(O)R⁸, —C(O)NR⁸R⁹, —NR¹⁰C(O)NR⁸R⁹, —NR¹⁰C(NCN)NR⁸R⁹, —NR⁸R⁹, alkyl, alkenyl, alkynyl, cycloalkyl, cycloalkylalkyl, —S(O)ⱼ(alkyl), —S(O)ⱼ(CR¹¹R¹²)ₘ-aryl, arylalkyl, heteroarylalkyl, heterocyclyl, heterocyclylalkyl, —O(CR¹¹R¹²)ₙ-heterocyclyl or —NR⁹(CR¹¹R¹²)ₙ-heterocyclyl, wherein at least one of R³, R⁴, R⁵, R⁶ and R⁷ is aryl, heteroaryl, X-aryl or X-heteroaryl, and wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, oxime, halogen, cyano, nitro, fluoromethyl, difluoromethyl, trifluoromethyl, fluoromethoxy, difluoromethoxy, trifluoromethoxy, azido, alkyl, alkenyl, alkynyl, cycloalkyl, cycloalkylalkyl, —OR⁸, —C=NOR⁸, —C(O)R⁸, —C(O)OR⁸, —OC(O)R⁸, —C(O)NR⁸R⁹, —NR⁸R⁹, —NR⁹C(O)OR¹³, —NR⁹C(O)R⁸, —NR¹⁰C(O)NR⁸R⁹, —NR¹⁰C(NCN)NR⁸R⁹, —O(CR¹¹R¹²)ₙ-aryl, —NR⁹(CR¹¹R¹²)ₘ-aryl, —O(CR¹¹R¹²)ₙ-heteroaryl, —NR⁹(CR¹¹R¹²)ₘ-heteroaryl, —O(CR¹¹R¹²)ₙ-heterocyclyl, —NR₉(CR¹¹R¹²)ₙ-heterocyclyl, —S(O)ⱼ(alkyl), —S(O)ⱼ(CR¹¹R¹²)ₘ-aryl, —SO₂NR⁸R⁹, —NR⁹SO₂R¹³, aryl, heteroaryl, arylalkyl, heteroarylalkyl, heterocyclyl and heterocyclylalkyl;

X is O, O(CR¹¹R¹²)ₙ, NR⁹, (CR¹¹R¹²)ₙ, CR¹¹=CR¹², or S(O)ⱼ(CR¹¹R¹²)ₘ, with the proviso that when R⁵ is CH₂-phenyl, then R³, R⁴, R⁶ and R⁷ are not hydrogen;

R⁸ is hydrogen, trifluoromethyl, alkyl, alkenyl, alkynyl, cycloalkyl, cycloalkylalkyl, aryl, arylalkyl, heteroaryl, heteroarylalkyl, heterocyclyl, heterocyclylalkyl, phosphate, or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR'SO₂R'''', —SO₂NR'R'', —C(O)R', C(O)OR', —OC(O)R', —NR'C(O)OR'''', —NR'C(O)R'', —C(O)NR'R'', —SR', —S(O)R'''', —SO₂R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl;

R⁹, R¹⁰, R¹¹ and R¹² are independently hydrogen or alkyl, and

R¹³ is trifluoromethyl, alkyl, cycloalkyl, aryl, arylalkyl, heteroaryl, heteroarylalkyl, heterocyclyl, heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR'SO₂R'''', —SO₂NR'R'', —C(O)R', —C(O)OR', —OC(O)R', —NR'C(O)OR'''', —NR'C(O)R'', —C(O)NR'R'', —SO₂R'''', —NR'R'', —NR'C(O)NR''R''', —NR'C(NCN)NR''R''', —OR, aryl, heteroaryl, arylalkyl, heteroarylalkyl, heterocyclyl, and heterocyclylalkyl, or R⁸ and R⁹ together with the atoms to which they are attached form a 4 to 10 membered saturated, partially unsaturated, or fully unsaturated heterocyclic ring, wherein said heterocyclic ring is optionally substituted with one or more groups independently selected from halogen, cyano, nitro, trifluoromethyl, difluoromethoxy, trifluoromethoxy, azido, —NR'SO₂R'''', —SO₂NR'R'', —C(O)R'''', —C(O)OR', —OC(O)R', —NR'C(O)OR'''', —NR'C(O)R'', —C(O)NR'R'', —SO₂R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or R⁹ and R¹⁰ together with the atoms to which they are attached form a 4 to 10 membered saturated, partially unsaturated, or fully unsaturated heterocyclic ring, wherein said heterocyclic ring is optionally substituted with one or more groups independently selected from halogen, cyano, nitro, trifluoromethyl, difluoromethoxy, trifluoromethoxy, azido, —NR'SO₂R'''', —SO₂NR'R'', —C(O)R'''', —C(O)OR', —OC(O)R', —NR'C(O)OR'''', —NR'C(O)R'', —C(O)NR'R'', —SO₂R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or R⁹ and R¹¹ together with the atoms to which they are attached form a 4 to 10 membered saturated, partially unsaturated, or fully unsaturated heterocyclic ring, wherein said heterocyclic ring is optionally substituted with one or more groups independently selected from halogen, cyano, nitro, trifluoromethyl, difluoromethoxy, trifluoromethoxy, azido, —NR'SO₂R'''', —SO₂NR'R'', —C(O)R'''', —C(O)OR', —OC(O)R', —NR'C(O)OR'''', —NR'C(O)R'', —C(O)NR'R'', —SO₂R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or R⁹ and R¹³ together with the atoms to which they are attached form a 4 to 10 membered saturated, partially unsaturated, or fully unsaturated heterocyclic ring, wherein said heterocyclic ring is optionally substituted with one or more groups independently selected from halogen, cyano, nitro, trifluoromethyl, difluoromethoxy, trifluoromethoxy, azido, —NR'SO₂R'''', —SO₂NR'R'', —C(O)R'''', —C(O)OR', —OC(O)R', —NR'C(O)OR'''', —NR'C(O)R'', —C(O)NR'R'', —SO₂R'''', —NR'R'', —NR'C(O)NR''R''', —NR'C(NCN)NR''R''', —OR, aryl, heteroaryl, arylalkyl, heteroarylalkyl, heterocyclyl, and heterocyclylalkyl, or R¹¹ and R¹² together with the atoms to which they are attached form a 4 to 10 membered saturated, partially unsaturated, or fully unsaturated carbocyclic ring, wherein said carbocyclic ring is optionally substituted with one or more groups independently selected from halogen, cyano, nitro, trifluoromethyl, difluoromethoxy, trifluoromethoxy, azido, —NR'SO₂R'''', —SO₂NR'R'', —C(O)R'''', —C(O)OR', —OC(O)R', —NR'C(O)OR'''', —NR'C(O)R'', —C(O)NR'R'', —SO₂R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl;

R', R'' and R''' independently are hydrogen, alkyl, alkenyl, aryl and arylalkyl, and R'''' is alkyl, alkenyl, aryl and arylalkyl, or any two of R', R'', R''' or R'''' together with the atoms to which they are attached form a 4 to 10 membered carbocyclic, aryl, heteroaryl or heterocyclic ring, wherein any of said alkyl, alkenyl, and arylalkyl, and any of said carbocyclic, aryl, heteroaryl and heterocyclic rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

m is 0, 1, 2, 3, 4 or 5;
n is 1, 2, 3, 4 or 5; and
j is 0, 1 or 2.

Another aspect of the present subject matter provides compositions comprising one or more compounds of Formula I.

Another aspect of the present subject matter provides methods of preventing or treating a bacterial infection in a mammal, comprising administering to said mammal in need of such treatment an effective amount of a compound of Formula I or a solvate, metabolite, or pharmaceutically acceptable salt or prodrug thereof.

Another aspect of the present subject matter provides methods of preventing or treating disorders related to bacterial infections, comprising administering to a mammal in need of such treatment an effective amount of a compound of Formula I or a solvate, metabolite, or pharmaceutically acceptable salt or prodrug thereof.

Bacterial infections which may be treated or prevented in mammals according to the methods of the present subject matter include, but are not limited to, hospital acquired (nosocomial) infections, pneumonia, otitis media, sinusitis, bronchitis, tonsillitis, mastoiditis, pharyngitis, rheumatic fever, glomerulonephritis, respiratory tract infections, blood and tissue infections such as edocarditis and osteomyelitis, uncomplicated skin and soft tissue infections and abscesses, complicated skin and skin structure infections, puerperal fever, uncomplicated acute urinary tract infections, complicated urinary tract infections, urethritis, cervicitis, sexually transmitted diseases, toxin diseases such as food poisoning and toxic shock syndrome, ulcers, systemic febrile syndromes, Lyme disease, conjunctivitis, keratitis, dacrocystitis, gastroenteritis, antibiotic-associated diarrhea, colitis, pseudomembraneous colitis, odontogenic infection, persistent cough, gas gangrene, atherosclerosis and cardiovascular disease.

Additional disorders related to bacterial infections which may be treated or prevented in mammals according to the methods of the present subject matter include bovine respiratory disease, dairy cow mastitis, swine respiratory disease, swine enteric disease, cow foot-rot, cow hairy warts, cow pink eye, skin and soft tissue infections in dogs and cats, and dental and mouth infections in dogs and cats.

Another aspect of the present subject matter includes methods of preparing compounds of Formula I.

Another aspect of the present subject matter includes kits comprising a compound of Formula I or a solvate, metabolite, or pharmaceutically acceptable salt or prodrug thereof, and optionally a package insert or label indicating a treatment.

Additional advantages and novel features of the present subject matter shall be set forth in part in the description that follows, and in part will become apparent to those skilled in the art upon examination of the following specification or may be learned by the practice of the present subject matter. The advantages of the present subject matter may be realized and attained by means of the instrumentalities, combinations, compositions, and methods particularly pointed out in the appended claims.

DETAILED DESCRIPTION

The present subject matter provides compounds that exhibit potent broad spectrum activity against both Gram-positive microbes such as, but not limited to, *Staphylococcus aureus, Staphylococcus haemolyticus, Enterococcus faecalis, Enterococcus faecium*, and *Streptococcus pneumoniae*, and Gram-negative microbes such as, but not limited to, *Pseudonomas aeruginosa, Klebsiella pneumoniae, Escherichia coli, Haemophilus influenzae, Citrobacter freundii* and *Enterobacter* spp.

The compounds of the present subject matter are especially noteworthy because of their excellent activity against resistant and multi-resistant strains such as MRSA, VISA, vancomycin-resistant *Enterococcus faecium*, Linezolid-resistant MRSA, Gentamycin-resistant *Enterococcus faecalis*, PVL positive MRSA, Synercid-resistant *Streptococcus pneumoniae, Escherichia coli* resistant to both beta-lactams and fluoroquinolones, multi-resistant (beta-lactams, fluoroquinolines, tetracycline, nitrofurantoin) *Citrobacter freundii*, multi-resistant *Enterobacter* spp., beta-lactam and aminoglycoside-resistant *Klebsiella pneumoniae* and multi-resistant (fluoroquinolone, tetracycline, trimethoprim, sulphamethoxazole, augmentin, nitrofurantoin, gentamycin, amikamycin, cefuroxime and impenem) *Psuedonomas aeruginosa*.

More specifically, the present subject matter relates to compounds of the general Formula I

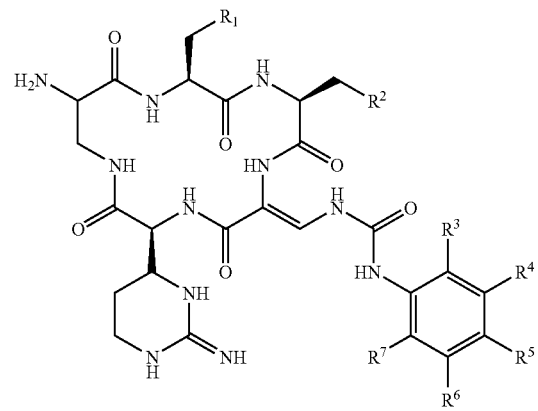

I and solvates, metabolites, and pharmaceutically acceptable salts and prodrugs thereof, wherein:

$R^1$ is OH or H;
$R^2$ is $NH_2$ or;

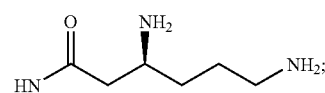

$R^3$, $R^4$, $R^5$, $R^6$ and $R^7$ are independently selected from aryl, heteroaryl, X-aryl, X-heteroaryl, hydrogen, halogen, cyano, nitro, trifluoromethyl, difluoromethyl, fluoromethyl, fluoromethoxy, difluoromethoxy, trifluoromethoxy, azido, —$OR^8$, $SR^8$, —$C(O)R^8$, —$C(O)OR^8$, $NR^9C(O)OR^{13}$, —$OC(O)R^8$, —$NR^9SO_2R^{13}$, —$SO_2NR^8R^9$, —$NR^9C(O)R^8$, —$C(O)NR^8R^9$, —$NR^{10}C(O)NR^8R^9$, —$NR^{10}C(NCN)NR^8R^9$, —$NR^8R^9$, alkyl, alkenyl, alkynyl, cycloalkyl, cycloalkylalkyl, —$S(O)_j(alkyl)$, —$S(O)_j(CR^{11}R^{12})_m$-aryl, arylalkyl, heteroarylalkyl, heterocyclyl, heterocyclylalkyl, —$O(CR^{11}R^{12})_n$-heterocyclyl or —$NR^9(CR^{11}R^{12})_n$-heterocyclyl, wherein at least one of $R^3$, $R^4$, $R^5$, $R^6$ and $R^7$ is aryl, heteroaryl, X-aryl or X-heteroaryl, and wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, oxime, halogen, cyano, nitro, fluoromethyl, difluoromethyl, trifluoromethyl, fluoromethoxy, difluoromethoxy, trifluoromethoxy, azido, alkyl, alkenyl, alkynyl, cycloalkyl, cycloalkylalkyl, —$OR^8$, —C=$NOR^8$, —C(O)$R^8$, —C(O)$OR^8$, —OC(O)$R^8$, —C(O)$NR^8R^9$, —$NR^8R^9$, —$NR^9$C(O)$OR^{13}$, —$NR^9$C(O)$R^8$, —$NR^{10}$C(O)$NR^8R^9$, —$NR^{10}$C(NCN)$NR^8R^9$, —O($CR^{11}R^{12}$)$_n$-aryl, —$NR^9$($CR^{11}R^{12}$)$_m$-aryl, —O($CR^{11}R^{12}$)$_n$-heteroaryl, —$NR^9$($CR^{11}R^{12}$)$_m$-heteroaryl, —O($CR^{11}R^{12}$)$_n$-heterocyclyl, —$NR^9$($CR^{11}R^{12}$)$_n$-heterocyclyl, —S(O)$_j$(alkyl), —S(O)$_j$($CR^{11}R^{12}$)$_m$-aryl, —$SO_2NR^8R^9$, —$NR^9SO_2R^{13}$, aryl, heteroaryl, arylalky heteroarylalkyl, heterocyclyl and heterocyclylalkyl;

X is O, O($CR^{11}R^{12}$)$_n$, $NR^9$, ($CR^{11}R^{12}$)$_n$, $CR^{11}$=$CR^{12}$, or S(O)$_j$($CR^{11}R^{12}$)$_m$, with the proviso that when $R^5$ is $CH_2$-phenyl, then $R^3$, $R^4$, $R^6$ and $R^7$ are not hydrogen;

$R^8$ is hydrogen, trifluoromethyl, alkyl, alkenyl, alkynyl, cycloalkyl, cycloalkylalkyl, aryl, arylalkyl, heteroaryl, heteroarylalkyl, heterocyclyl, heterocyclylalkyl, phosphate, or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR'$SO_2$R'''', —$SO_2$NR'R'', —C(O)R', C(O)OR', —OC(O)R', —NR'C(O)OR'''', —NR'C(O)R'', —C(O)NR'R'', —SR', —S(O)R'''', —$SO_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl;

$R^9$, $R^{10}$, $R^{11}$ and $R^{12}$ are independently hydrogen or alkyl, and $R^{13}$ is trifluoromethyl, alkyl, cycloalkyl, aryl, arylalkyl, heteroaryl, heteroarylalkyl, heterocyclyl, heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR'$SO_2$R'''', —$SO_2$NR'R'', —C(O)R', —C(O)OR', —OC(O)R', —NR'C(O)OR'''', —NR'C(O)R'', —C(O)NR'R'', —$SO_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or $R^8$ and $R^9$ together with the atoms to which they are attached form a 4 to 10 membered saturated, partially unsaturated, or fully unsaturated heterocyclic ring, wherein said heterocyclic ring is optionally substituted with one or more groups independently selected from halogen, cyano, nitro, trifluoromethyl, difluoromethoxy, trifluoromethoxy, azido, —NR'$SO_2$R'''', —$SO_2$NR'R'', —C(O)R'''', —C(O)OR', —OC(O)R', —NR'C(O)OR'''', —NR'C(O)R'', —C(O)NR'R'', —$SO_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or $R^9$ and $R^{10}$ together with the atoms to which they are attached form a 4 to 10 membered saturated, partially unsaturated, or fully unsaturated heterocyclic ring, wherein said heterocyclic ring is optionally substituted with one or more groups independently selected from halogen, cyano, nitro, trifluoromethyl, difluoromethoxy, trifluoromethoxy, azido, —NR'$SO_2$R'''', —$SO_2$NR'R'', —C(O)R'''', —C(O)OR', —OC(O)R', —NR'C(O)OR'''', —NR'C(O)R'', —C(O)NR'R'', —$SO_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or $R^9$ and $R^{11}$ together with the atoms to which they are attached form a 4 to 10 membered saturated, partially unsaturated, or fully unsaturated heterocyclic ring, wherein said heterocyclic ring is optionally substituted with one or more groups independently selected from halogen, cyano, nitro, trifluoromethyl, difluoromethoxy, trifluoromethoxy, azido, —NR'$SO_2$R'''', —$SO_2$NR'R'', —C(O)R'''', —C(O)OR', —OC(O)R', —NR'C(O)OR'''', —NR'C(O)R'', —C(O)NR'R'', —$SO_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or $R^9$ and $R^{13}$ together with the atoms to which they are attached form a 4 to 10 membered saturated, partially unsaturated, or fully unsaturated heterocyclic ring, wherein said heterocyclic ring is optionally substituted with one or more groups independently selected from halogen, cyano, nitro, trifluoromethyl, difluoromethoxy, trifluoromethoxy, azido, —NR'$SO_2$R'''', —$SO_2$NR'R'', —C(O)R'''', —C(O)OR', —OC(O)R', —NR'C(O)OR'''', —NR'C(O)R'', —C(O)NR'R'', —$SO_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or $R^{11}$ and $R^{12}$ together with the atoms to which they are attached form a 4 to 10 membered saturated, partially unsaturated, or fully unsaturated carbocyclic ring, wherein said carbocyclic ring is optionally substituted with one or more groups independently selected from halogen, cyano, nitro, trifluoromethyl, difluoromethoxy, trifluoromethoxy, azido, —NR'$SO_2$R'''', —$SO_2$NR'R'', —C(O)R'''', —C(O)OR', —OC(O)R', —NR'C(O)OR'''', —NR'C(O)R'', —C(O)NR'R'', —$SO_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl;

R', R'' and R''' independently are hydrogen, alkyl, alkenyl, aryl and arylalkyl, and R'''' is alkyl, alkenyl, aryl and arylalkyl, or any two of R', R'', R''' or R'''' together with the atoms to which they are attached form a 4 to 10 membered carbocyclic, aryl, heteroaryl or heterocyclic ring, wherein any of said alkyl, alkenyl, and arylalkyl, and any of said carbocyclic, aryl, heteroaryl and heterocyclic rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

m is 0, 1, 2, 3, 4 or 5;

n is 1, 2, 3, 4 or 5; and j is 0, 1 or 2.

In certain embodiments, at least one of $R^3$, $R^4$, $R^5$, $R^6$ and $R^7$ is aryl or heteroaryl. Exemplary embodiments include, but are not limited to, phenyl, naphthyl, 2-pyridyl, 3-pyridyl, 4-pyridyl, 2-pyrimidyl, 4-pyrimidyl, 5-pyrimidyl, 1-isoquinolyl, 3-isoquinolyl, 4-isoquinolyl, 2-thienyl, 3-thienyl, 2-benzo[b]thienyl, 3-benzo[b]thienyl, 4-isoxazolyl, and substituted forms thereof. In certain embodiments, $R^3$, $R^4$, $R^5$, $R^6$ and $R^7$ are optionally substituted with one or more groups independently selected from halogen, alkyl, $CF_3$, $OCF_3$, and heteroalkyl. In certain embodiments, $R^3$, $R^4$, $R^5$, $R^6$ and $R^7$ are optionally substituted with one or more groups independently selected from F, Cl, $CF_3$, $CH_3$, $OCH_3$, and $OCF_3$.

In certain embodiments, at least one of $R^3$, $R^4$, $R^5$, $R^6$ and $R^7$ is X-aryl or X-heteroaryl. Exemplary embodiments include, but are not limited to, O-phenyl, S-phenyl, $OCH_2$- phenyl, S—CH₂-phenyl, CH₂-phenyl, CH₂CH₂-phenyl, CH=CH-phenyl, CH₂SO₂-phenyl, and NH-phenyl. In certain embodiment, said phenyl is substituted with one or more groups independently selected from halogen, alkyl, CF₃, OCF₃, and heteroalkyl. In certain embodiments, said phenyl is substituted with one or more groups independently selected from F, Cl, CF₃, CH₃, OCH₃, and OCF₃.

In certain embodiments of compounds of Formula I, R¹ is H and R² is

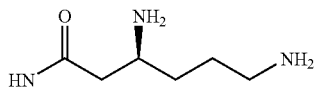

(i.e., β-(S)-lysine amide).

In certain embodiments of compounds of Formula I, R¹ is OH and R² is β-(S)-lysine amide.

Exemplary compounds of Formula I include compounds wherein R¹ is H, R² is β-(S)-lysine amide, R³, R⁵, R⁶ and R⁷ are H, and R⁴ is selected from phenyl, 4-chlorophenyl, 4-trifluoromethylphenyl, 3-trifluoromethylphenyl, 4-tolyl, 4-trifluoromethoxyphenyl, 1-naphthyl, and 2-naphthyl.

Additional exemplary compounds of Formula I include compounds wherein R¹ is H, R² is β-(S)-lysine amide, R³, R⁵, R⁶ and R⁷ are H, and R⁴ is selected from 2-pyridyl, 3-pyridyl, 4-pyridyl, 5-pyrimidyl, 4-isoquinolyl, 2-thienyl, 3-thienyl, 2-chloro-3-thieny, 3-benzo[b]thienyl, 2-benzo[b]thienyl, 3,5-dimethyl-4-isoxazolyl, and phenoxy.

Additional exemplary compounds of Formula I include compounds wherein R¹ is H, R² is β-(S)-lysine amide, R³, R⁴, R⁶ and R⁷ are H, and R⁵ is selected from phenyl, 4-chlorophenyl, 4-trifluoromethylphenyl, 3,5-ditrifluoromethylphenyl, 1-naphthyl, 2-naphthyl, 2-pyridyl, 3-pyridyl, 4-pyridyl, and 2-thienyl.

Additional exemplary compounds of Formula I include compounds wherein R¹ is H, R² is β-(S)-lysine amide, R³, R⁴, R⁶ and R⁷ are H, and R⁵ is selected from phenoxy, 4-chlorophenyoxy, 4-methylphenoxy, 3,5-difluoromethylphenyl, 4-fluorophenoxy, 4-trifluoromethylphenoxy, and 3-trifluoromethylphenoxy.

Additional exemplary compounds of Formula I include compounds wherein R¹ is H, R² is β-(S)-lysine amide, R³, R⁴, R⁶ and R⁷ are H, and R⁵ is selected from benzenethiolate, 4-methylbenzenethiolate, CH₂=CHPh, CH₂CH₂Ph, CH₂SO₂Ph, NHPh, OCH₂Ph and CH₂SPh.

Additional exemplary compounds of Formula I include compounds wherein R¹ is H, R² is β-(S)-lysine amide, R⁴, R⁵, R⁶ and R⁷ are H, and R³ is selected from phenyl, 4-chlorophenyl and phenoxy.

The present subject matter further includes compositions comprising one or more compounds of Formula I. In certain embodiments, the composition comprises compounds of Formula I wherein R³ is aryl, heteroaryl, X-aryl or X-heteroaryl, and R⁴, R⁵, R⁶ and R⁷ are H. In other embodiments, the composition comprises compounds of Formula I wherein R⁴ is aryl, heteroaryl, X-aryl or X-heteroaryl, and R³, R⁵, R⁶ and R⁷ are H. In other embodiments, the composition comprises compounds of Formula I wherein R⁵ is aryl, heteroaryl, X-aryl or X-heteroaryl, and R³, R⁴, R⁶ and R⁷ are H.

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl(Me, —CH₃), ethyl(Et, —CH₂CH₃), 1-propyl(n-Pr, n-propyl, —CH₂CH₂CH₃), 2-propyl(i-Pr, i-propyl, —CH(CH₃)₂), 1-butyl(n-Bu, n-butyl, —CH₂CH₂CH₂CH₃), 2-methyl-1-propyl(i-Bu, i-butyl, —CH₂CH(CH₃)₂), 2-butyl(s-Bu, s-butyl, —CH(CH₃)CH₂CH₃), 2-methyl-2-propyl(t-Bu, t-butyl, —C(CH₃)₃), 1-pentyl(n-pentyl, —CH₂CH₂CH₂CH₂CH₃), 2-pentyl(—CH(CH₃)CH₂CH₂CH₃), 3-pentyl(—CH(CH₂CH₃)₂), 2-methyl-2-butyl(—C(CH₃)₂CH₂CH₃), 3-methyl-2-butyl(—CH(CH₃)CH(CH₃)₂), 3-methyl-1-butyl(—CH₂CH₂CH(CH₃)₂), 2-methyl-1-butyl(—CH₂CH(CH₃)CH₂CH₃), 1-hexyl(—CH₂CH₂CH₂CH₂CH₂CH₃), 2-hexyl(—CH(CH₃)CH₂CH₂CH₂CH₃), 3-hexyl(—CH(CH₂CH₃)(CH₂CH₂CH₃)), 2-methyl-2-pentyl(—C(CH₃)₂CH₂CH₂CH₃), 3-methyl-2-pentyl(—CH(CH₃)CH(CH₃)CH₂CH₃), 4-methyl-2-pentyl(—CH(CH₃)CH₂CH(CH₃)₂), 3-methyl-3-pentyl(—C(CH₃)(CH₂CH₃)₂), 2-methyl-3-pentyl(—CH(CH₂CH₃)CH(CH₃)₂), 2,3-dimethyl-2-butyl(—C(CH₃)₂CH(CH₃)₂), 3,3-dimethyl-2-butyl(—CH(CH₃)C(CH₃)₃, 1-heptyl, 1-octyl, cyclopropyl, cyclobutyl, cyclopentyl, cyclohexyl, cycloheptyl, and cyclooctyl.

The term "alkenyl" refers to linear or branched-chain monovalent hydrocarbon radical of two to twelve carbon atoms with at least one site of unsaturation, i.e., a carbon-carbon, sp² double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=CH₂), allyl(—CH₂CH=CH₂), 1-cyclopent-1-enyl, 1-cyclopent-2-enyl, 1-cyclopent-3-enyl, 5-hexenyl, 1-cyclohex-1-enyl, 1-cyclohex-2-enyl, and 1-cyclohex-3-enyl.

The term "alkynyl" refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl(—C≡CH) and propynyl(propargyl, —CH₂C≡CH).

The term "allyl" refers to a radical having the formula RC=CHCHR, wherein R is alkyl, alkenyl, alkynyl, cycloalkyl, heterocycloalkyl, aryl, or heteroaryl, wherein the allyl may be optionally substituted independently with one or more substituents described herein.

The terms "cycloalkyl," "carbocyclyl," and "carbocycle" are used interchangeably and refer to a monovalent non-aromatic, saturated or partially unsaturated cyclic hydrocarbon radical having from three to ten carbon atoms. Examples of monocyclic carbocyclic radicals include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. The cycloalkyl may be optionally substituted independently in one or more substitutable positions with various groups. The term "cycloalkyl" also includes polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The terms "heterocycloalkyl," "heterocycle" and "heterocyclyl" refer to a saturated or partially unsaturated carbocyclic radical of 3 to 8 ring atoms in which at least one ring atom is a heteroatom selected from nitrogen, oxygen and sulfur, the remaining ring atoms being C, where one or more ring atoms may be optionally substituted independently with one or more substituent described below. The radical may be a carbon radical or heteroatom radical. The term further includes fused ring systems that include a heterocycle fused to an aromatic group. "Heterocycloalkyl" also includes radicals where heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl and quinolizinyl. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring with a fused non-aromatic ring, a partially unsaturated ring, or an aromatic ring. Typical aryl groups include, but are not limited to, radicals derived from benzene, substituted benzenes, naphthalene, anthracene, biphenyl, indenyl, indanyl, 1,2-dihydronapthalene, 1,2,3,4-tetrahydronapthyl, and the like. The aryl groups herein are unsubstituted or, as specified, substituted in one or more substitutable positions with various groups.

"Heteroaryl", "heterocyclyl", and "heterocycle" all refer to a ring system in which one or more ring atoms are a heteroatom, e.g., nitrogen, oxygen, and sulfur. The heterocyclyl radical comprises 1 to 20 carbon atoms and 1 to 6 heteroatoms selected from N, O, P, and S. The heterocyclyl radical may be saturated, partially unsaturated or fully unsaturated. The heterocyclyl radical may be aromatic or non-aromatic. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocyclyl radicals include, but are not limited to, pyridyl, dihydroypyridyl, 4-dialkylaminopyridinium, tetrahydropyridyl(piperidyl), thiazolyl, tetrahydrothiophenyl, sulfur-oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, 3-oxo-tetrahydrofuranyl, 3-oximinio-tetrahydrofuranyl, bis-tetrahydrofuranyl, tetrahydropyranyl, 4-oxo-tetrahydropyranyl, 4-oximino-tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "halogen" represents fluorine, bromine, chlorine, and iodine.

The term "arylalkyl" means an alkyl moiety (as defined above) substituted with one or more aryl moiety (also as defined above). More preferred arylalkyl radicals are aryl-$C_{1-3}$-alkyls. Examples include benzyl, phenylethyl, and the like.

The term "heteroarylalkyl" means an alkyl moiety (as defined above) substituted with a heteroaryl moiety (also as defined above). More preferred heteroarylalkyl radicals are 5- or 6-membered heteroaryl-$C_{1-3}$-alkyls. Examples include oxazolylmethyl, pyridylethyl and the like.

The term "heterocyclylalkyl" means an alkyl moiety (as defined above) substituted with a heterocyclyl moiety (also defined above). More preferred heterocyclylalkyl radicals are 5- or 6-membered heterocyclyl-$C_{1-3}$-alkyls. Examples include tetrahydropyranylmethyl.

The term "cycloalkylalkyl" means an alkyl moiety (as defined above) substituted with a cycloalkyl moiety (also defined above). More preferred heterocyclyl radicals are 5- or 6-membered cycloalkyl-$C_{1-3}$-alkyls. Examples include cyclopropylmethyl.

"Substituted alkyl" refers to an alkyl in which one or more hydrogen atoms are each independently replaced with a substituent. Typical substituents include, but are not limited to, F, Cl, Br, I, CN, $CF_3$, OR, R, =O, =S, =NR, =$N^+$(O)(R), =N(OR), =$N^+$(O)(OR), =N—NRR', —C(=O)R, —C(=O)OR, —C(=O)NRR', —NRR', —$N^+$RR'R", —N(R)C(=O)R', —N(R)C(=O)OR', —N(R)C(=O)NR'R", —SR, —OC(=O)R, —OC(=O)OR, —OC(=O)NRR', —OS(O)$_2$(OR), —OP(=O)(OR)$_2$, —OP(OR)$_2$, —P(=O)(OR)$_2$, —P(=O)(OR)NR'R", —S(O)R, —S(O)$_2$R, —S(O)$_2$NR, —S(O)(OR), —S(O)$_2$(OR), —SC(=O)R, —SC(=O)OR, =O and —SC(=O)NRR'; wherein each R, R' and R" is independently selected from H, $C_1$-$C_{10}$ alkyl, $C_1$-$C_{10}$ alkenyl, $C_1$-$C_{10}$ alkynyl, $C_6$-$C_{20}$ aryl and $C_2$-$C_{20}$ heterocycle. Alkenyl, alkynyl, allyl, cycloalkyl, heteroalkyl, heterocycloalkyl, arylalkyl, heteroarylalkyl, heterocyclylalkyl, cycloalkylalkyl, aryl and heteroaryl groups as described above may also be similarly substituted.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

In the compounds of the present subject matter where a term such as $(CR^{11}R^{12})_m$ is used, $R^{11}$ and $R^{12}$ may vary with each iteration of m above 1. For instance, where m is 2, the term $(CR^{11}R^{12})_m$ may equal —$CH_2CH_2$— or —$CH(CH_3)C(CH_2CH_3)(CH_2CH_2CH_3)$— or any number of similar moieties falling within the scope of the definitions of $R^{11}$ and $R^{12}$.

The compounds of the present subject matter may possess one or more asymmetric centers; such compounds can therefore be produced as individual (R)- or (S)- stereoisomers or as mixtures thereof. Unless indicated otherwise, the description or naming of a particular compound in the specification and claims is intended to include both individual enantiomers, diastereomers mixtures, racemic or otherwise, thereof. Accordingly, the present subject matter also includes all such isomers, including diastereomeric mixtures, pure diastereomers and pure enantiomers of the compounds of Formula I. The term "enantiomer" refers to two stereoisomers of a compound which are non-superimposable mirror images of one another. The term "diastereomer" refers to a stereoisomer with two or more centers of chirality and whose molecules are not mirror images of one another. Diastereomers have different physical properties, e.g. melting points, boiling points, spectral properties, and reactivities.

Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. Enantiomers can also be separated by use of a chiral HPLC column. Methods for the determination of stereochemistry and the separation of stereoisomers are well known in the art (see discussion in Chapter 4 of "Advanced Organic Chemistry", 4th edition, J. March, John Wiley and Sons, New York, 1992).

In the structures shown herein, where the stereochemistry of any particular chiral atom is not specified, then all stereoisomers are contemplated and included as the compounds of the present subject matter. Where stereochemistry is specified by a solid wedge or dashed line representing a particular configuration, then that stereoisomer is so specified and defined.

A single stereoisomer, e.g., an enantiomer, substantially free of its stereoisomer may be obtained by resolution of the racemic mixture using a method such as formation of diastereomers using optically active resolving agents (Eliel, E. and Wilen, S. *Stereochemistry of Organic Compounds*, John Wiley & Sons, Inc., New York, 1994; Lochmuller, C. H., (1975) *J. Chromatogr.*, 113(3):283-302). Racemic mixtures of chiral compounds of the present subject matter can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: *Drug Stereochemistry, Analytical Methods and Pharmacology*, Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (−)menthyl chloroformate in the presence of base, or Mosher ester, α-methoxy-α-(trifluoromethyl) phenyl acetate (Jacob III, (1982) *J. Org. Chem.* 47:4165), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (*Chiral Liquid Chromatography* (1989) W. J. Lough, Ed., Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

The compounds of the present subject matter may comprise geometric isomers. Compounds having a double bound can exist as E or Z isomeric mixtures, which can be separated into their individual E and Z isomers on the basis of their physical chemical differences by methods known to those skilled in the art, for example, by chromatography or fractional crystallization. All such E isomers, Z isomers, and E, Z isomeric mixtures are considered as part of the present subject matter.

In addition to compounds of Formula I, the present subject matter also includes solvates, pharmaceutically acceptable prodrugs, metabolites, and pharmaceutically acceptable salts of such compounds.

The term "solvate" refers to an aggregate of a molecule with one or more solvent molecules.

A "pharmaceutically acceptable prodrug" is a compound that may be converted under physiological conditions or by solvolysis to the specified compound or to a pharmaceutically acceptable salt of such compound. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present subject matter. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine. Particular examples of prodrugs of the present subject matter include a compound of Formula I covalently joined to a phosphate residue or a valine residue.

Additional types of prodrugs are also encompassed. For instance, free carboxyl groups can be derivatized as amides or alkyl esters. As another example, compounds of the present subject matter comprising free hydroxy groups may be derivatized as prodrugs by converting the hydroxy group into groups such as, but not limited to, phosphate ester, hemisuccinate, dimethylaminoacetate, or phosphoryloxymethylcarbonyl groups, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including, but not limited to, ether, amine and carboxylic acid functionalities, or where the acyl group is an amino acid ester as described above, are also encompassed. Prodrugs of this type are described in *J. Med. Chem.*, 1996, 39, 10. More specific examples include replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-$C_6$) alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate).

Free amines can also be derivatized as amides, sulfonamides or phosphonamides. All of these prodrug moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, —C(OH)C(O)OY wherein Y is H, ($C_1$-$C_6$)alkyl or benzyl, —C($OY_0$)$Y_1$ wherein $Y_0$ is ($C_1$-$C_4$) alkyl and $Y_1$ is ($C_1$-$C_6$)alkyl, carboxy($C_1$-$C_6$)alkyl, amino ($C_1$-$C_4$)alkyl or mono-N- or di-N,N-($C_1$-$C_6$)alkylaminoalkyl, —C($Y_2$)$Y_3$ wherein $Y_2$ is H or methyl and $Y_3$ is mono-N- or di-N,N-($C_1$-$C_6$)alkylamino, morpholino, piperidin-1-yl or pyrrolidin-1-yl.

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "Design and Application of Prodrugs," by H. Bundgaard p. 113-191 (1991); c) H. Bundgaard, *Advanced Drug Delivery Reviews*, 8:1-38 (1992); d) H. Bundgaard, et al., *Journal of Pharmaceutical Sciences*, 77:285 (1988); and e) N. Kakeya, et al., *Chem. Pharm. Bull.*, 32:692 (1984), each of which is specifically incorporated herein by reference.

A "metabolite" is a pharmacologically active product produced through in vivo metabolism in the body of a specified compound or salt thereof. Such products may result for example from the oxidation, reduction, hydrolysis, amidation, deamidation, esterification, deesterification, enzymatic cleavage, and the like, of the administered compound. Accordingly, the present subject matter includes metabolites of compounds of Formula I, including compounds produced by a process comprising contacting a compound of the present subject matter with a mammal for a period of time sufficient to yield a metabolic product thereof.

Metabolites are typically identified by preparing a radio-labelled (e.g., $^{14}C$ or $^3H$) isotope of a compound of the present subject matter, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compounds of the present subject matter.

A "pharmaceutically acceptable salt," unless otherwise indicated, includes salts that retain the biological effectiveness of the free acids and bases of the specified compound and that are not biologically or otherwise undesirable. A compound of the present subject matter may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present subject matter with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present subject matter may include more than one acidic or basic moiety, the compounds of the present subject matter may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

The present subject matter also includes isotopically-labeled compounds of the present subject matter which are identical to those recited herein, but for the fact that one or more atoms are replaced by an atom having an atomic mass or mass number different from the atomic mass or mass number usually found in nature. All isotopes of any particular atom or element as specified is contemplated within the scope of the compounds of the present subject matter, and their uses. Exemplary isotopes that can be incorporated into compounds of the present subject matter include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present subject matter (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present subject matter can generally be prepared by following procedures analogous to those disclosed in the Schemes and/or in the Examples herein below, by substituting an isotopically labeled reagent for a non-isotopically labeled reagent.

The inventive compounds may be prepared using the reaction routes and synthetic schemes as described below, employing the techniques available in the art using starting materials that are readily available or can be synthesized using methods known in the art.

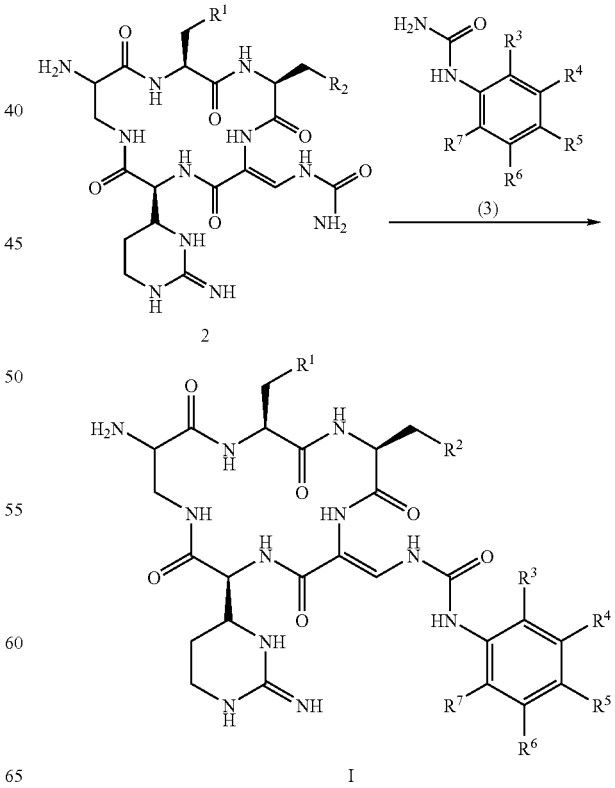

Scheme 1 shows a method of preparing capreomycin derivatives of Formula I. In one embodiment, compounds of Formula I can be prepared by reacting an appropriately substituted phenylurea 3 with capreomycin 2 in water or an organic solvent such as TFA, DMF, acetonitrile, dioxane or DMSO, or a mixed aqueous/organic solvent system such as 50% dioxane and 50% water, in the presence of an inorganic acid such as HCl or $H_2SO_4$, or an organic acid such as TFA, at a temperature between 0° C. to 150° C., in certain embodiments between 65° C. and 85° C., for a period of 5 minutes to 3 days, in certain embodiments for 1-12 hours.

Commercial capreomycin 2 is a mixture of 4 components wherein $R^1$ is OH or H and $R^2$ is $NH_2$ or β-(S)-lysine amide. The major components are those wherein $R^1$=OH and $R^2$=β-(S)-lysine amide (capreomycin IA), and wherein $R^1$=H and $R^2$=β-(S)-lysine amide (capreomycin IB). The minor components are those wherein $R^1$=OH and $R^2$=$NH_2$ (capreomycin IIA) and wherein $R_1$=H and $R^2$=$NH_2$ (capreomycin IIB). When using commercial capreomycin in the reaction shown in Scheme 1, the resultant product is a mixture of four urea derivatives, wherein $R^1$ is OH or H and $R^2$ is $NH_2$ or β-(S)-lysine amide. Accordingly, one aspect of the present subject matter provides a composition comprising one or more compounds of Formula I.

Alternatively, any one of the four components of capreomycin can be prepared according to procedures known to those skilled in the art, such as by fermentation of *Streptomyces capreolus* A250 (M. S. Brown, et al., 1997, *J. Antibiotics*, 50(8), 696-7; Wang, M. and S. J. Gould, 1993, *J. Org Chem.*, 58:5176-5180; S. J. Gould and D. A. Minott, 1992, *J. Org. Chem.*, 57:5214-5217). When published protocols are used as a model for mutagenesis, fermentation, and isolation of capreomycin, it is possible to obtain any of the four components (i.e., IA, IB, IIA or IIB) in a highly enriched state. For example, a mutant of *Streptomyces capreolus*, CAP47-38, consistently produces a 28:1 ratio in favor of capreomycin IA when fermented in F10a production medium. Accordingly, another aspect of the present subject matter provides a method of producing urea analogs of capreomycin IA, capreomycin IB, capreomycin IIA or capreomycin IIB.

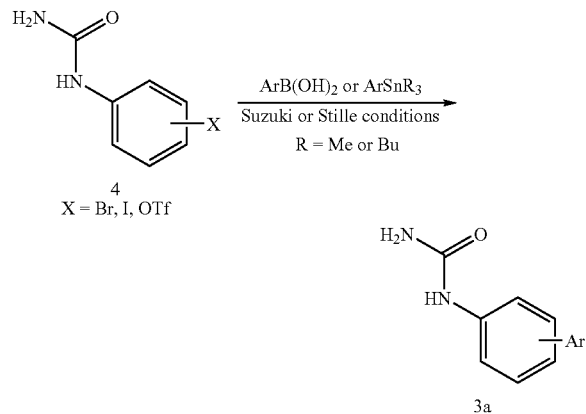

Scheme 2 shows a method of preparing a biaryl urea 3a for use in the method of Scheme 1. In one embodiment, compound 3a can be prepared by reacting a halogen-containing phenylurea 4 (X=Br or I) or an O-trilfate-containing phenylurea 4 under Suzuki or Stille-type palladium-catalyzed conditions with an appropriately substituted aryl or heteroaryl boronic acid $ArB(OH)_2$ or an appropriately substituted aryl or heteroaryl tin species, for example $ArSnMe_3$ or $ArSnBu_3$. Suzuki coupling reactions can be carried out as described by N. Miyaura and A. Suzuki, *Chemical Reviews* 95, 2457, 1995. Stille reactions are performed using conditions described by V. Farina et al., *Org. Reactions*, 50, 1, 1997.

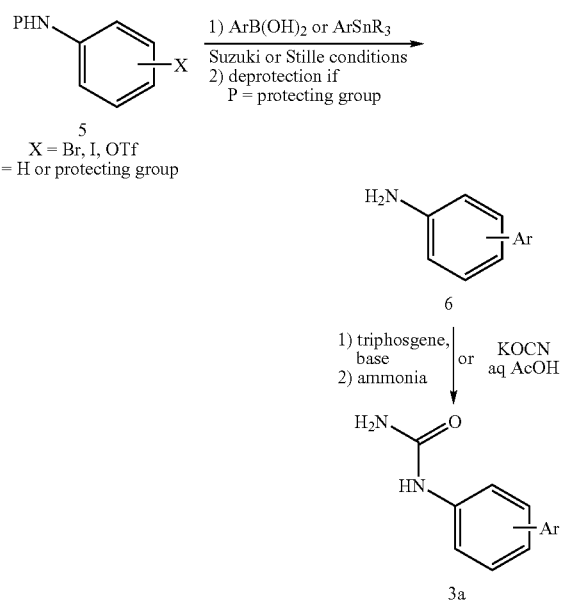

Scheme 3 shows an alternative method of preparing a biaryl urea 3a. In one embodiment, compound 6 can be prepared by reacting a halogen-containing aniline 5 (X=Br or I) or O-trilfate-containing phenylaniline 5, wherein the aniline can be protected or unprotected, under Suzuki or Stille-type palladium-catalyzed conditions with an appropriately substituted aryl or heteroaryl boronic acid $ArB(OH)_2$ or an appropriately substituted aryl or heteroaryl tin species, for example $ArSnMe_3$ or $ArSnBu_3$. In embodiments wherein the aniline moiety of compound 6 is protected, the aniline is deprotected prior to the conversion into compound 3a. Protection and deprotection of anilines are well known to those skilled in the art, and such methods are also described in T. W. Greene and P. G. M. Wuts in "Protective Groups in Organic Synthesis", 3rd edition, 1999. Biaryl urea 3a can be prepared by reacting substituted aniline 6 or the acid salt of the aniline with either sodium or potassium cyanate in water or an organic solvent such as acetic acid THF, DMF, acetonitrile, dioxane or DMSO, or a mixed solvent system such as 50% acetic acid and 50% DMF, at a temperature between 0° C. to 150° C., in certain embodiments between 5° C. and 35° C., for a period of 5 minutes to 3 days, in certain embodiments for 1-4 hours. In another embodiment, biaryl urea 3a can be prepared as shown in Scheme 3 by reacting substituted aniline 6 with a reagent such phosgene, triphosgene, phenyl chloroformate or 4-nitrophenylchloroformate in an organic solvent such as dichloromethane, dichloroethane, or THF, in the presence of an organic base such as triethylamine, diethylisopropylamine, pyridine, DBU, or 2,6-lutidine, at a temperature between −78° C. to 80° C., in certain embodiments between −78° C. and 35° C., for a period of 5 minutes to 3 days, in certain embodiments for 1-12 hours. The resulting mixture is then treated with an ammonia source such as ammonia gas, ammonium hydroxide, or ammonia dissolved in an organic solvent like methanol or dioxane, at a temperature between −78° C. to 45° C., in certain embodiments between 0° C. and 35° C., for a period of 5 minutes to 3 days, in certain embodiments 1-12 hours

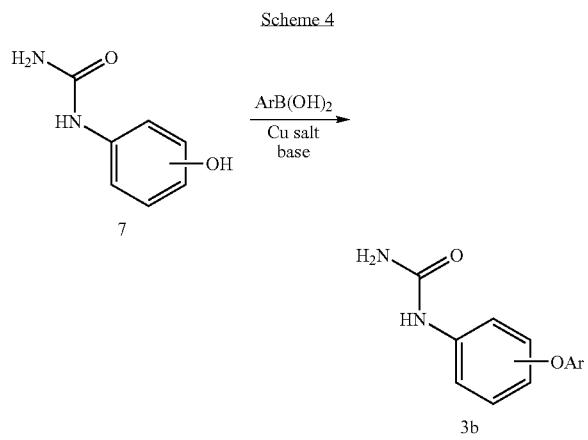

Scheme 4 shows how to prepare a biaryl ether urea 3b for use in the method of Scheme 1. In one embodiment, compound 3b can be prepared by reacting a phenolic urea 7 under copper catalyzed conditions with an appropriately substituted aryl or heteroaryl boronic acid ArB(OH)$_2$. These copper-catalyzed coupling reactions can be carried out as described by Evans, D., et. al., *Tetrahedron Lett.* 39, 2937, 1998 or Marcoux, J.-F., et. al., *J. Am. Chem. Soc.* 119, 10539, 1997.

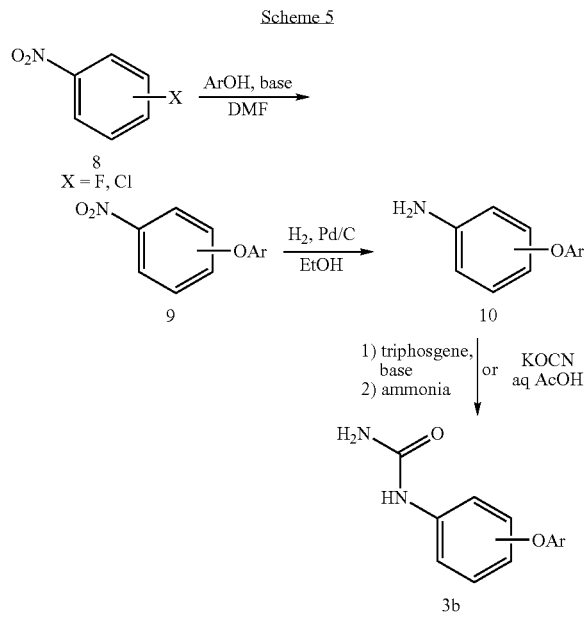

Scheme 5 shows an alternative way to prepare biaryl ether urea 3b. An appropriately substituted aniline 10 can be prepared as shown in Scheme 5 in two steps from compound 8, which can then be transformed into compound 3b. In one embodiment, compound 9 can be prepared from a halogen-containing (X=F or Cl) nitroaryl compound 8, upon reaction with an appropriately substituted phenoxide in the presence of a base such as NaH, K$_2$CO$_3$, or Cs$_2$CO$_3$, in an organic solvent such as DMF or DMSO, at a temperature between 0° C. to 150° C. Compound 10 can be prepared from compound 9 by reduction with hydrogen gas and a catalyst such as Pd/C, Raney Ni, PtO$_2$, or Ru, in a solvent such as EtOH or MeOH. Additional methods of preparing compound 10 from compound 9 include (i) transfer hydrogenation using a hydrogen source such as cyclohexene or formic acid and a catalyst such as Pd/C, (ii) reduction with NaBH$_4$ and a catalyst such as Pd/C, TiCl$_4$, NiCl$_2$.6 H$_2$O or Cu(OAc)$_2$, or (iii) reduction Zn with HCl, NaOH, or NH$_3$. Biaryl ether urea 3b can be prepared as shown in Scheme 5 by the methods employed for preparing biaryl ether ureas as described for Scheme 3.

The present subject matter also includes methods of treating or preventing a bacterial infection or disease or condition caused by a bacterial infection in a mammal, comprising administering to said mammal a compound of Formula I, or a solvate, metabolite, or pharmaceutically acceptable salt or prodrug thereof.

As used herein, the term "treating" is intended to mean reversing, alleviating, inhibiting the progress of, or preventing a disease or condition in a mammal, such as a human, that has a bacterial infection and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition. The term "treatment," as used herein, unless otherwise indicated, refers to the act of treating as "treating" is defined immediately above. The terms "treating", "treat", or "treatment" embrace both preventative, i.e., prophylactic, and palliative treatment.

The phrase "therapeutically effective amount" means an amount of a compound of the present subject matter that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

As used herein, unless otherwise indicated, the terms or phrases "bacterial infection(s)" and "disorders related to bacterial infections" include, but are not limited to pneumonia, otitis media, sinusitis, bronchitis, tonsillitis and mastoiditis related to infection by *Streptococcus pneumoniae, Haemophilus influenzae, Moraxella catarrhalis, Staphylococcus aureus, Enterococcus faecalis, E. Faecium, E. caaelflavus, S. epidermis, S. haemolyticus,* or *Peptostreptococcus spp.*; pharyngitis, rheumatic fever and glomerulonephritis related to infection by *Streptococcus pyogenes,* Groups C and G streptococci, *Corynebacterium diphtheriae* or *Actinobacillus haemolyticum*; respiratory tract infections related to infection by *Mycobacteria spp., Mycoplasma pneumoniae, Legionella pneumophila, Streptococcus pneumoniae, Haemophilus influenzae,* or *Chlamydia pneumoniae*; blood and tissue infections, including edocarditis and osteomyelitis, caused by *S. aureus, S. haemolyticus, E. faecalis, E. Faecium, E. durans,* including strains resistant to known antibacterials such as, but not limited to, beta-lactams, vancomycin, aminoglycosides, quinolones, chloramphenicol, tetracyclines, streptogramins (such as Synercid), lipopetides (such as Daptomycion), oxazolidinones (such as Linezolide) and macrolides; uncomplicated skin and soft tissue infections and abscesses, and puerperal fever related to infection by *Staphylococcus aureus*, coagulase-negative *staphylococci* (i.e., *S. epidermis, S. haemolyticus*, etc.), *Streptococcus pyogenes, Streptococcus agalactiae, Streptococcal* groups C—F (minute-colony streptococci), *viridans streptococci, Corynebacterium minutissimum, Clostridium* spp., or *Bartonella henselae*; complicated skin and soft tissue infections related to infection by *S. aureus, P. aeruginosa, Enterococcus* spp., *Enterobacter* spp.; uncomplicated acute urinary tract infections related to infection by *Staphylococcus aureus*, coagulase-negative *staphylococcal* species, or *Enterococcus* spp.; complicated urinary tract infections realted to infection by *S. aureus, Pseudomonas* spp., *Klebsiella* spp., *Proteus* spp., *Enterococcus* spp., *Enterobacter* spp.; urethritis and cervicitis; sexually transmitted diseases related to infection by *Chiamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome) or Group A, B and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neiserria gonorrheae, S. aureus, S. pneumoniae, S. pyogenes, H. influenzae, Listeria* spp., disseminated *Mycobacterium avium*, or *Mycobacterium intracellulare*; infections caused by *Mycobacterium tuberculosis, M. Leprae, M. paratuberculosis, M. kanasasii*, or *M. chelonei*; gastroenteritis related to infection by *Campylobacter jejuni*; antibiotic-associated diarrhea; colitis or pseudomembraneous colitis related to infection by *Clostridium difficile, Clostridium perfingens*, and *S. aureous*; odontogenic infection by *viridans streptococci*; persistent cough related to infection by *Bordetella pertussis*; gas gangrene related to infection by *Clostridium perfingens* or *Bacteroides* spp.; and atherosclerosis or cardiovascular disease related to infection by *Helicobacter pylori* or *Chlamydia pneumoniae*.

Disorders related to bacterial infections which may be treated or prevented in mammals according to the methods of the present subject matter also include the following: bovine respiratory disease related to infection by *P. haemolytica, P. multocida, Mycoplasma bovis*, or *Bordetella* spp.; dairy cow mastitis related to infection by *S. aureus, Strep. Uberis, Streptococcus agalactiae, Streptococcus dysgalactiae, Corynebacterium*, or *Enterococcus* spp.; swine respiratory disease related to infection by *A. pleuro., P. multocida*, or *Mycoplasma* spp.; swine enteric disease related to infection by *Lawsonia intracellularis, Salmonella*, or *Serpulia hyodysinteriae*; cow foot-rot related to infection by *Fusobacterium* spp.; cow hairy warts related to infection by *Fusobacterium necrophorum* or *Bacteroides nodosus*; cow pink eye related infection by *Moraxella bovis*; skin and soft tissue infections in dogs and cats related to infection by *S. epidermis, S. intermedius, coagulase negative Staphylococcus* or *P. muloticda*; and dental and mouth infections in dogs and cats related to infection by *Alcaligenes* spp., *Bacteroides* spp., *Clostridium* spp., *Enterobacter* spp., *Eubacterium, Peptostreptococcus, Porphyromonas*, or *Prevotella*. Other bacterial infections and disorders related to such infections, which may be treated or prevented in accord with the method of the present subject matter are referred to in J. P. Sanford et al., "The Sanford Guide To Antimicrobial Therapy," 26$^{th}$ Edition, (Antimicrobial Therapy, Inc., 1996).

The size of the dose for therapeutic or prophylactic purposes of a compound of Formula I will naturally vary according to the nature and severity of the conditions, the age and sex of the animal or patient and the route of administration, according to well known principles of medicine.

The compounds of the present subject matter may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

In order to use a compound of Formula I or a pharmaceutically acceptable salt, solvate, metabolite, prodrug thereof, for the therapeutic treatment (including prophylactic treatment) of mammals including humans, it is normally formulated in accordance with standard pharmaceutical practice as a pharmaceutical composition. According to this aspect of the present subject matter there is provided a pharmaceutical composition that comprises a compound of Formula I, or a solvate, metabolite, or pharmaceutically acceptable salt or prodrug thereof, in association with a pharmaceutically acceptable diluent or carrier.

A typical formulation is prepared by mixing a compound of the present subject matter and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present subject matter is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present subject matter or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present subject matter or stabilized form of the compound (e.g., complex with a cyclodextrin derivative or other known complexation agent) is dissolved in a suitable solvent in the presence of one or more of the excipients described above. The compound of the present subject matter is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present subject matter may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug (such as the Raf inhibitors disclosed herein and, optionally, a chemotherapeutic agent) to a mammal. The components of the liposome are commonly arranged in a bilayer formation, similar to the lipid arrangement of biological membranes.

The compositions of the present subject matter may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the present subject matter may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of the present subject matter that is combined with one or more excipients to produce a single dosage form will necessarily vary depending upon the subject treated, the severity of the disorder or condition, the rate of administration, the disposition of the compound and the discretion of the prescribing physician. However, an effective dosage is in the range of about 0.001 to about 100 mg per kg body weight per day, preferably about 0.1 to about 35 mg/kg/day, in single or divided doses. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

A compound of the present subject matter may be used alone in combination with other drugs and therapies used in the treatment of bacterial infections and disorders related to such infections. For example, a compound of the present subject matter may be applied in combination with one or more other antibiotics including β-lactams such as carbapenems, cephalosporins (ceftriaxone), and penicillins; aminoglycosides (as exemplified by gentamicin and including but not limited to amikacin, dibekacin, streptomycin, neomycin, kanamycin, spectinomycin, kasugamycin); fluoroquinolones (as exemplified by ciprofloxacin and including but not limited to trovafloxacin, sparfloxacin, gatifloxacin, grepafloxacin, ofloxacin, norfloxacin, floxin, levofloxacin) and related quinolones and naphthyridines with activity against topoisomerases; chloramphenicol; as well as macrolides, ketolides azalides (and other related polyketides), Synercid®, tetracyclines (including glyctlcyclines), glycopeptides (including, but not limited to, vancomycin, teicoplanin, Ortivancin, Telavancin), novobiocin (and coumermycin), lipopeptides (including but not limited to Daptomycin) and oxazolidinones (including but not limited to Linezolid). Such conjoint treatment may be achieved by way of the simultaneous, sequential or separate dosing of the individual components of treatment.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In another embodiment of the present subject matter, an article of manufacture, or "kit", containing materials useful for the treatment of the disorders described above is provided. In one embodiment, the kit comprises a container comprising a compound of Formula I, or a solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating a bacterial infection. Alternatively, or additionally, the kit may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with antibacterial activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. The kit may further comprise directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

BIOLOGICAL EXAMPLES

The biological activities of the compounds of the present subject matter were demonstrated by the following assays.

One assay employs conventional methodology and interpretation criteria and is designed to provide direction for chemical modifications that may lead to compounds with antibacterial activity against susceptible and drug resistant organisms including, but not limited to, beta-lactam, macrolide, and vancomycin resistant organisms. In the assay, a panel of bacterial strains is assembled to include a variety of target pathogenic species including representatives of antibiotic resistant bacteria. Use of this panel enables the chemical structure/activity relationship to be determined with respect to potency and spectrum of activity. The assay performed in microtiter trays and interpreted according to the guidelines in Performance Standards for Antimicrobial Disk Susceptibility (Sixth Edition; Approved Standard, published by The National Committee for Clinical Laboratory Standards (NCCLS)). The minimum inhibitory concentration (MIC) is used to compare strains. Compounds are initially dissolved in phosphate buffer stock solutions.

The activity of the compounds of the present subject matter also may be assessed in accord with Steers replicator technique which is a standard in vitro bacterial testing method described by Steers, et al., 1959, *Antibiotics and Chemotherapy*, 9:307.

The in vivo activity of the compounds of the present subject matter can be determined by conventional animal protection studies well known to those skilled in the art, usually carried out in rodents.

According to one in vivo model, compounds were evaluated for efficacy in mouse models of acute bacterial infection as follows. Mice (ICR male; 22-26 g) were allotted to APEC$^R$ cages upon their arrival, and allowed to acclimate for at least 1 week before being placed in a study. All animals were maintained in a hygienic environment under a controlled temperature (22-23° C.) and humidity (50%-60%) with 12 hours light/dark cycles for at least one week. Free access to standard lab chow (LabDiet Rodent Diet, PMI International, USA) and tap water was granted. The acute infection was produced by intravenous inoculation with an $LD_{90}0_{100}$ dose of bacteria (*Staphylococcus aureus* methicillin resistant strain ATCC 33591, 8.0×10$^7$ CFU/mouse) suspended in 0.2 mL of phosphate buffer pH 7.4 without 5% mucin.

Mice (10 per group) were treated subcutaneously at 1 hour after challenge. Appropriate non-treated (infected but not treated) and positive (vancomycin or minocycline) controls were included in each study. Percent survival was recorded once daily for 10 days. At the end of 10 days of dosing, an increase of survival by 50 percent or more relative to vehicle control indicated a significant effect. The $PD_{50}$ (mg/kg/dose calculated to protect 50% of infected animals) is determined by the probit method.

PREPARATIVE EXAMPLES

In order to illustrate the present subject matter, the following examples are included. However, it is to be understood that these examples do not limit the present subject matter and are only meant to suggest a method of practicing the present subject matter. Persons skilled in the art will recognize that the chemical reactions described may be readily adapted to prepare a number of other capreomycin analogs of the present subject matter, and alternative methods for preparing the compounds of the present subject matter are deemed to be within the scope of the present subject matter. For example, the synthesis of non-exemplified compounds according to the present subject matter may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the present subject matter.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane, toluene, dioxane and 1,2-difluoroethane were purchased from Sigma-Aldrich in Sure seal bottles and used as received. Capreomycin sulfate was purchased from Sigma-Aldrich.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

EXAMPLE 1

Preparation of Compound Mixture 1

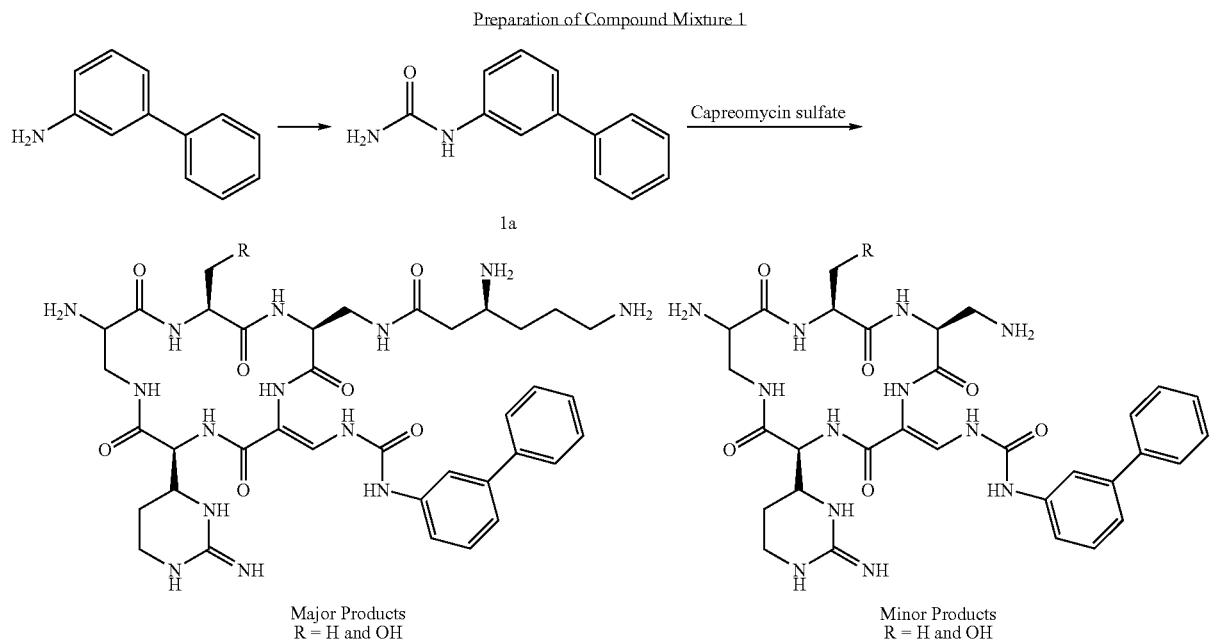

Major Products
R = H and OH

Minor Products
R = H and OH

1

Step A: 20.0 g of 3-aminobiphenyl was dissolved in a solution of 250 mL of acetic acid and 200 mL of water under an atmosphere of dry $N_2$. To this mixture was added, portionwise, 13.42 g of potassium cyanate. The reaction mixture was stirred for about 2 hours after which time it was diluted with 500 mL of water. The precipitate was collected via suction filtration and was then washed with water and finally air-dried to give a white solid as the desired product. The solid was taken up in 200 mL of ethyl ether and stirred at room temperature for about 1 hour after which time it was filtered. The resulting solid was then taken up in 200 mL of isopropanol and stirred at room temperature for about 1 hour and then filtered. The solid was washed with ethyl ether and then air-dried to give 17.7 g of 3-biphenylurea as a white solid. The material was used in Step B without further purification.

Step B: Capreomycin sulfate (16.3 g) and 3-biphenylurea (27.7 g) were dissolved/suspended in 300 mL of a 1:1 solution of dioxane/1 N aqueous HCl. The reaction mixture was heated at 65° C. overnight. The reaction mixture was cooled to room temperature and filtered, and the resulting filtrate was adjusted to ~pH 7.2 with the addition of NaHCO$_3$ and then diluted with 200 mL of saturated brine. The mixture was then partitioned between ethyl acetate and water. The water layer was washed 5 times with ethyl acetate, and then 650 g of activated Amberlite XAD-16 resin (activated by stirring in methanol 20 minutes, filtering and washing with water) was added to the water layer and the resulting heterogeneous mixture was stirred for about 2 hours. The resin was then collected via suction filtration and subsequently washed several times with water. The resin was transferred to a beaker to which was added about 600 mL of methanol/water (9:1), and the resulting slurry was stirred for about 30 minutes. The resin was then filtered and the previous step was repeated. The filtrates were combined and then concentrated under vacuum to give 11.59 g of compound mixture 1 as HCl salts (major products MH+=821, 805; minor products MH+=676, 692).

EXAMPLE 2

Preparation of Compound Mixture 2

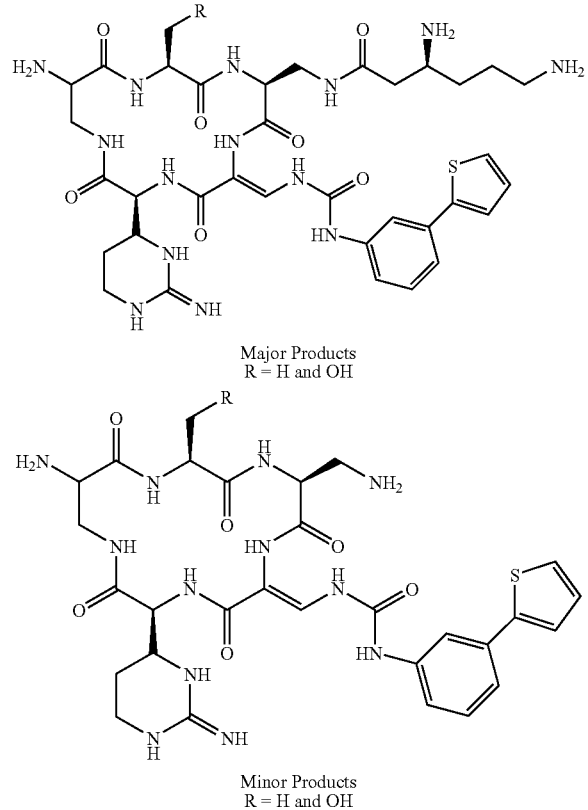

Major Products
R = H and OH

Minor Products
R = H and OH

Step A: 3-Bromopheylurea (10.40 g), 2-thiopheneboronic acid (8.20 g) and palladium tetrakistriphenylphosphine (2.63 g) were added to a flask containing 300 mL of dimethoxyethane and 100 mL of 2.0 M aqueous potassium carbonate under an atmosphere of dry N$_2$. The reaction mixture was heated at 90° C. overnight. The reaction mixture was then cooled to room temperature and partitioned between EtOAc and water. The EtOAc layer was dried over MgSO$_4$, filtered and concentrated under vacuum. The resulting residue was tritutrated with ethyl ether to give 9.00 g of 1-(3-(thiophen-2-yl)phenyl)urea.

Step B: Capreomycin was reacted with 1-(3-(thiophen-2-yl)phenyl)urea according to the procedure of Example 1 to give compound mixture 2 as HCl salts (major products MH+=811, 827; minor products MH+=682, 698).

EXAMPLE 3

Preparation of Compound Mixture 3

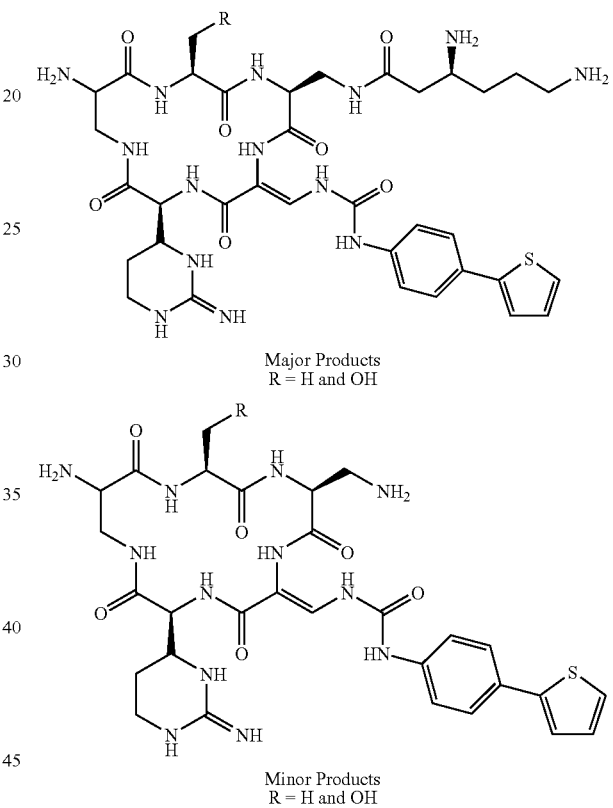

Major Products
R = H and OH

Minor Products
R = H and OH

Step A: 10.1 g of 4-iodoaniline, 7.60 g of 2-thiopheneboronic acid, and 2.40 g of palladium tetrakistriphenylphosphine were dissolved/suspended in a solution of 150 mL of dimethoxyethane and 68 mL of 2.0 M aqueous potassium carbonate under an atmosphere of dry N$_2$. The reaction mixture was heated to 90° C. and reacted at this temperature over night. The reaction mixture was then cooled to room temperature and then partitioned between EtOAc and water. The EtOAc layer was then dried over MgSO$_4$, filtered and concentrated under vacuum. The resulting residue was purified using silica gel chromatography eluting with a 2:1 solution of DCM/Hexanes and then DCM to give 2.80 g of 1-(4-(thiophen-2-yl)phenyl)urea.

Step B: Capreomycin sulfate and 1-(4-(thiophen-2-yl)phenyl)urea were reacted according to the method of Example 1, Step B to provide compound mixture 3 (major products MH+=821, 805; minor products MH+=676, 692).

EXAMPLE 4

Preparation of Compound Mixture 4

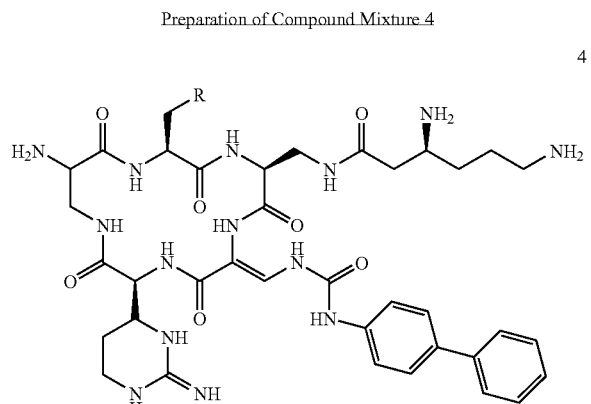

Major Products
R = H and OH

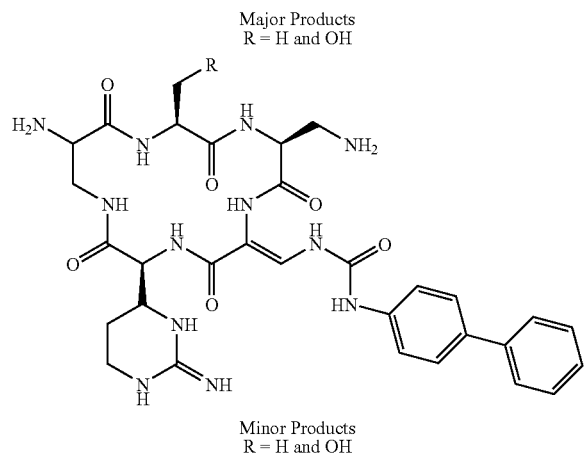

Minor Products
R = H and OH

Compound mixture 4 was prepared according to the method of Example, Steps A and B, except that 4-aminobiphenyl was substituted for 3-aminobiphenyl, to provide the desired compounds as HCl salts (major products MH+=821, 805; minor products MH+=676, 692).

EXAMPLE 5

Preparation of Compound Mixture 5

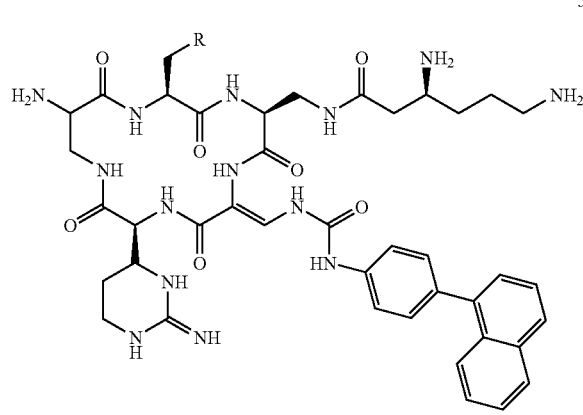

Major Products
R = H and OH

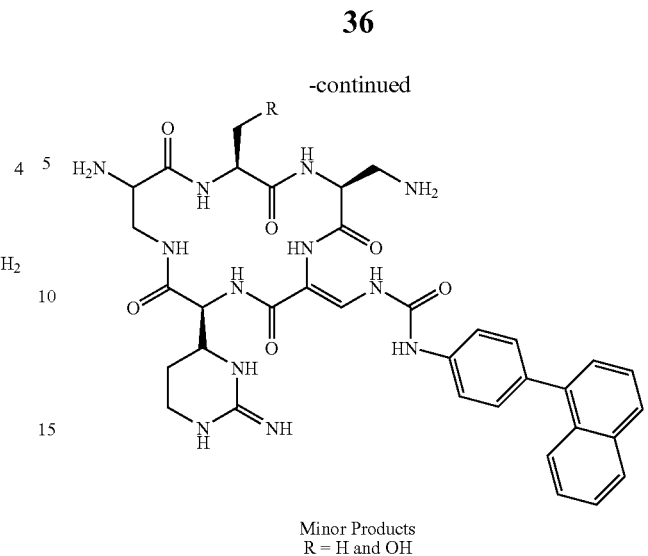

Minor Products
R = H and OH

Compound mixture 5 was prepared according to Example 3, except that 1-napthaleneboronic acid was substituted for 2-thiopheneboronic acid, to provide the desired products (major products MH+=855, 871; minor products MH+=727, 743).

EXAMPLE 6

Preparation of Compound Mixture 6

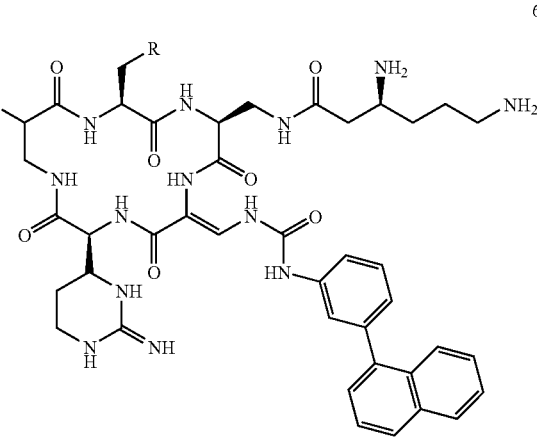

Major Products
R = H and OH

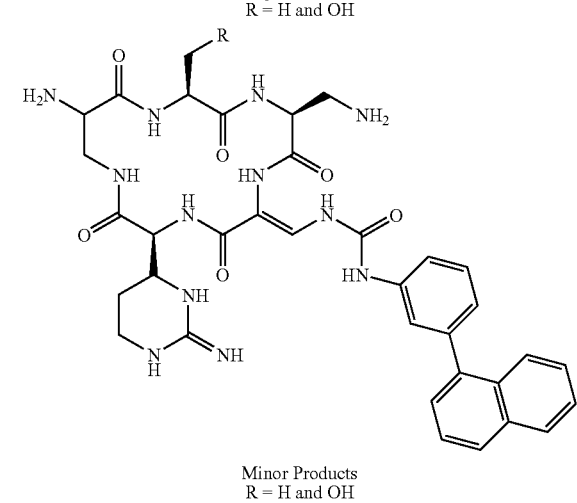

Minor Products
R = H and OH

Compound mixture 6 was prepared as an HCl salt according to the procedure outlined in Example 3, substituting 2-thiopheneboronic acid with 1-napthaleneboronic acid and substituting 4-iodoaniline with 3-iodoaniline (major products MH+=855, 871; minor products MH+=727, 743).

2-thiopheneboronic acid with 2-napthaleneboronic acid and substituting 4-iodoaniline with 3-iodoaniline (major products MH+=855, 871; minor products MH+=727, 743).

EXAMPLE 7

EXAMPLE 8

Preparation of Compound Mixture 7

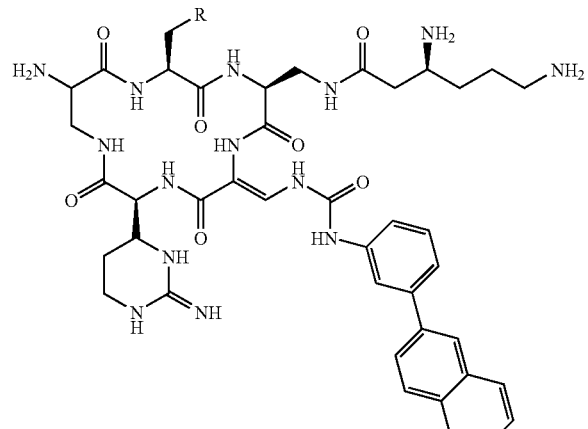

Major Products
R = H and OH

Preparation of Compound Mixture 8

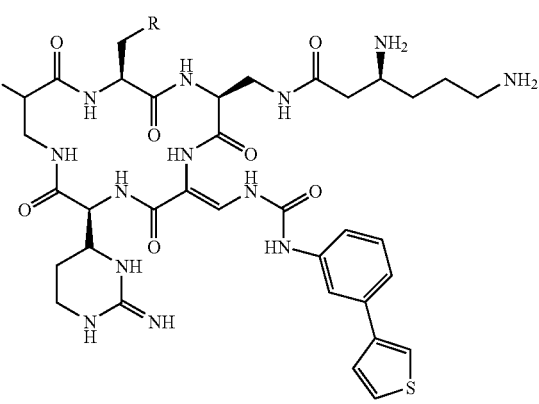

Major Products
R = H and OH

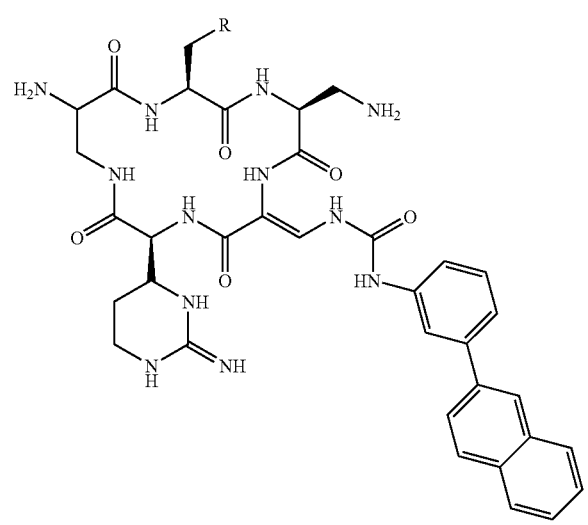

Minor Products
R = H and OH

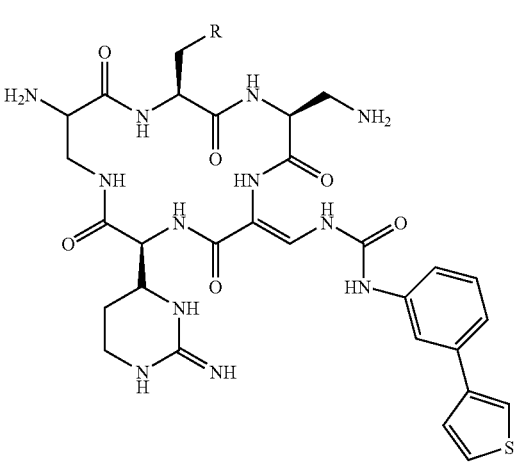

Minor Products
R = H and OH

Compound mixture 7 was prepared as an HCl salt according to the procedure outlined in Example 3, substituting Compound mixture 8 was prepared as an HCl salt according to the procedure outlined in Example 3, substituting 2-thiopheneboronic acid with 3-thiopheneboronic acid and substituting 4-iodoaniline with 3-iodoaniline (major products MH+=811, 827; minor products MH+=683, 699).

EXAMPLE 9

Preparation of Compound Mixture 9

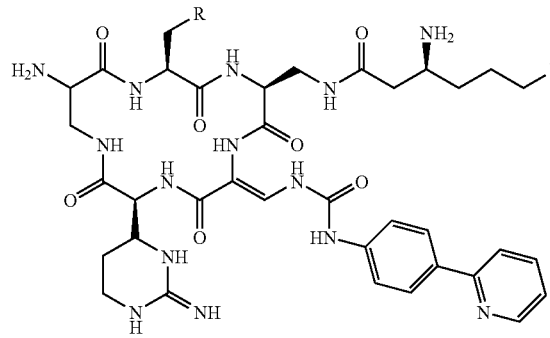

Major Products
R = H and OH

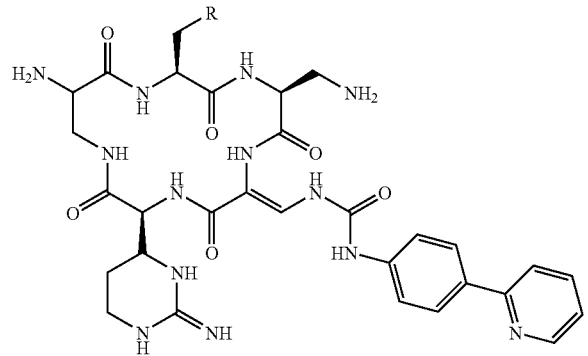

Minor Products
R = H and OH

Step A: 2-Bromopyridine (650 μL), 4-nitrophenylboronic acid (1.479 g) and palladium tetrakistriphenylphosphine (391.5 mg) were added to a mixture of 40 mL of dimethoxyethane and 10 mL of 2.0 M aqueous potassium carbonate under an atmosphere of dry $N_2$. The reaction mixture was heated at 95° C. overnight. The reaction mixture was then cooled to room temperature and diluted with water (200 mL). The resulting precipitate was collected, washed with water and air-dried. The dried material was purified using silica gel chromatography to give 1.40 g of 2-(4-nitrophenyl)pyridine.

Step B: 2-(4-Nitrophenyl)pyridine (1.10 g) and 10% Pd/C (300 mg) were dissolved suspended in 80 mL of an 8:1 solution of 30 mL of THF and 10 mL of ethanol under an atmosphere of dry $N_2$. To this solution was added 1.0 mL of anhydrous hydrazine. The reaction mixture was stirred at room temperature overnight and then filtered. The filtrate was concentrated under vacuum. The residue was partitioned between dichloromethane and water and the organic layer was washed with brine, dried over $MgSO_4$, filtered and concentrated under vacuum. The residue was purified via silica gel chromatography to give 653.3 mg of 4-(pyridin-2-yl)benzenamine.

Step C: Compound mixture 9 was prepared as the HCl salt according to the procedure outlined in Example 1, except that 3-aminobiphenyl was replaced with 4-(pyridin-2-yl)benzenamine (major products MH+=806, 822; minor products MH+=678, 694).

EXAMPLE 10

Preparation of Compound Mixture 10

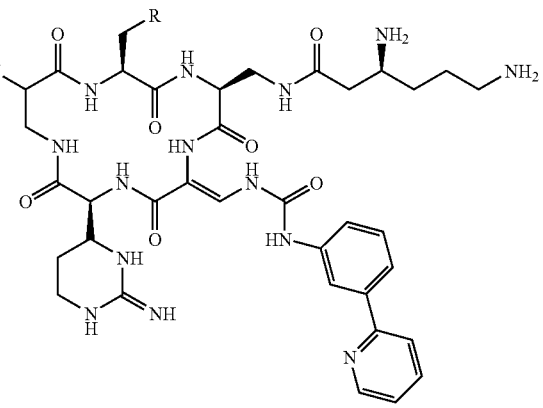

Major Products
R = H and OH

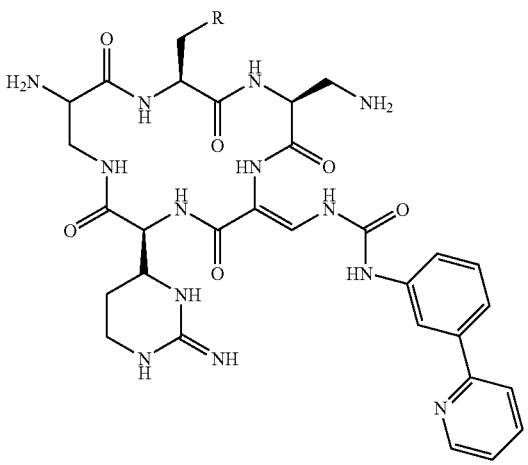

Minor Products
R = H and OH

Step A: 2-Bromopyridine (2.00 mL), 3-aminophenylboronic acid (5.40 g) and palladium tetrakistriphenylphosphine (1.2512 g) were added to a mixture of 130 mL of dimethoxyethane and 32 mL of 2.0 M aqueous potassium carbonate under an atmosphere of dry $N_2$. The reaction mixture was heated at 90° C. overnight. The reaction mixture was then cooled to room temperature and diluted with water (300 mL). The resulting precipitate was collected, washed with water and air-dried. The dried material was purified using silica gel chromatography to give 2.75 g of 3-(pyridin-2-yl)benzenamine.

Step B: Compound mixture 10 was prepared as an HCl salt according to the procedure outlined in Example 1, except that 3-aminobiphenyl was replaced with 3-(pyridin-2-yl)benzenamine (major products MH+=806, 822; minor products MH+=678, 694).

EXAMPLE 11

Preparation of Compound Mixture 11

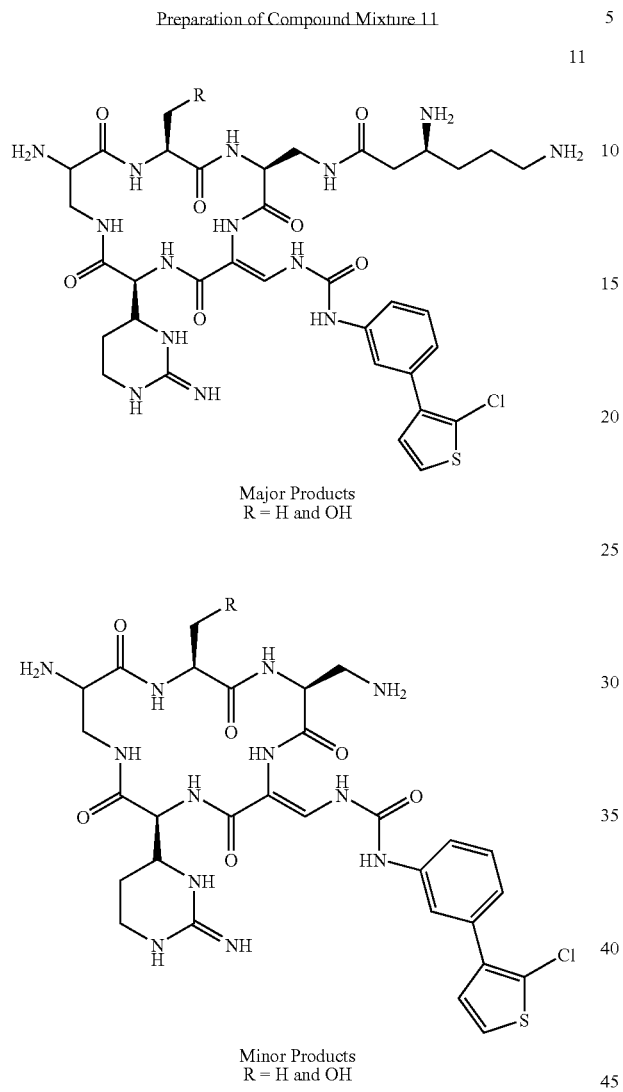

Major Products
R = H and OH

Minor Products
R = H and OH

Step A: 3-bromo-2-chlorothiophene (1.00 mL), 3-aminophenylboronic acid (2.2266 g) and palladium tetrakistriphenylphosphine (544.8 mg) were combined in a mixture of 40 mL of dimethoxyethane and 15 mL of 2.0 M aqueous potassium carbonate under an atmosphere of dry $N_2$. The reaction mixture was heated at 90° C. overnight. The reaction mixture was then cooled to room temperature and partitioned between EtOAc and water. The EtOAc layer was then dried over $MgSO_4$, filtered and concentrated under vacuum. The resulting residue was purified using silica gel chromatography eluting with a 1:1 solution of DCM/Hexanes, followed by a 4:3 solution of DCM/Hexanes and finally a 2:1 solution of DCM/Hexanes, to give 1.80 g of 3-(2-chlorothiophen-3-yl)benzenamine.

Step B: Compound mixture 11 was prepared as an HCl salt according to the procedure outlined in Example 1, substituting 3-aminobiphenyl with 3-(2-chlorothiophen-3-yl)benzenamine (major products MH+=845, 861; minor products MH+=717, 733).

EXAMPLE 12

Preparation of Compound Mixture 12

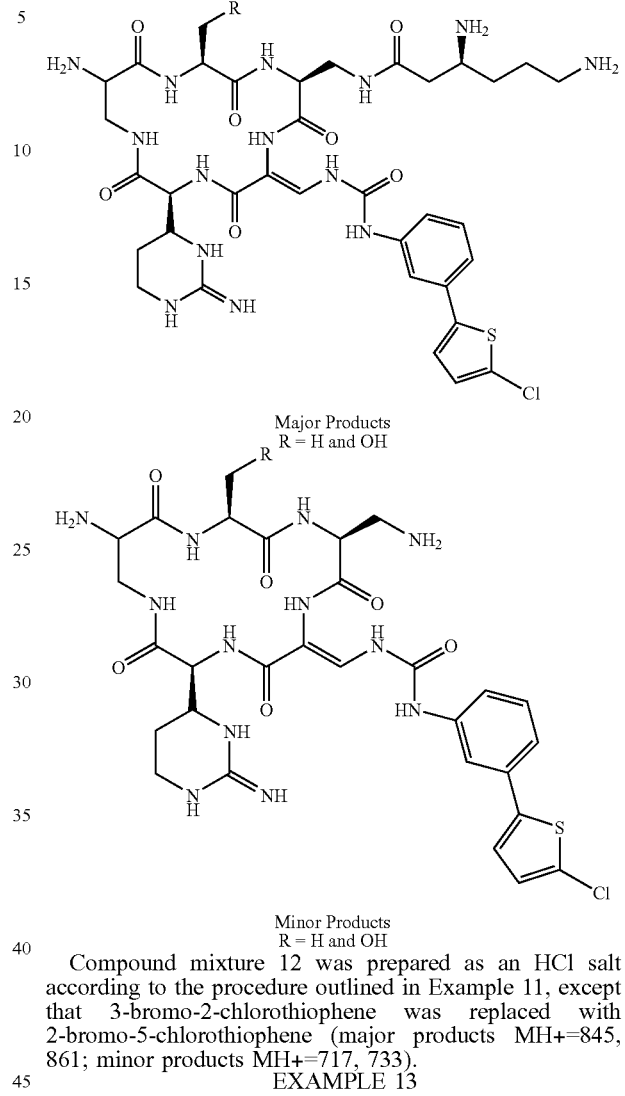

Major Products
R = H and OH

Minor Products
R = H and OH

Compound mixture 12 was prepared as an HCl salt according to the procedure outlined in Example 11, except that 3-bromo-2-chlorothiophene was replaced with 2-bromo-5-chlorothiophene (major products MH+=845, 861; minor products MH+=717, 733).

EXAMPLE 13

Preparation of Compound Mixture 13

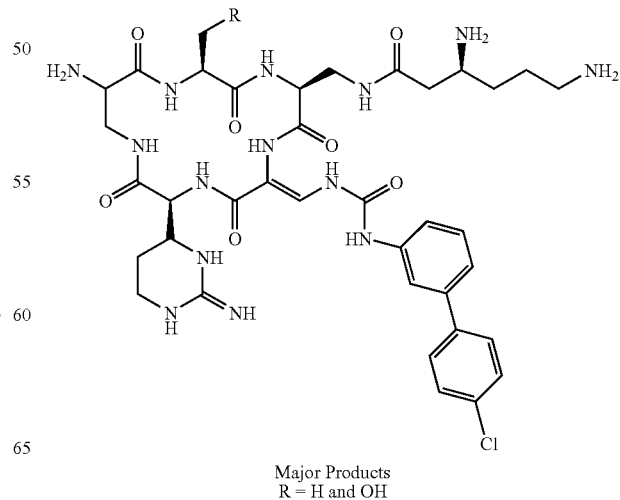

Major Products
R = H and OH

-continued

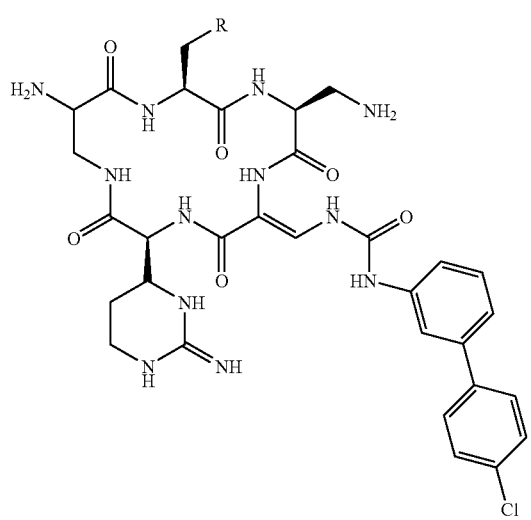

Minor Products
R = H and OH

Compound mixture 13 was prepared as an HCl salt according to the procedure outlined in Example 1, except that 3-aminobiphenyl is replaced with 4'-chloro-3-aminobiphenyl (major products MH+=839.4, 855.3; minor products MH+=711.3, 727.3).

EXAMPLE 14

Preparation of Compound Mixture 14

14

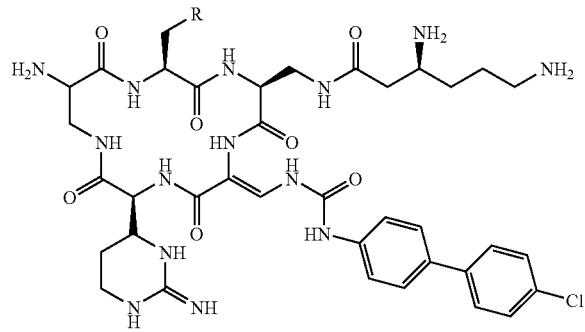

Major Products
R = H and OH

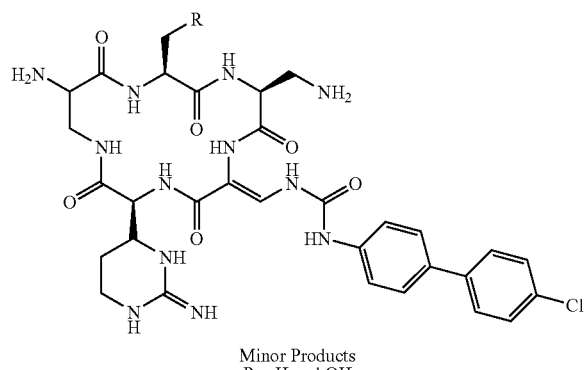

Minor Products
R = H and OH

Compound mixture 14 was prepared as an HCl salt according to the procedure outlined in Example 1, except that 3-aminobiphenyl is replaced with 4'-chloro-4-aminobiphenyl (major products MH+=839.4, 855.4; minor products MH+=711.3, 727.3).

EXAMPLE 15

Preparation of Compound Mixture 15

15

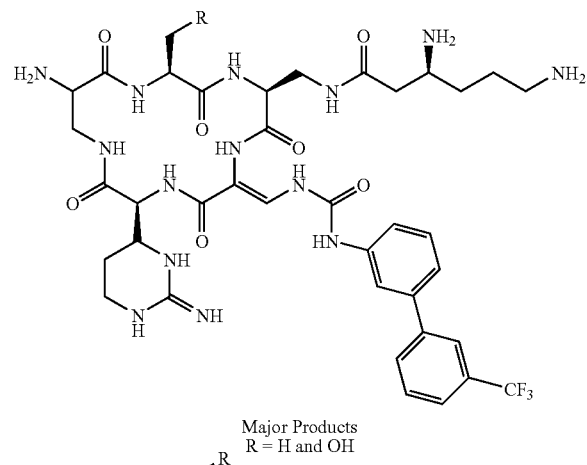

Major Products
R = H and OH

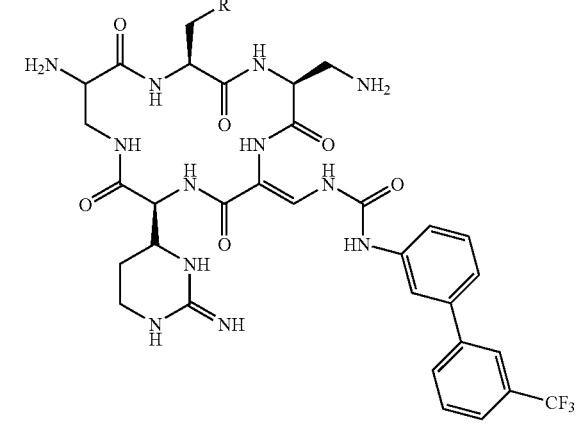

Minor Products
R = H and OH

Compound mixture 15 was prepared as an HCl salt according to the procedure outlined in Example 1, except that 3-aminobiphenyl is replaced with 3'-trifluoromethyl-3-aminobiphenyl (major products MH+=873.4, 889.4; minor products MH+=745.4, 761.3).

EXAMPLE 16

Preparation of Compound Mixture 16

16

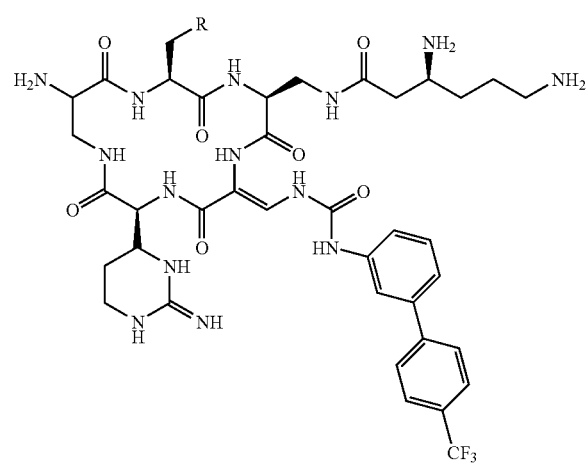

Major Products
R = H and OH

-continued

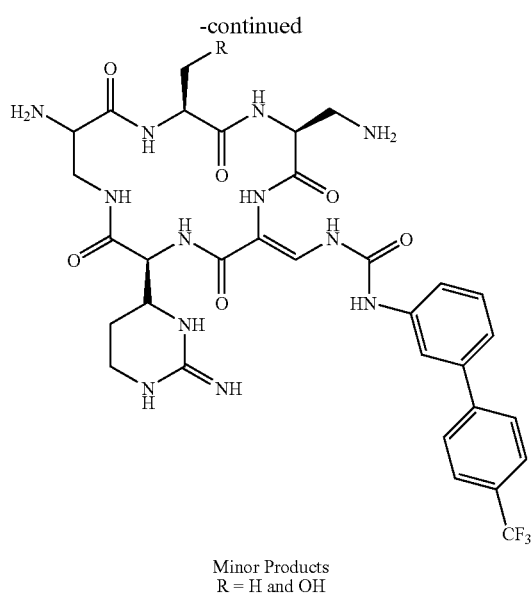

Minor Products
R = H and OH

Compound mixture 16 was prepared as an HCl salt according to the procedure outlined in Example 1, except that 3-aminobiphenyl is replaced with 4'-trifluoromethyl-3-aminobiphenyl (major products MH+=873.4, 889.3; minor products MH+=745.4, 761.3).

EXAMPLE 17

Preparation of Compound Mixture 17

17

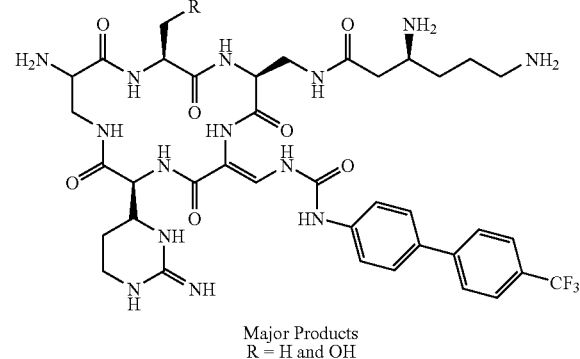

Major Products
R = H and OH

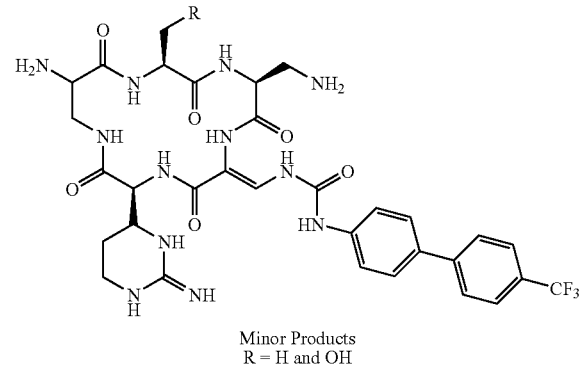

Minor Products
R = H and OH

Compound mixture 17 was prepared as an HCl salt according to the procedure outlined in Example 1, except that 3-aminobiphenyl is replaced with 4'-trifluoromethyl-4-aminobiphenyl (major products MH+=873.4, 889.4; minor products MH+=745.4, 761.3).

EXAMPLE 18

Preparation of Compound Mixture 18

18

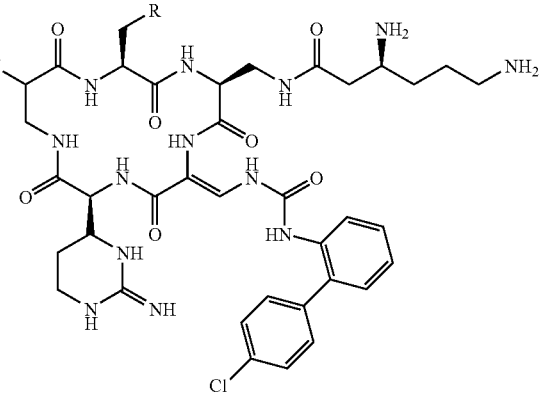

Major Products
R = H and OH

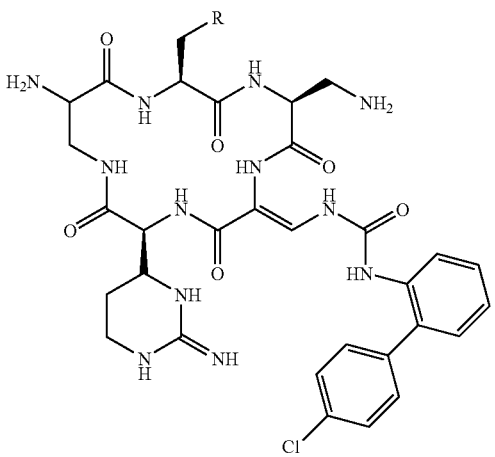

Minor Products
R = H and OH

Compound mixture 18 was prepared as an HCl salt according to the procedure outlined in Example 1, except that 3-aminobiphenyl is replaced with 4'-chloro-2-aminobiphenyl (major products MH+=839.4, 855.3; minor products MH+=711.3, 727.3).

EXAMPLE 19

Preparation of Compound Mixture 19

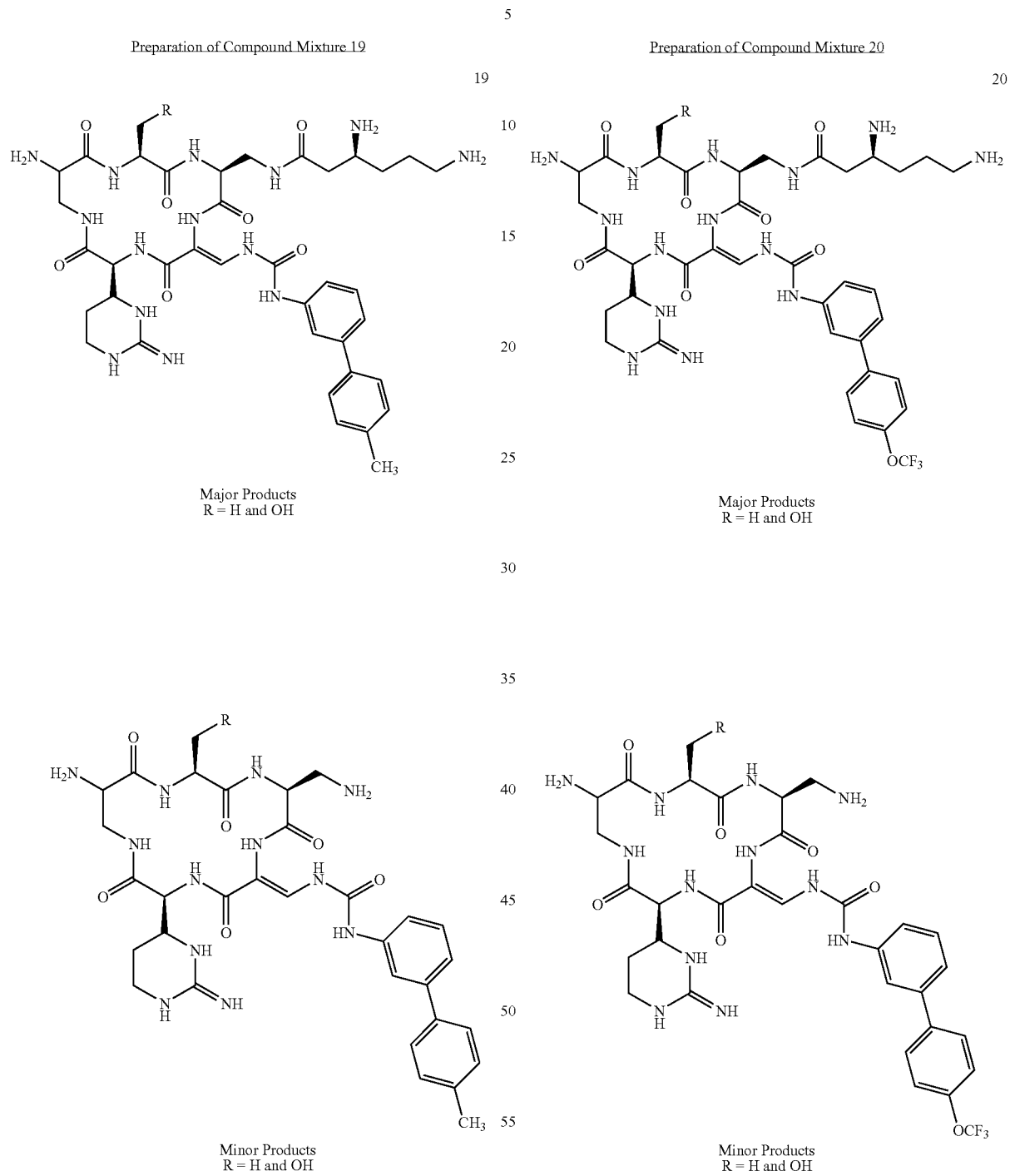

Compound mixture 19 was prepared as an HCl salt according to the procedure outlined in Example 1, except that 3-aminobiphenyl is replaced with 4'-methyl-3-aminobiphenyl (major products MH+=819.4, 835.4; minor products MH+=691.3, 707.3).

EXAMPLE 20

Preparation of Compound Mixture 20

Compound mixture 20 was prepared as an HCl salt according to the procedure outlined in Example 1, except that 3-aminobiphenyl is replaced with 4'-trifluoromethoxy-3-aminobiphenyl (major products MH+=889.4, 905.3; minor products MH+=761.3, 777.3).

EXAMPLE 21

Preparation of Compound Mixture 21

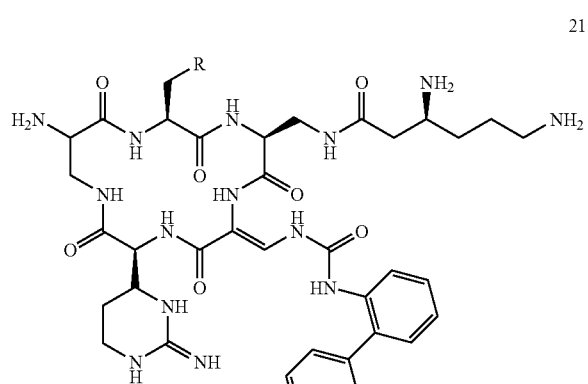

Major Products
R = H and OH

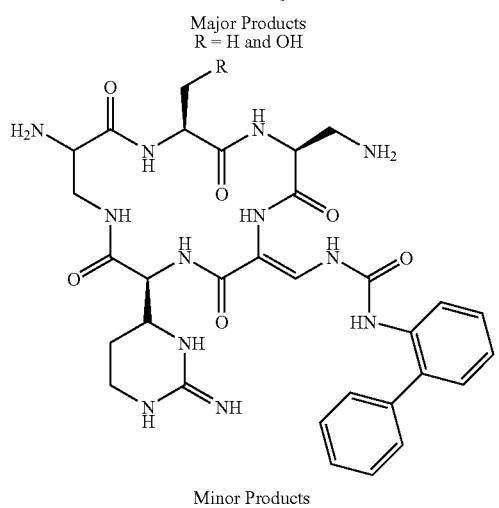

Minor Products
R = H and OH

Compound mixture 21 was prepared as an HCl salt according to the procedure outlined in Example 1, except that 3-aminobiphenyl is replaced with 2-aminobiphenyl (major products MH+=805.4, 821.4; minor products MH+=677.3, 693.3).

EXAMPLE 22

Preparation of Compound Mixture 22

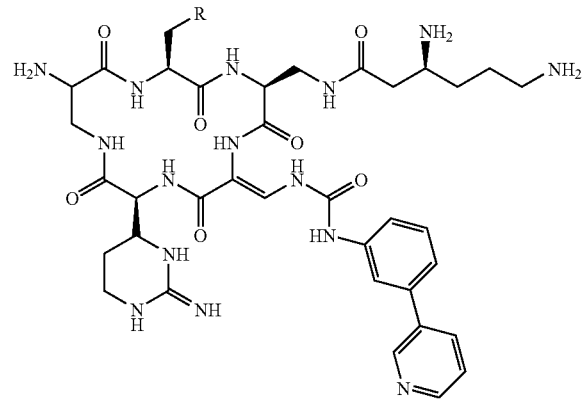

Major Products
R = H and OH

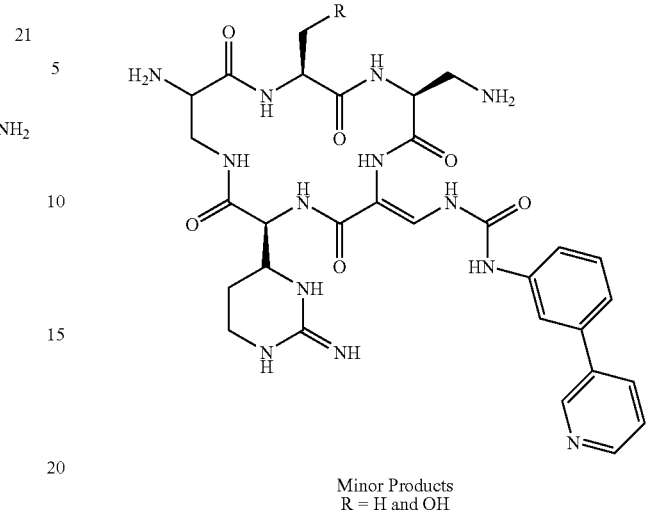

Minor Products
R = H and OH

Compound mixture 22 was prepared as an HCl salt according to the procedure outlined in Example 2, except that 2-thiopheneboronic acid is replaced with pyridine-3-boronic acid (major products MH+=806.4, 822.4).

EXAMPLE 23

Preparation of Compound Mixture 23

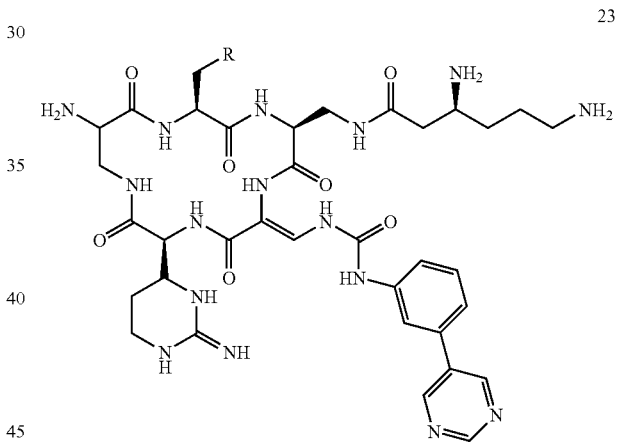

Major Products
R = H and OH

Minor Products
R = H and OH

Compound mixture 23 was prepared as an HCl salt according to the procedure outlined in Example 2, except that 2-thiopheneboronic acid is replaced with pyrimidine-5-boronic acid (major products MH+=807.4, 823.4).

EXAMPLE 24

Preparation of Compound Mixture 24

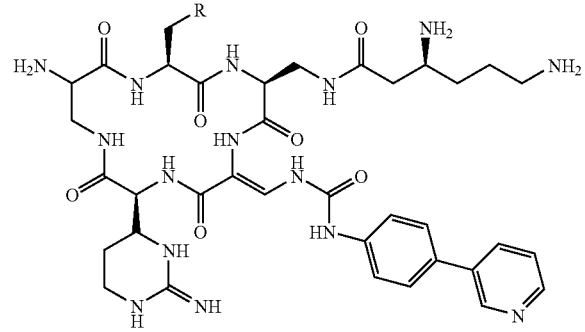

Major Products
R = H and OH

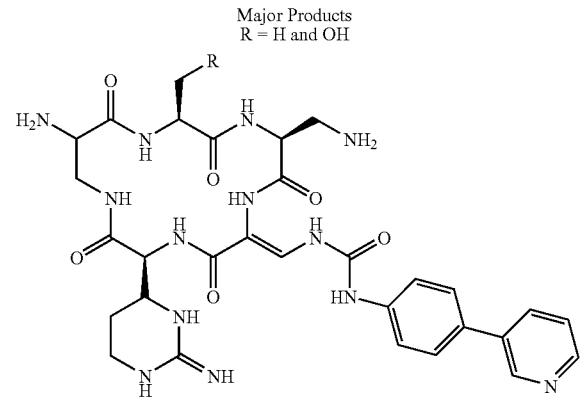

Minor Products
R = H and OH

Compound mixture 24 was prepared as an HCl salt according to the procedure outlined in Example 2, except that 2-thiopheneboronic acid is replaced with pyridine-3-boronic acid and 3-bromopheylurea is replaced by 4-bromopheylurea (major products MH+=806.4, 822.4).

EXAMPLE 25

Preparation of Compound Mixture 25

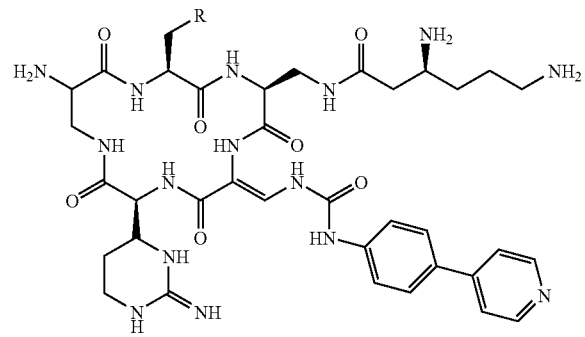

Major Products
R = H and OH

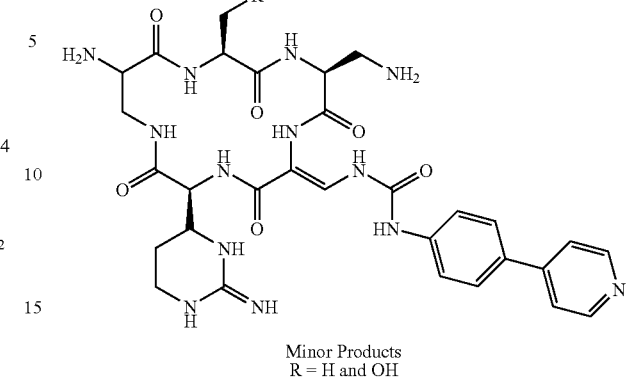

Minor Products
R = H and OH

Compound mixture 25 was prepared as an HCl salt according to the procedure outlined in Example 2, except that 2-thiopheneboronic acid is replaced with pyridine-4-boronic acid and 3-bromopheylurea is replaced by 4-bromopheylurea (major products MH+=806.4, 822.4).

EXAMPLE 26

Preparation of Compound Mixture 26

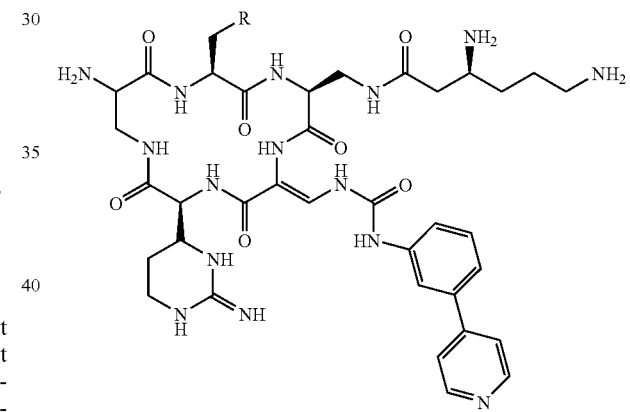

Major Products
R = H and OH

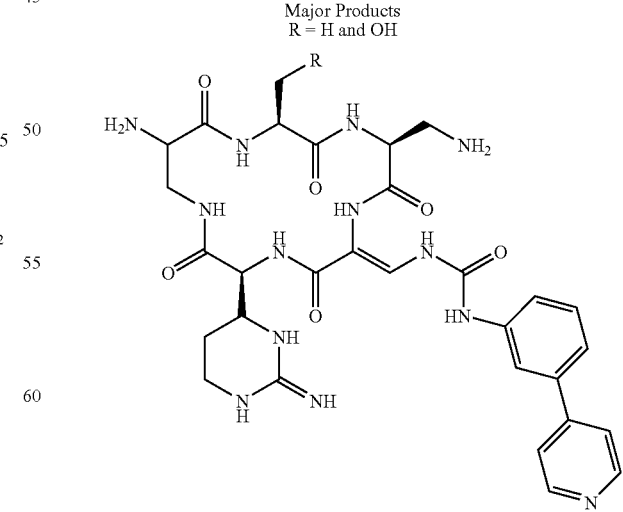

Minor Products
R = H and OH

Compound mixture 26 was prepared as an HCl salt according to the procedure outlined in Example 2, except that 2-thiopheneboronic acid is replaced with pyridine-4-boronic acid (major products MH+=806.4, 822.4).

EXAMPLE 27

Preparation of Compound Mixture 27

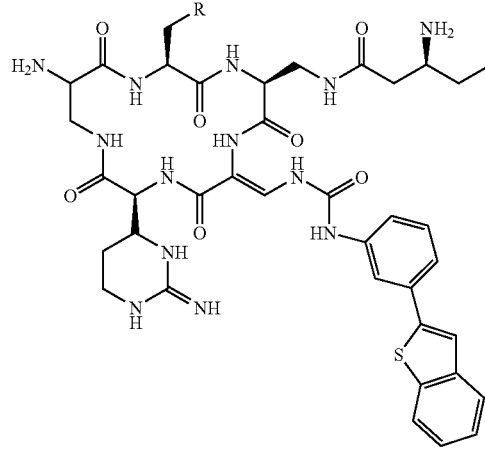

Major Products
R = H and OH

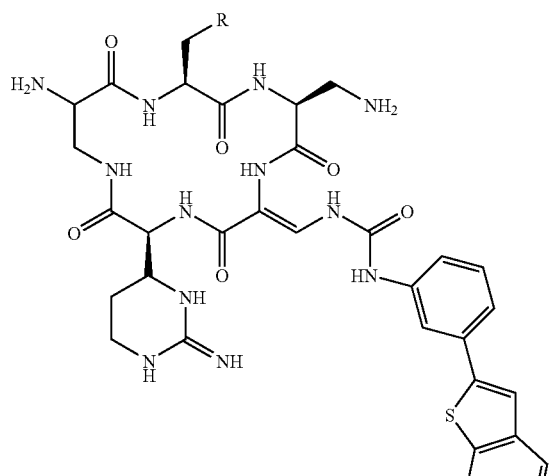

Minor Products
R = H and OH

Compound mixture 27 was prepared as an HCl salt according to the procedure outlined in Example 2, except that 2-thiopheneboronic acid is replaced with benzothiophene-2-boronic acid (major products MH+=861.4, 877.3).

EXAMPLE 28

Preparation of Compound Mixture 28

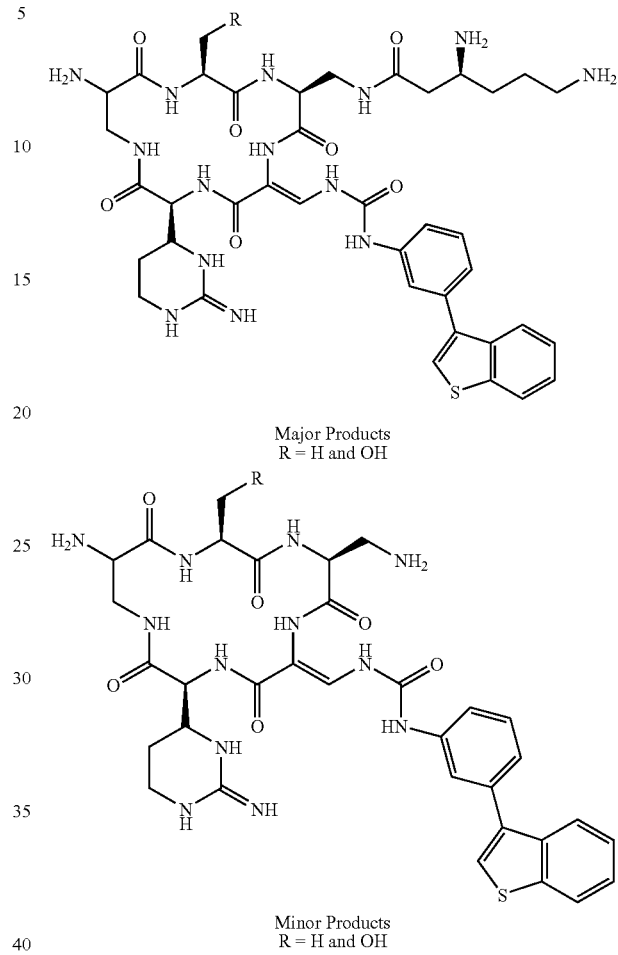

Major Products
R = H and OH

Minor Products
R = H and OH

Compound mixture 28 was prepared as an HCl salt according to the procedure outlined in Example 2, except that 2-thiopheneboronic acid is replaced with benzothiophene-3-boronic acid (major products MH+=861.4, 877.3).

EXAMPLE 29

Preparation of Compound Mixture 29

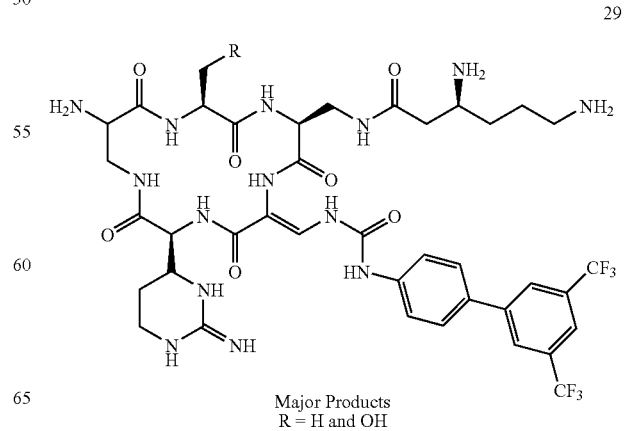

Major Products
R = H and OH

-continued

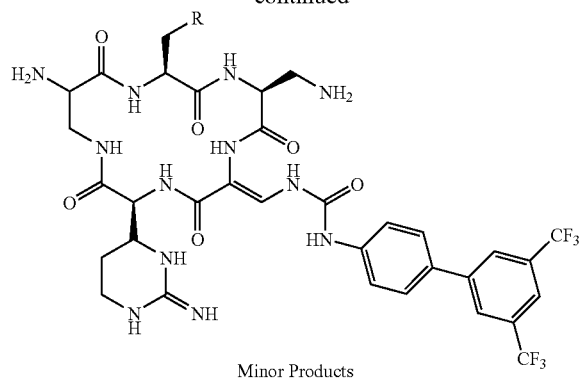

Minor Products
R = H and OH

Compound mixture 29 was prepared as an HCl salt according to the procedure outlined in Example 1, except that 3-aminobiphenyl is replaced with 3',5'-bis-trifluoromethoxy-4-aminobiphenyl (major products MH+=941.4, 957.3).

EXAMPLE 30

Preparation of Compound Mixture 30

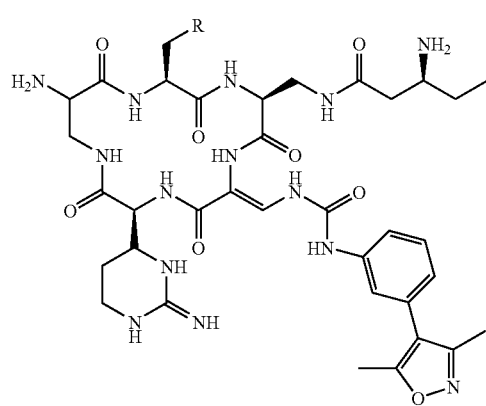

Major Products
R = H and OH

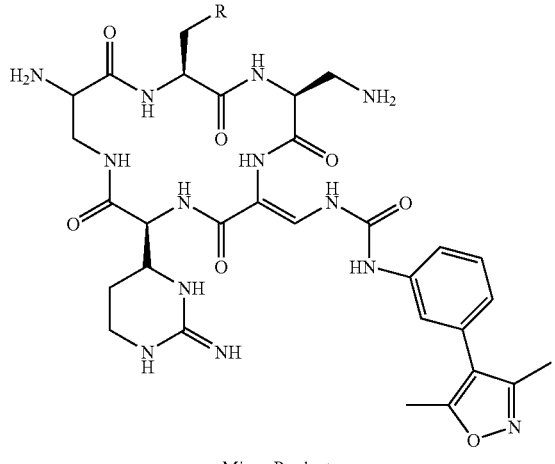

Minor Products
R = H and OH

Compound mixture 30 was prepared as an HCl salt according to the procedure outlined in Example 2, except that 2-thiopheneboronic acid is replaced with 3,5-dimethyl-isoxazol-4-ylboronic acid (major products MH+=824.4, 840.4).

EXAMPLE 31

Preparation of Compound Mixture 31

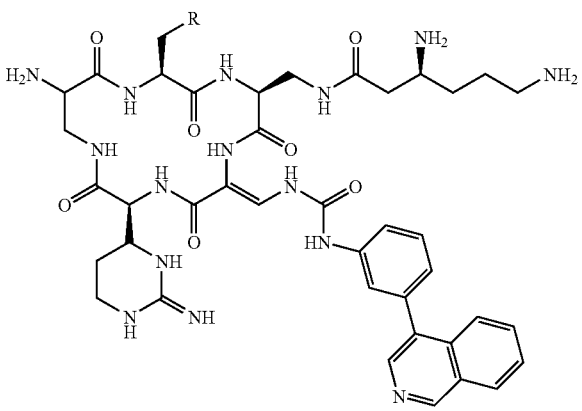

Major Products
R = H and OH

Minor Products
R = H and OH

Compound mixture 31 was prepared as an HCl salt according to the procedure outlined in Example 2, except that 2-thiopheneboronic acid is replaced with isoquinolin-4-ylboronic acid (major products MH+=856.4, 872.3).

EXAMPLE 32

Preparation of Compound Mixture 32

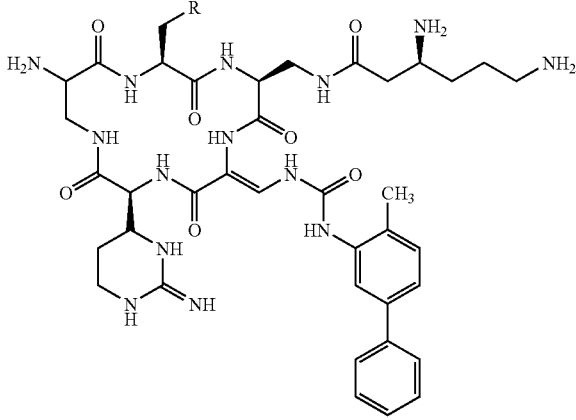

Major Products
R = H and OH

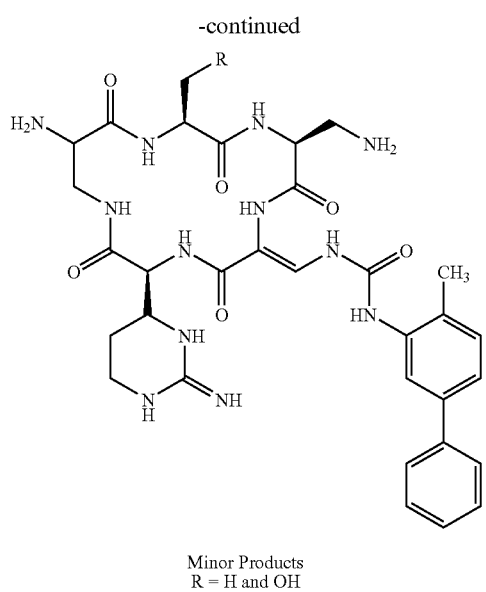

Minor Products
R = H and OH

Compound mixture 32 was prepared as an HCl salt according to the procedure outlined in Example 1, except that 3-aminobiphenyl is replaced with 4-methyl-3-aminobiphenyl (major products MH+=819.5, 835.4).

EXAMPLE 33

Preparation of Compound Mixture 33

33

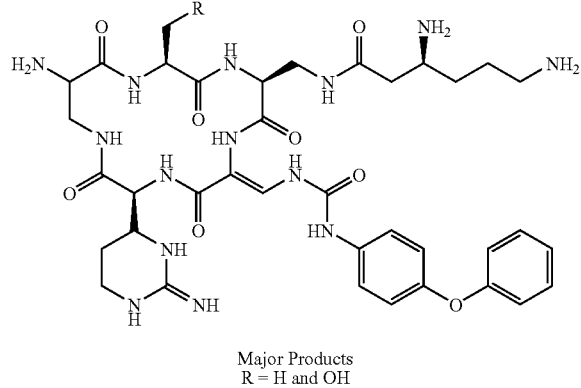

Major Products
R = H and OH

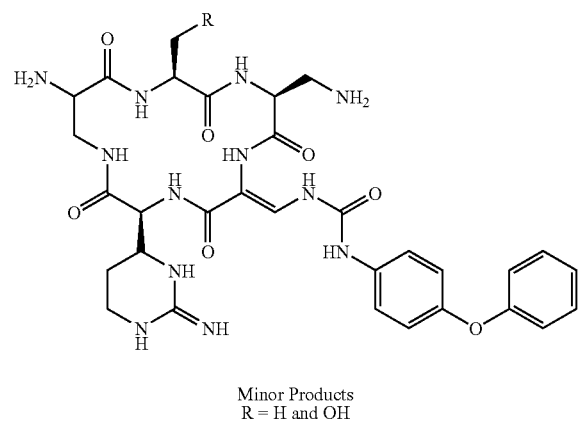

Minor Products
R = H and OH

Compound mixture 33 was prepared as an HCl salt according to the procedure outlined in Example 1, except that 3-aminobiphenyl is replaced with 4-phenoxyaniline (major products MH+=821.4, 837.3).

EXAMPLE 34

Preparation of Compound Mixture 34

34

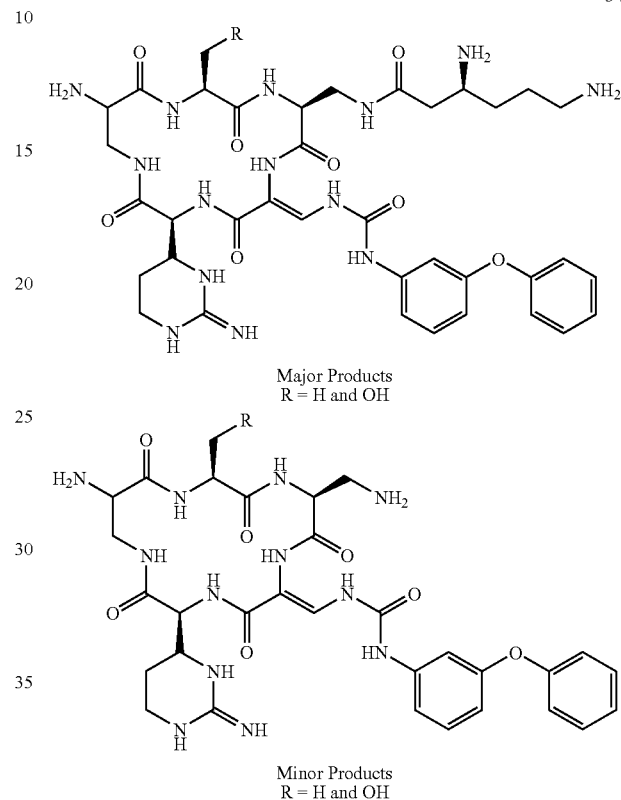

Major Products
R = H and OH

Minor Products
R = H and OH

Compound mixture 34 was prepared as an HCl salt according to the procedure outlined in Example 1, except that 3-aminobiphenyl is replaced with 3-phenoxyaniline (major products MH+=821.4, 837.3).

EXAMPLE 35

Preparation of Compound Mixture 35

35

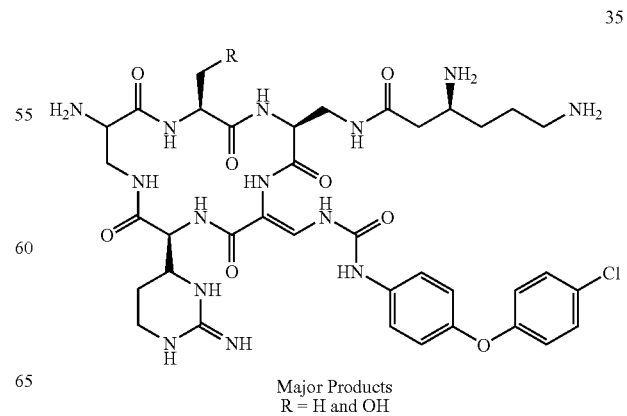

Major Products
R = H and OH

-continued

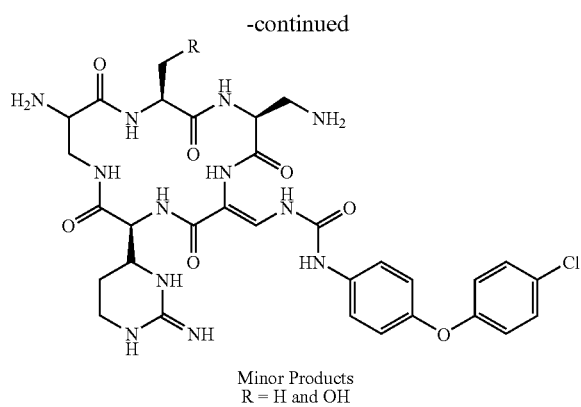

Minor Products
R = H and OH

Compound mixture 35 was prepared as an HCl salt according to the procedure outlined in Example 1, except that 3-aminobiphenyl is replaced with 4-(4-chlorophenoxy)-aniline (major products MH+=855.4, 873.3).

EXAMPLE 36

Preparation of Compound Mixture 36

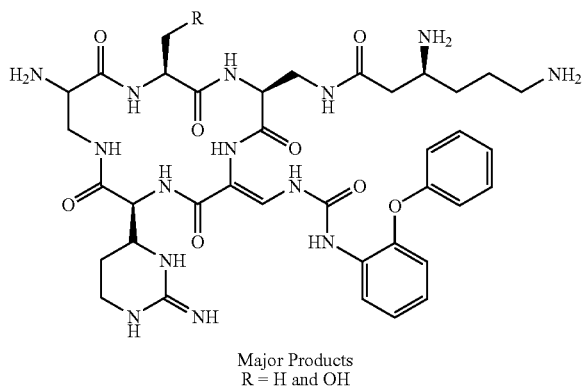

Major Products
R = H and OH

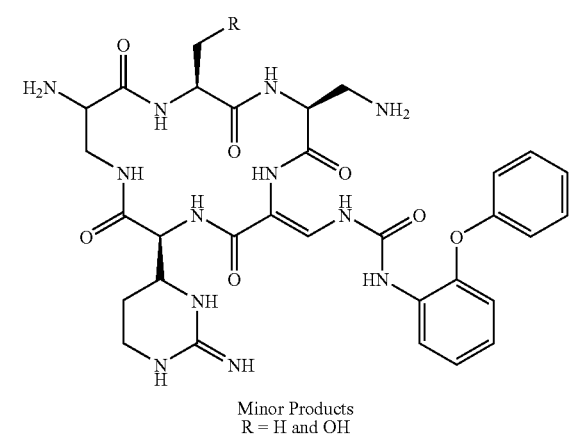

Minor Products
R = H and OH

Compound mixture 36 was prepared as an HCl salt according to the procedure outlined in Example 1, except that 3-aminobiphenyl is replaced with 2-phenoxyaniline (major products MH+=821.4, 837.3).

EXAMPLE 37

Preparation of Compound Mixture 37

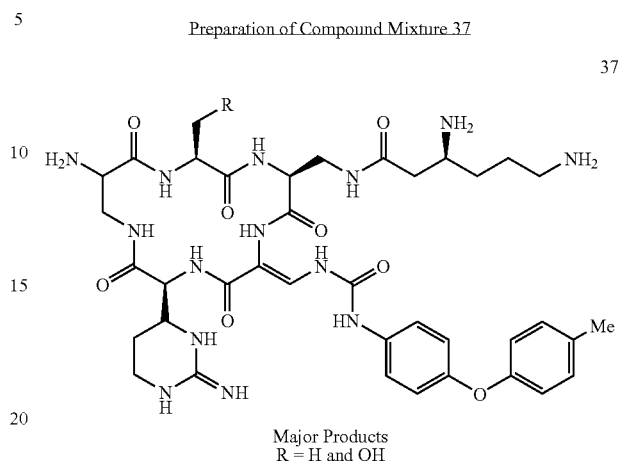

Major Products
R = H and OH

Minor Products
R = H and OH

Compound mixture 37 was prepared as an HCl salt according to the procedure outlined in Example 1, except that 3-aminobiphenyl is replaced with 4-(4-methylphenoxy)-aniline (major products MH+=835.4, 851.4).

EXAMPLE 38

Preparation of Compound Mixture 38

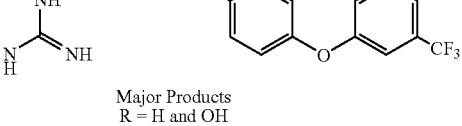

Major Products
R = H and OH

-continued

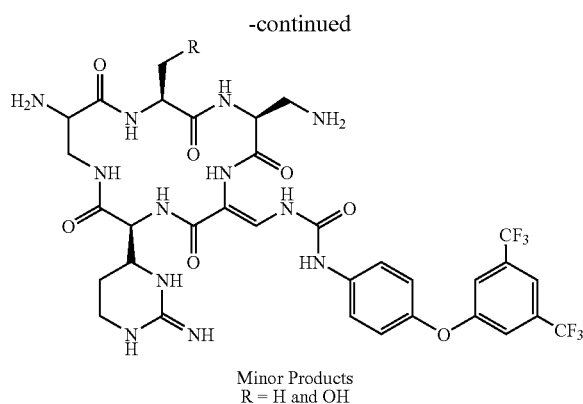

Minor Products
R = H and OH

Compound mixture 38 was prepared as an HCl salt according to the procedure outlined in Example 1, except that 3-aminobiphenyl is replaced with 4-(3,5-bis-trifluoromethylphenoxy)-aniline (major products MH+=957.4, 973.3).

EXAMPLE 39

Preparation of Compound Mixture 39

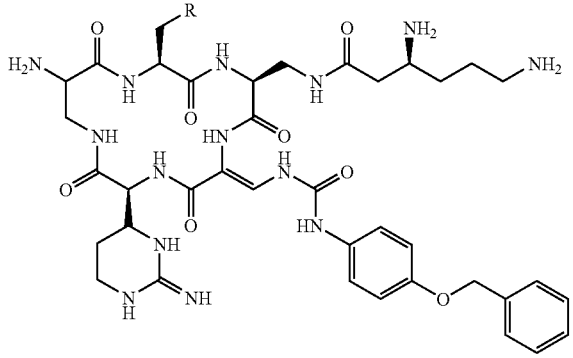

Major Products
R = H and OH

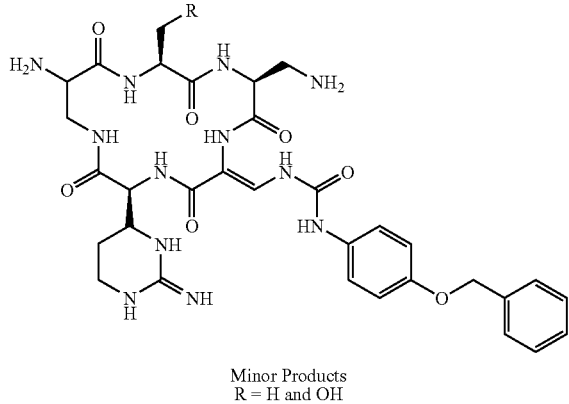

Minor Products
R = H and OH

Compound mixture 39 was prepared as an HCl salt according to the procedure outlined in Example 1, except that 3-aminobiphenyl is replaced with 4-benzyloxyaniline (major products MH+=835.4, 851.3).

EXAMPLE 40

Preparation of Compound Mixture 40

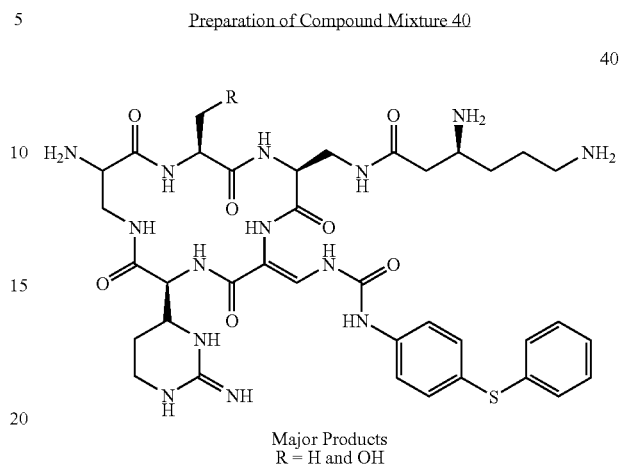

Major Products
R = H and OH

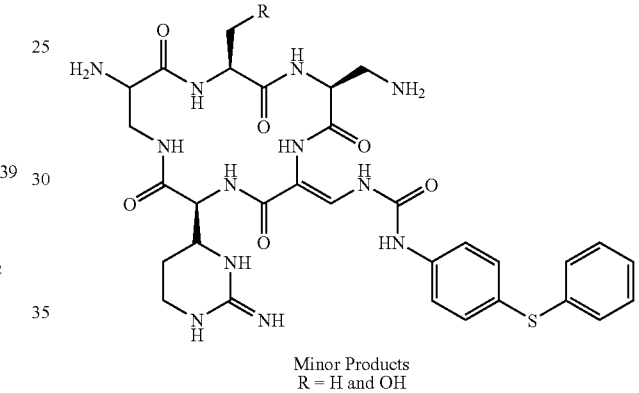

Minor Products
R = H and OH

Compound mixture 40 was prepared as an HCl salt according to the procedure outlined in Example 1, except that 3-aminobiphenyl is replaced with 4-(phenylthio)benzenamine (major products MH+=837.5, 853.5).

EXAMPLE 41

Preparation of Compound Mixture 41

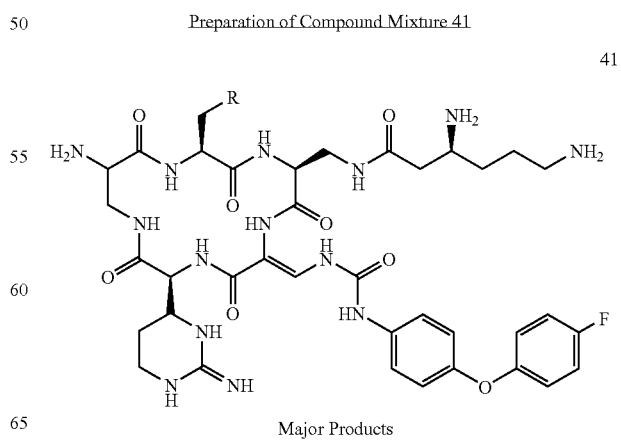

Major Products
R = H and OH

-continued

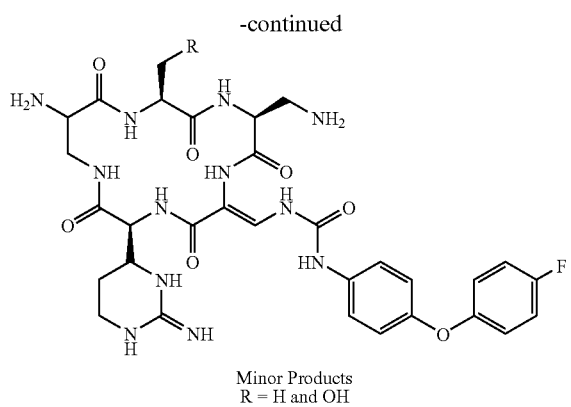

Minor Products
R = H and OH

Compound mixture 41 was prepared as an HCl salt according to the procedure outlined in Example 1, except that 3-aminobiphenyl is replaced with 4-(4-fluorophenoxy)-aniline (major products MH+=839.5, 855.5).

EXAMPLE 42

Preparation of Compound Mixture 42

42

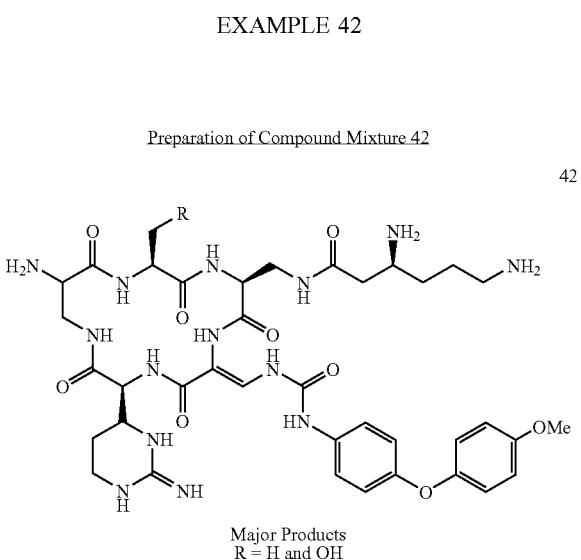

Major Products
R = H and OH

Minor Products
R = H and OH

Compound mixture 42 was prepared as an HCl salt according to the procedure outlined in Example 1, except that 3-aminobiphenyl is replaced with 4-(4-methoxyphenoxy)-aniline (major products MH+=851.6, 867.5).

EXAMPLE 43

Preparation of Compound Mixture 43

43

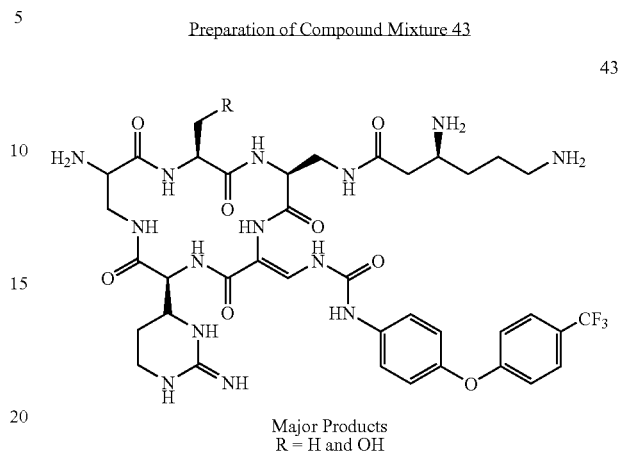

Major Products
R = H and OH

Minor Products
R = H and OH

Compound mixture 43 was prepared as an HCl salt according to the procedure outlined in Example 1, except that 3-aminobiphenyl is replaced with 4-(4-trifluoromethoxyphenoxy)-aniline (major products MH+=889.6, 905.5).

EXAMPLE 44

Preparation of Compound Mixture 44

44

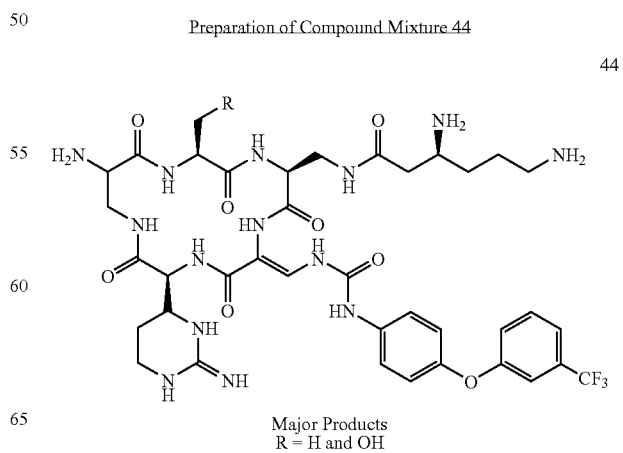

Major Products
R = H and OH

-continued

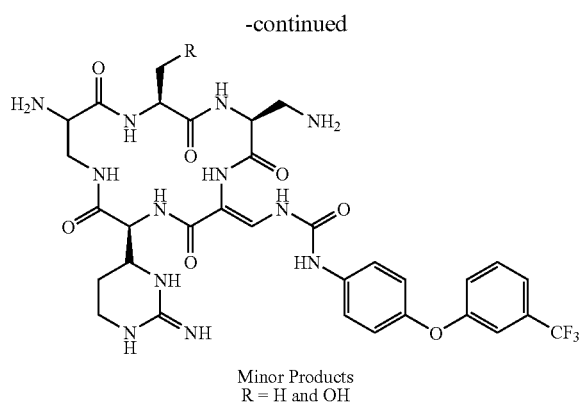

Minor Products
R = H and OH

Compound mixture 44 was prepared as an HCl salt according to the procedure outlined in Example 1, except that 3-aminobiphenyl is replaced with 4-(3-trifluoromethoxyphenoxy)-aniline (major products MH+=889.6, 905.4).

EXAMPLE 45

Preparation of Compound Mixture 45

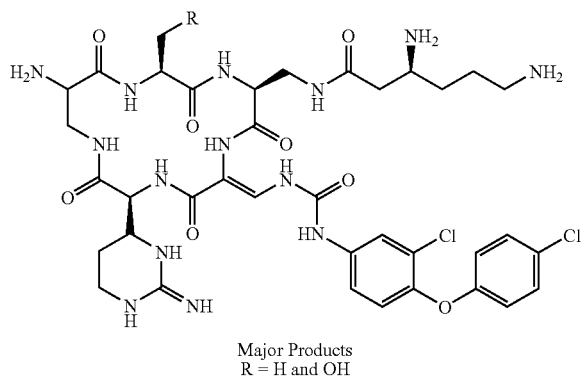

Major Products
R = H and OH

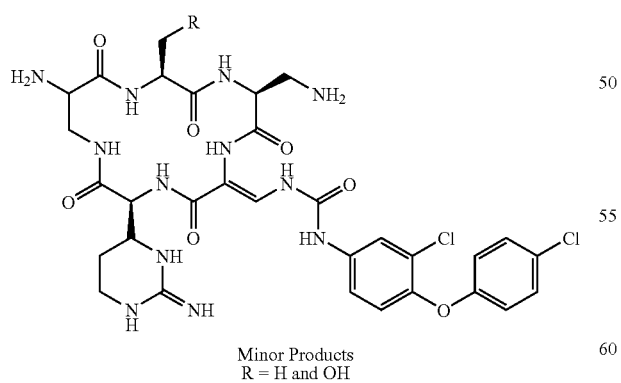

Minor Products
R = H and OH

Compound mixture 45 was prepared as an HCl salt according to the procedure outlined in Example 1, except that 3-aminobiphenyl is replaced with 3-chloro-4-(4-chlorophenoxy)-aniline (major products MH+=889.5, 905.4).

EXAMPLE 46

Preparation of Compound Mixture 46

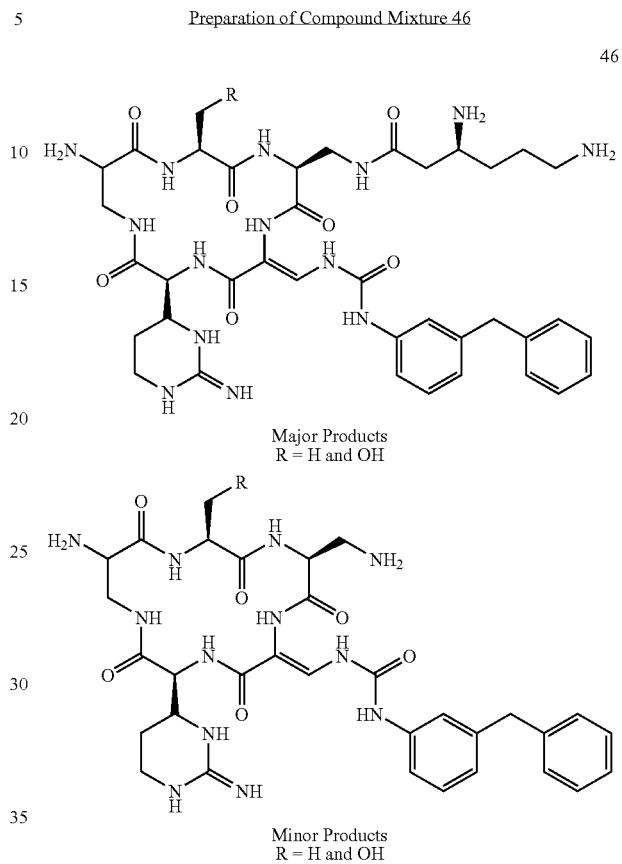

Major Products
R = H and OH

Minor Products
R = H and OH

Compound mixture 46 was prepared as an HCl salt according to the procedure outlined in Example 1, except that 3-aminobiphenyl is replaced with 3-benzylaniline (major products MH+=819.6, 835.6).

EXAMPLE 47

Preparation of Compound Mixture 47

Major Products
R = H and OH

-continued

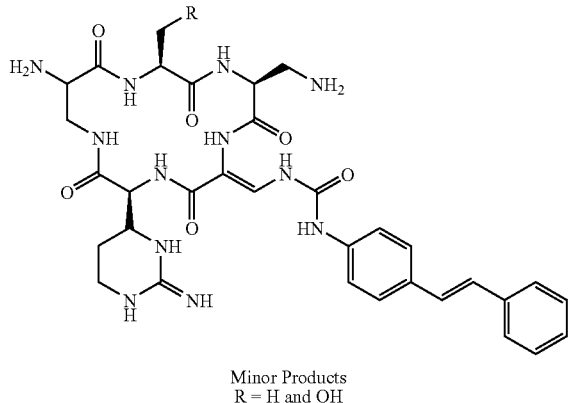

Minor Products
R = H and OH

Compound mixture 47 was prepared as an HCl salt according to the procedure outlined in Example 1, except that 3-aminobiphenyl is replaced with (E)-4-styrylbenzenamine (major products MH+=831.6, 847.6).

EXAMPLE 48

Preparation of Compound Mixture 48

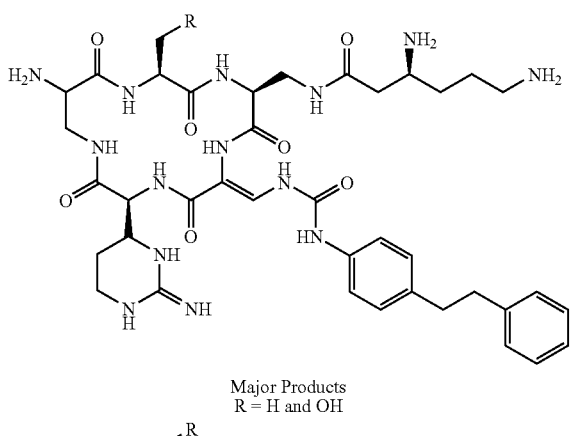

48

Major Products
R = H and OH

Minor Products
R = H and OH

Compound mixture 48 was prepared as an HCl salt according to the procedure outlined in Example 1, except that 3-aminobiphenyl is replaced with 4-phenethylbenzenamine (major products MH+=833.6, 849.6).

EXAMPLE 49

Preparation of Compound Mixture 49

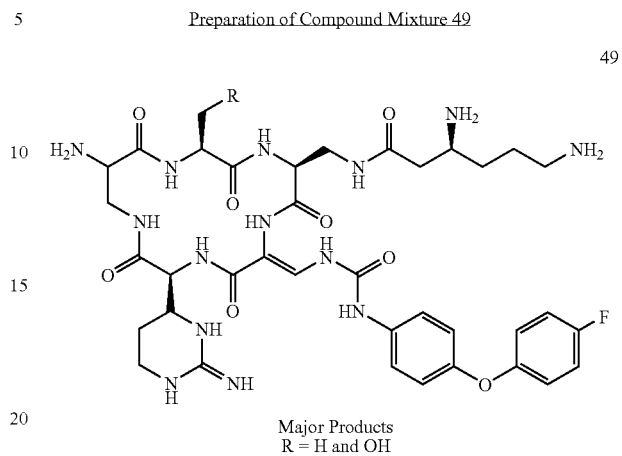

49

Major Products
R = H and OH

Minor Products
R = H and OH

Compound mixture 49 was prepared as an HCl salt according to the procedure outlined in Example 1, except that 3-aminobiphenyl is replaced with 4-(4-fluorophenoxy)-aniline (major products MH+=839.5, 855.5).

EXAMPLE 50

Preparation of Compound Mixture 50

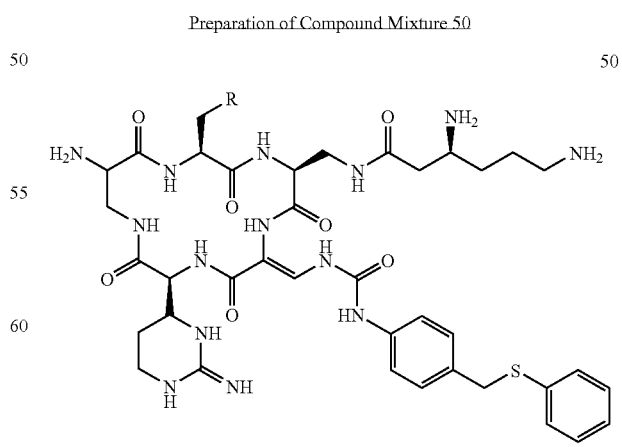

50

Major Products
R = H and OH

-continued

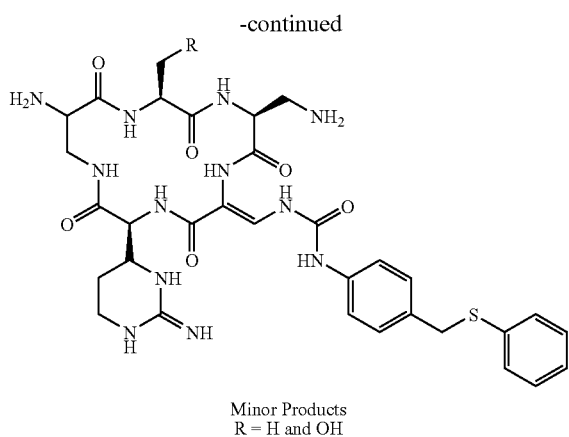

Minor Products
R = H and OH

Compound mixture 50 was prepared as an HCl salt according to the procedure outlined in Example 1, except that 3-aminobiphenyl is replaced with 4-(phenylthiomethyl)benzenamine (major products MH+=851.5, 867.4).

EXAMPLE 51

Preparation of Compound Mixture 51

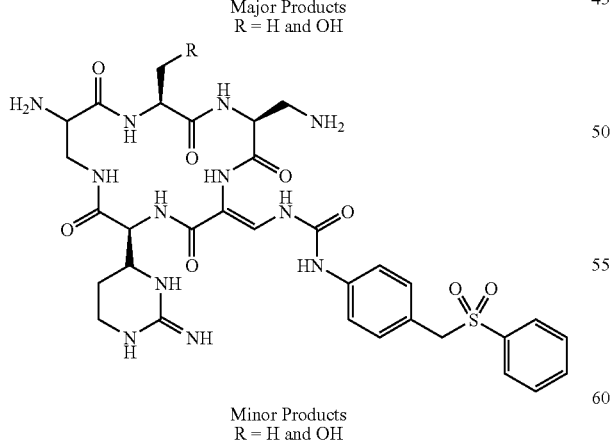

Major Products
R = H and OH

Minor Products
R = H and OH

Compound mixture 51 was prepared as an HCl salt according to the procedure outlined in Example 1, except that 3-aminobiphenyl is replaced with 4-(phenylsulfonylmethyl)benzenamine (major products MH+=883.5, 899.5).

EXAMPLE 52

Preparation of Compound Mixture 52

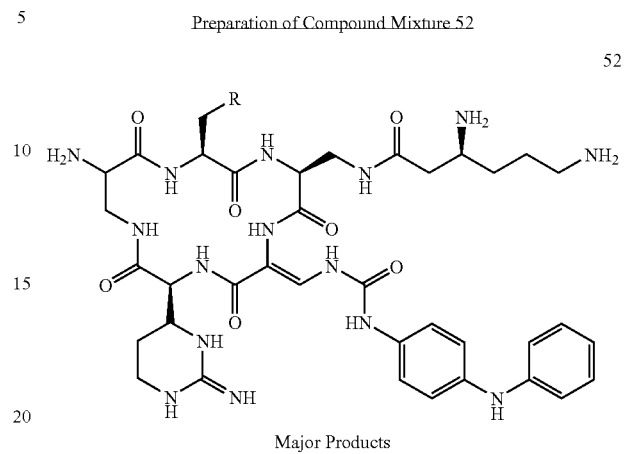

Major Products
R = H and OH

Minor Products
R = H and OH

Compound mixture 52 was prepared as an HCl salt according to the procedure outlined in Example 1, except that 3-aminobiphenyl is replaced with $N_1$-phenylbenzene-1,4-diamine (major products MH+=820.6, 836.6).

EXAMPLE 53

Preparation of Compound Mixture 53

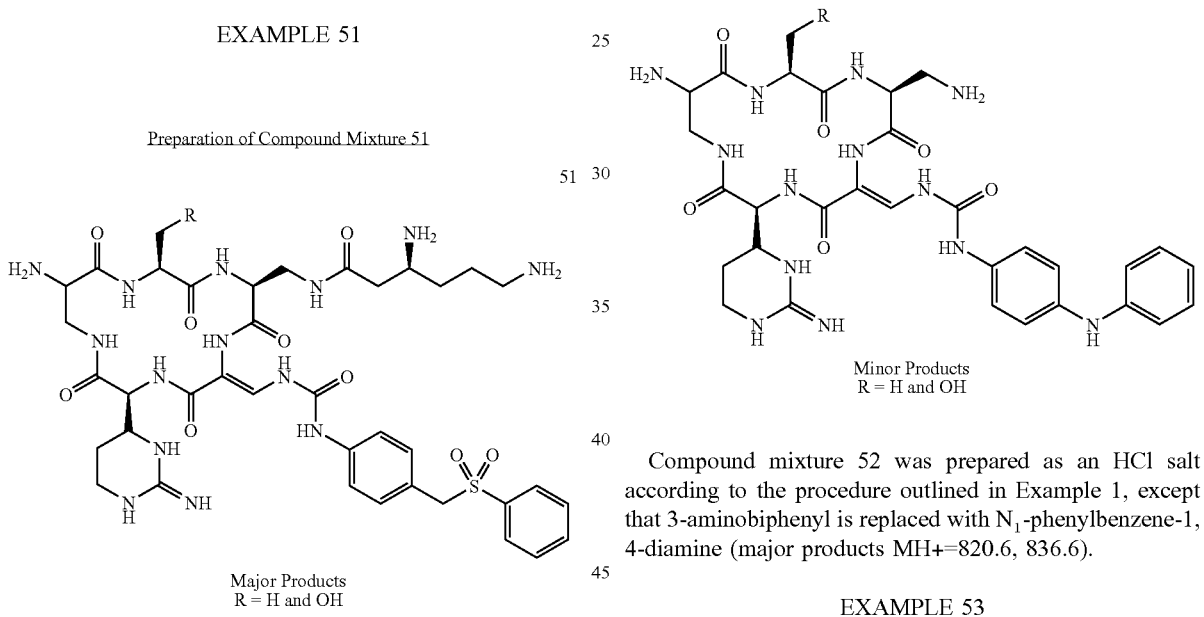

Major Products
R = H and OH

-continued

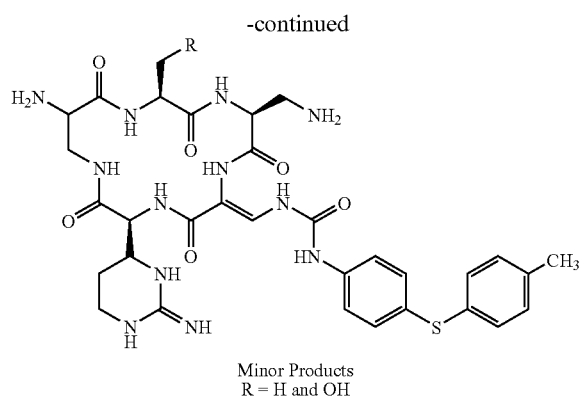

Minor Products
R = H and OH

Compound mixture 53 was prepared as an HCl salt according to the procedure outlined in Example 1, except that 3-aminobiphenyl is replaced with 4-(p-tolylthio)benzenamine (major products MH+=851.6, 867.5).

EXAMPLE 54

Preparation of Compound Mixture 54

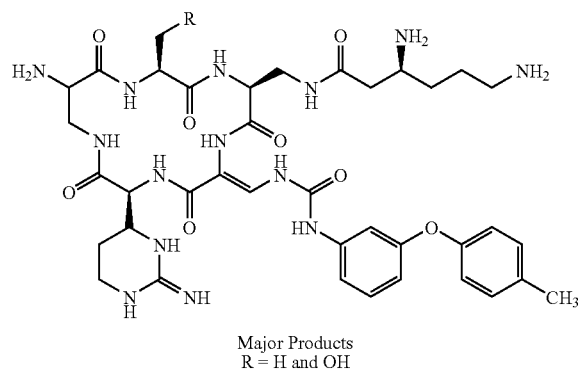

Major Products
R = H and OH

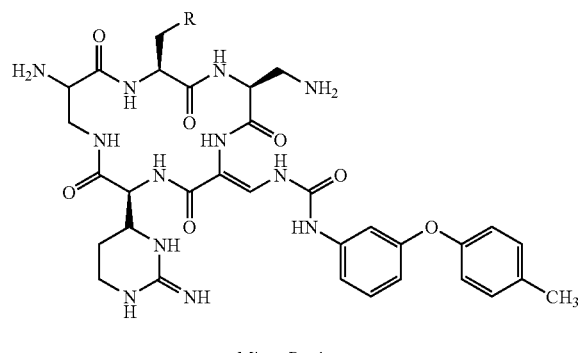

Minor Products
R = H and OH

Step A: 1-(3-Hydroxyphenyl)urea (2.00 g), p-tolylboronic acid (3.57 g), and Cu(OAc)$_2$ (2.63 g) were dissolved in 150 mL of THF, and 5.32 mL of pyridine was added. The reaction was stirred at room temperature overnight, then filtered through Celite with the aid of 200 mL EtOAc. The filtrate was washed with water, 0.2N CuSO$_4$, 0.5N NaOH, and brine, and dried over Na$_2$SO$_4$ The solution was concentrated to a solid that was taken up in 200 mL of dichloromethane and stirred at room temperature for about 1 hour, after which time it was filtered to give 1-(3-(p-tolyloxy) phenyl)urea as white solid. The material was used in Step B without further purification.

Step B: Capreomycin was reacted with 1-(3-(p-tolyloxy) phenyl)urea according to the procedure of Example 1 to give compound mixture 54 as an HCl salt (major products MH+=835.6, 851.5).

EXAMPLE 55

Preparation of Compound Mixture 55

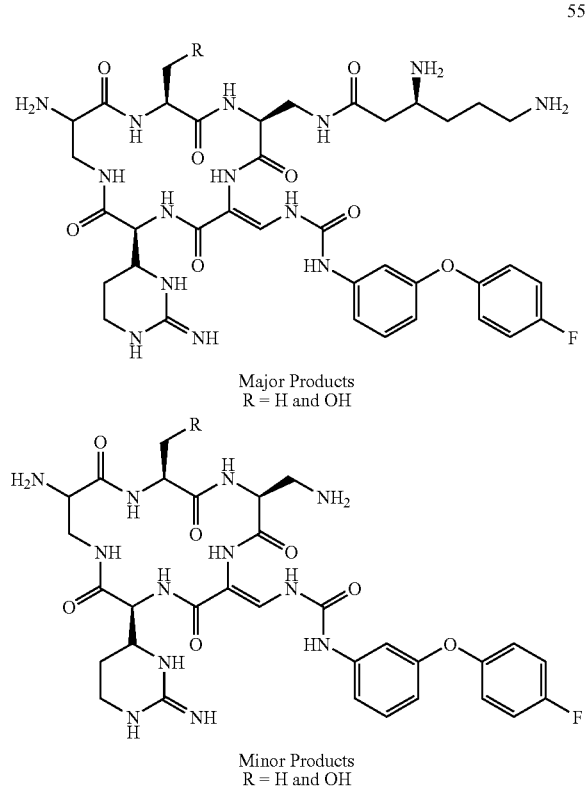

Major Products
R = H and OH

Minor Products
R = H and OH

Compound mixture 55 was prepared as an HCl salt according to the procedure of Example 54, except that p-tolylboronic acid was replaced with 4-fluorophenylboronic acid (major products MH+=839.6, 855.6).

EXAMPLE 56

Preparation of Compound Mixture 56

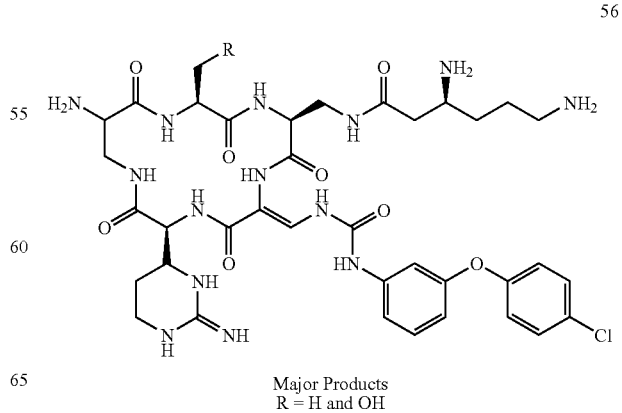

Major Products
R = H and OH

-continued

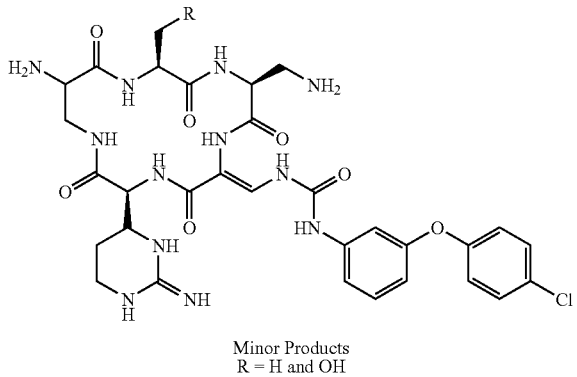

Minor Products
R = H and OH

Compound mixture 56 was prepared as an HCl salt according to the procedure of Example 54, except that p-tolylboronic acid was replaced with 4-chlorophenylboronic acid (major products MH+=855.6, 871.5).

EXAMPLE 57

Preparation of Compound Mixture 57

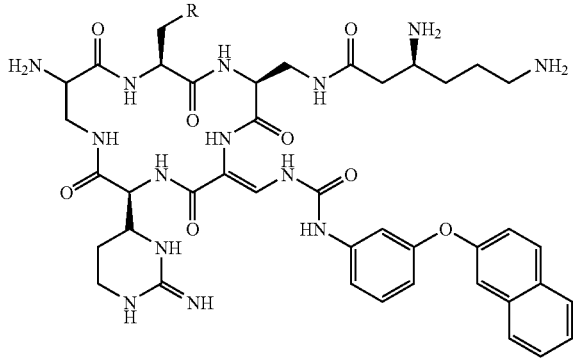

57

Major Products
R = H and OH

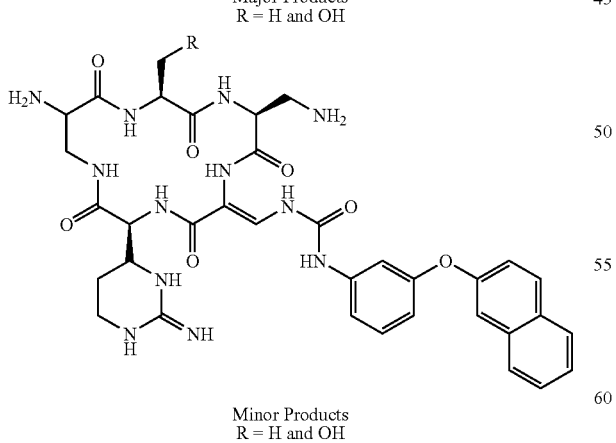

Minor Products
R = H and OH

Compound mixture 57 was prepared as an HCl salt according to the procedure of Example 54, except that p-tolylboronic acid was replaced with naphthalen-2-ylboronic acid (major products MH+=871.6, 887.5).

EXAMPLE 58

Preparation of Compound Mixture 58

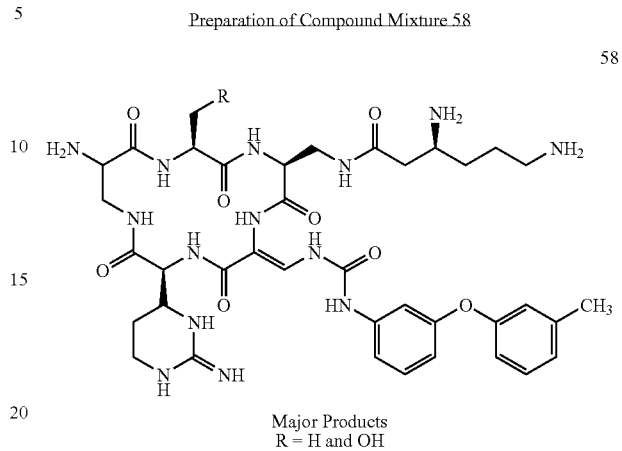

58

Major Products
R = H and OH

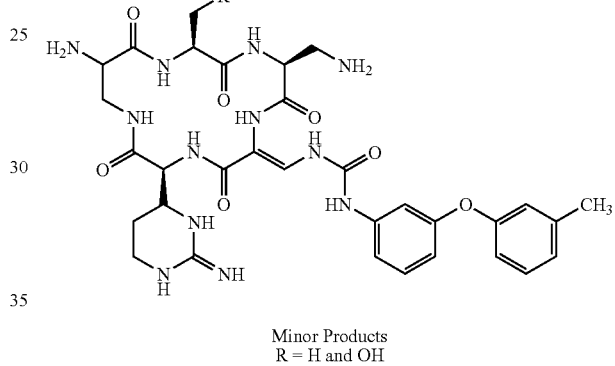

Minor Products
R = H and OH

Compound mixture 58 was prepared as an HCl salt according to the procedure of Example 54, except that p-tolylboronic acid was replaced with m-tolylboronic acid (major products MH+=835.6, 851.5).

EXAMPLE 59

Preparation of Compound Mixture 59

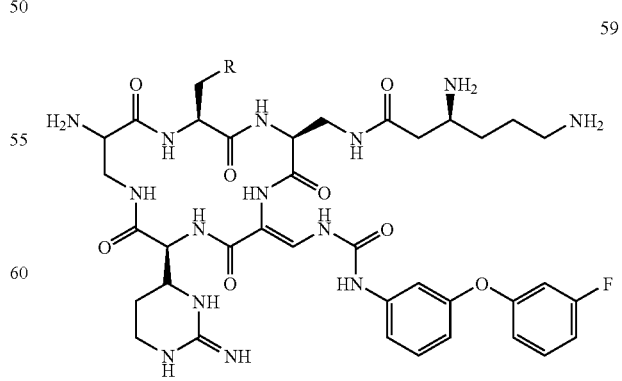

59

Major Products
R = H and OH

-continued

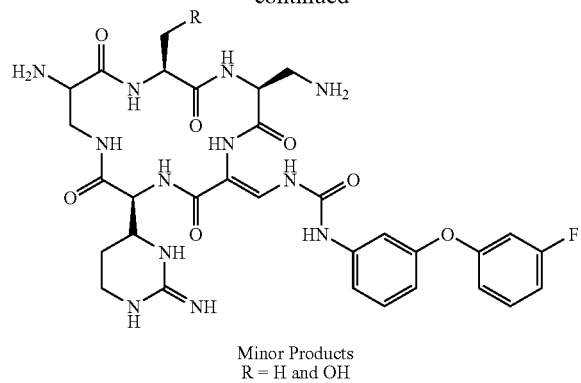

Minor Products
R = H and OH

Compound mixture 59 was prepared as an HCl salt according to the procedure of Example 54, except that p-tolylboronic acid was replaced with 3-fluorophenylboronic acid (major products MH+=839.5, 855.6).

EXAMPLE 60

Preparation of Compound Mixture 60

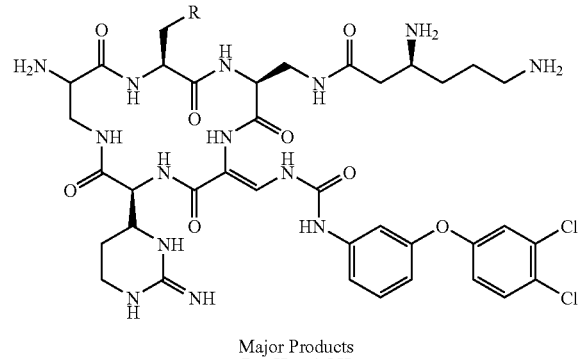

Major Products
R = H and OH

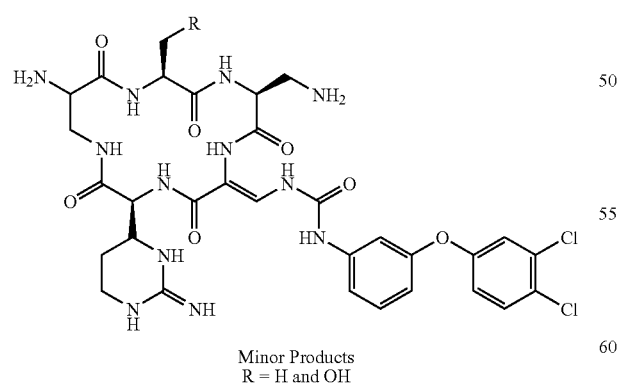

Minor Products
R = H and OH

Compound mixture 60 was prepared as an HCl salt according to the procedure of Example 54, except that p-tolylboronic acid was replaced with 3,4-dichlorophenylboronic acid (major products MH+=889.2, 905.3).

EXAMPLE 61

Preparation of Compound Mixture 61

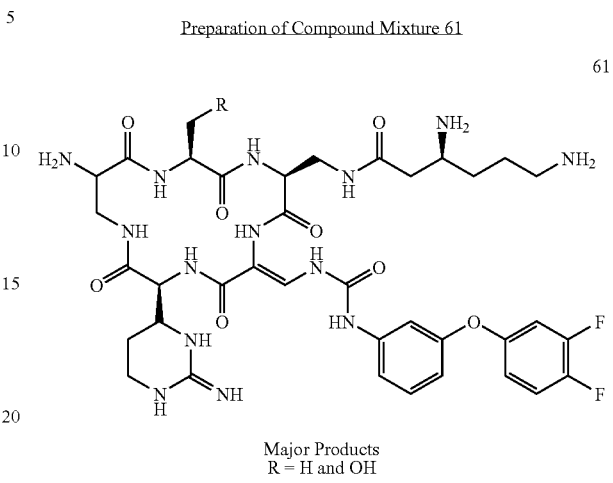

Major Products
R = H and OH

Minor Products
R = H and OH

Compound 61 was prepared as an HCl salt according to the procedure of Example 54, except that p-tolylboronic acid was replaced with 3,4-difluorophenylboronic acid (major products MH+=857.3, 873.2).

EXAMPLE 62

Preparation of Compound Mixture 62

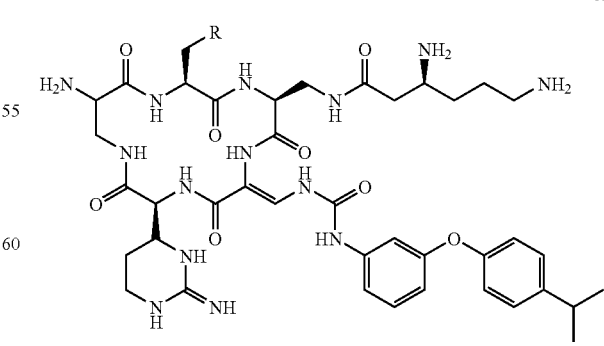

Major Products
R = H and OH

-continued

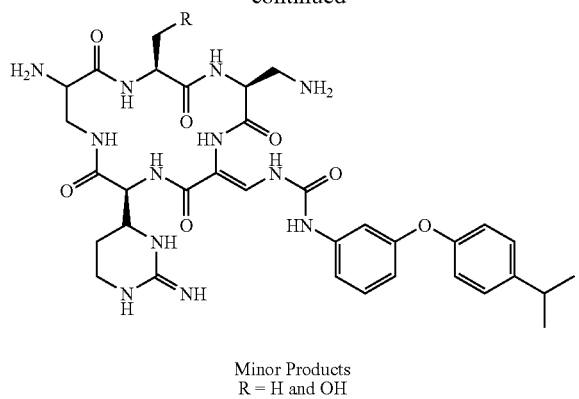

Minor Products
R = H and OH

Compound mixture 62 was prepared as an HCl salt according to the procedure of Example 54, except that p-tolylboronic acid was replaced with 4-isopropylphenylboronic acid (major products MH+=863.4, 879.3).

EXAMPLE 63

Preparation of Compound Mixture 63

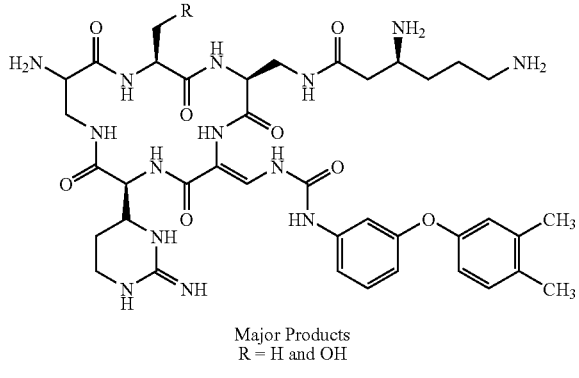

Major Products
R = H and OH

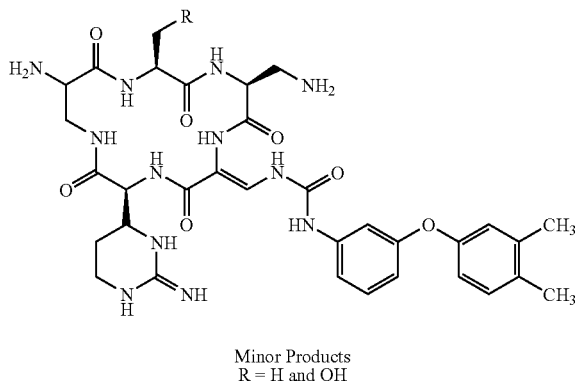

Minor Products
R = H and OH

Compound mixture 63 was prepared as an HCl salt according to the procedure of Example 54, except that p-tolylboronic acid was replaced with 3,4-dimethylphenylboronic acid (major products MH+=849.4, 865.3).

EXAMPLE 64

Preparation of Compound Mixture 64

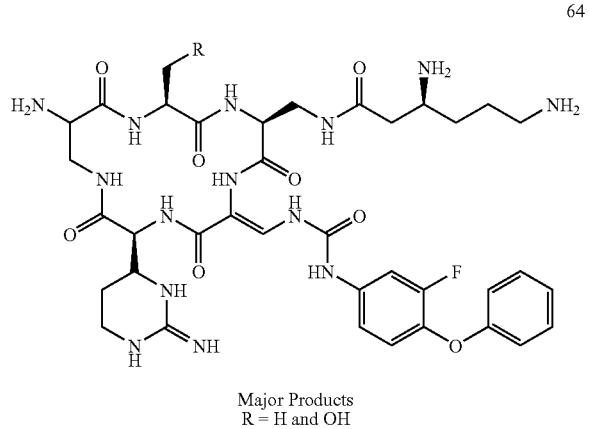

Major Products
R = H and OH

Minor Products
R = H and OH

Step A: 1,2-Difluoro-4-nitrobenzene (21.6 g) and phenol (14.0 g) were dissolved in 100 mL of DMF and cooled to 0° C. NaH (6.5 g) was added portionwise and the reaction mixture was stirred at room temperature overnight. The reaction mixture was taken up in EtOAc and washed with water and brine, and dried over $Na_2SO_4$. The solution was concentrated to provide 2-fluoro-4-nitro-1-phenoxybenzene as an oil, which was used in Step B without further purification.

Step B: 2-Fluoro-4-nitro-1-phenoxybenzene and 7.2 g of 10% Pd/C were dissolved in 200 mL EtOH and stirred under 1 atmosphere of $H_2$ overnight. The reaction mixture was filtered through Celite with the aid of 50 mL EtOH and concentrated to provide 3-fluoro-4-phenoxybenzenamine as an oil which was used in Step C without further purification.

Step C: Compound mixture 64 was prepared as an HCl salt according to the procedure of Example 1, except that 3-aminobiphenyl was replaced with 3-fluoro-4-phenoxybenzenamine (major products MH+=839.3, 855.3).

EXAMPLE 65

Preparation of Compound Mixture 65

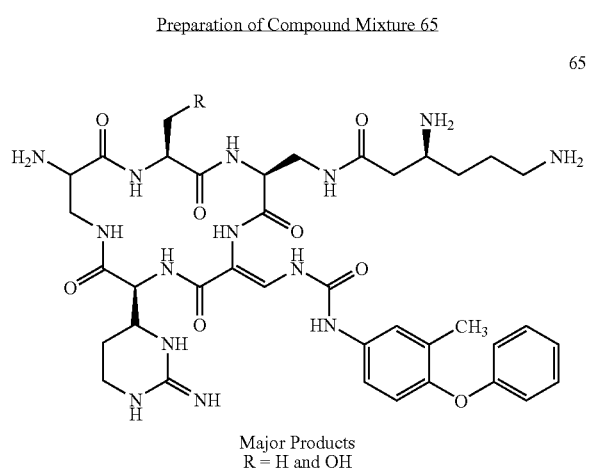

Major Products
R = H and OH

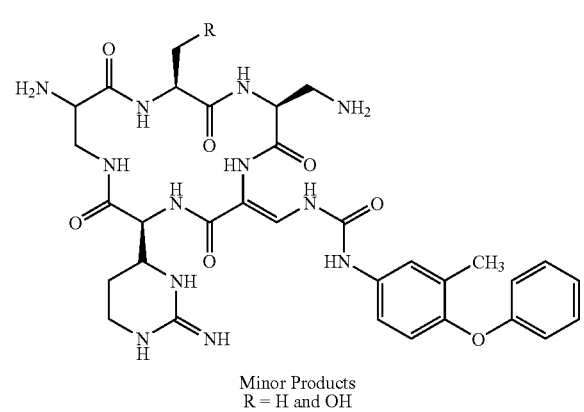

Minor Products
R = H and OH

Step A: 1-Fluoro-2-methyl-4-nitrobenzene (9.75 g), phenol (7.10 g), and of $Cs_2CO_3$ (41.0 g) were dissolved in 100 mL of DMF and heated to 120° C. overnight. The reaction mixture was taken up in EtOAc and washed with water and brine, and dried over $Na_2SO_4$. The solution was concentrated to provide 2-methyl-4-nitro-1-phenoxybenzene as an oil, which was used in Step B without further purification.

Step B: 2-Methyl-4-nitro-1-phenoxybenzene and 10% Pd/C (3.35 g) were dissolved in 200 mL EtOH and stirred under 1 atmosphere of $H_2$ overnight. The reaction mixture was filtered through Celite with the aid of 50 mL EtOH and concentrated to provide 3-methyl-4-phenoxybenzenamine as an oil, which was used in Step C without further purification.

Step C: Compound mixture 65 was prepared as an HCl salt according to the procedure of Example 1, except that 3-aminobiphenyl was replaced with 3-methyl-4-phenoxybenzenamine (major products MH+=835.3, 851.3).

EXAMPLE 66

Preparation of Compound Mixture 66

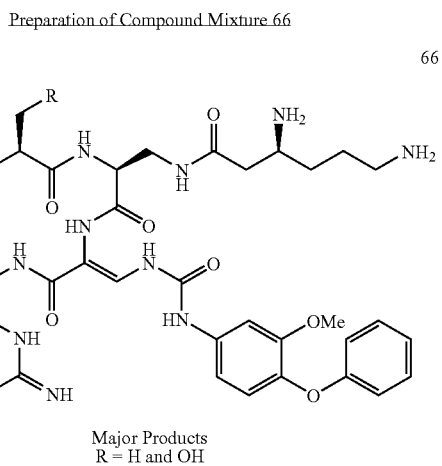

Major Products
R = H and OH

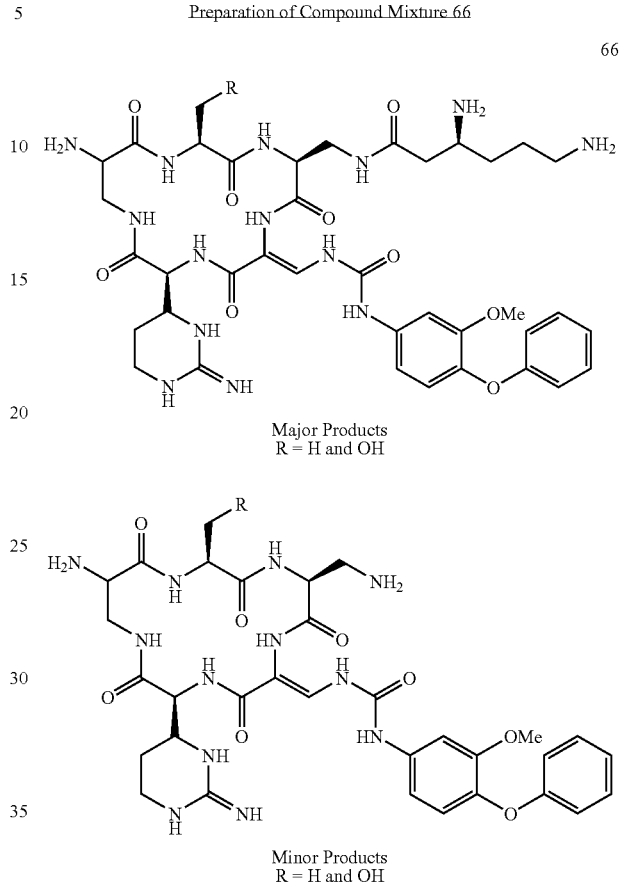

Minor Products
R = H and OH

Compound mixture 66 was prepared as an HCl salt according to the procedure of Example 65, except that 1-fluoro-2-methyl-4-nitrobenzene was replaced with 1-chloro-2-methoxy-4-nitrobenzene (major products MH+=851.3, 867.3).

EXAMPLE 67

Preparation of Compound Mixture 67

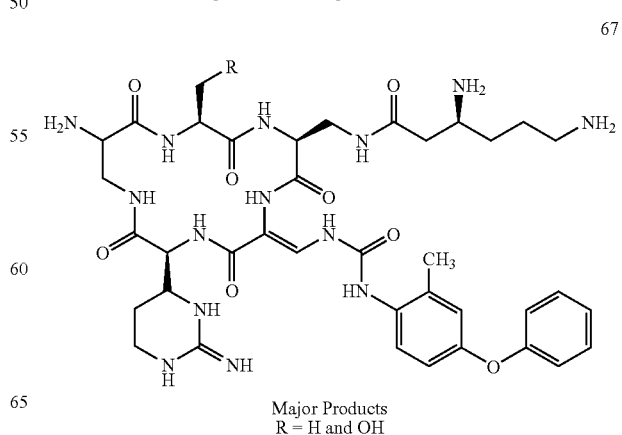

Major Products
R = H and OH

81

-continued

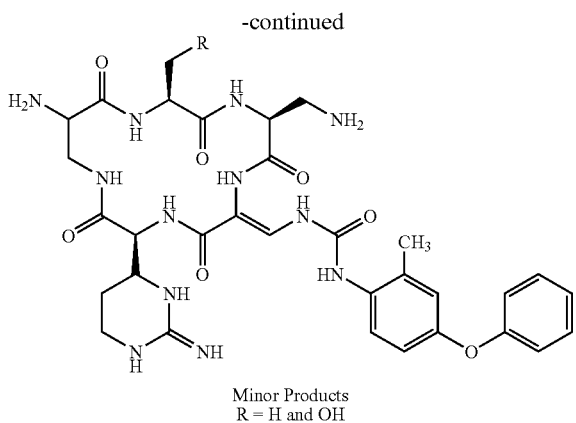

Minor Products
R = H and OH

Compound mixture 67 was prepared as an HCl salt according to the procedure of Example 65, except that 1-fluoro-2-methyl-4-nitrobenzene was replaced with 4-fluoro-2-methyl-1-nitrobenzene (major products MH+=835.4, 851.3).

EXAMPLE 68

Preparation of Compound Mixture 68

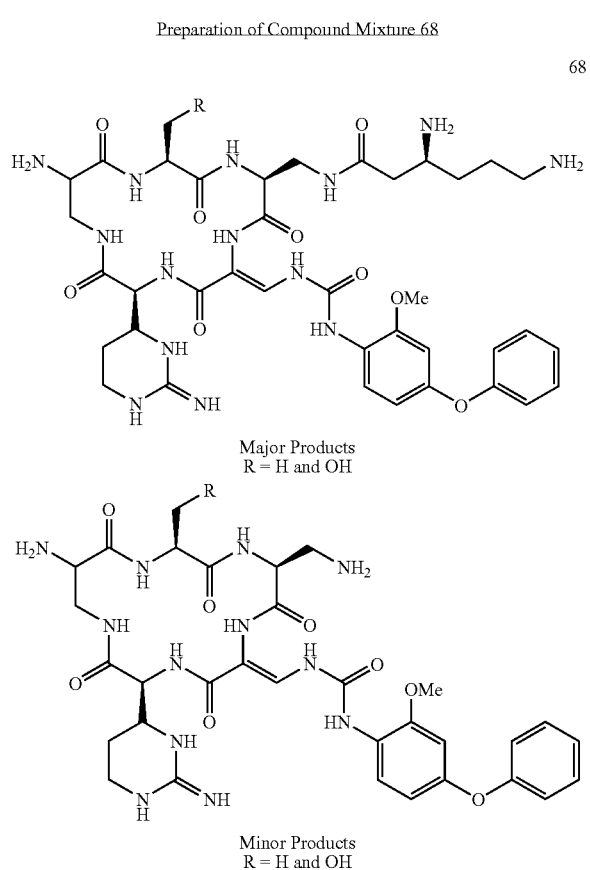

Compound mixture 68 was prepared as an HCl salt according to the procedure of Example 65, except that 1-fluoro-2-methyl-4-nitrobenzene was replaced with 4-chloro-2-methoxy-1-nitrobenzene (major products MH+=853.1, 867.3).

82

INDUSTRIAL APPLICABILITY

The compounds of the present subject matter are effective antibacterial agents and useful as medicaments for the treatment of microbial infections and for treating disorders caused by bacterial infections.

The foregoing description is considered as illustrative only of the principles of the present subject matter. Further, since numerous modifications and changes will be readily apparent to those skilled in the art, it is not desired to limit the present subject matter to the exact construction and process shown as described above. Accordingly, all suitable modifications and equivalents may be resorted to falling within the scope of the present subject matter as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound of the Formula

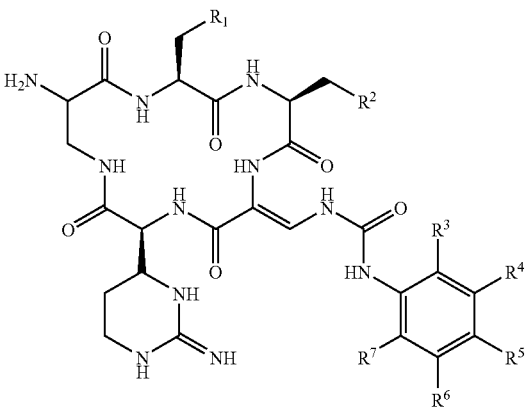

and solvates, metabolites, and pharmaceutically acceptable salts thereof, wherein:

$R^1$ is OH or H;

$R^2$ is $NH_2$ or

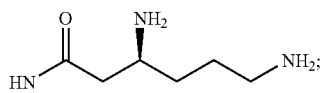

$R^3$, $R^4$, $R^5$, $R^6$ and $R^7$ are independently selected from aryl, heteroaryl, X-aryl, X-heteroaryl, hydrogen, halogen, cyano, nitro, trifluoromethyl, difluoromethyl, fluoromethyl, fluoromethoxy, difluoromethoxy, trifluoromethoxy, azido, —$OR^8$, $SR^8$, —$C(O)R^8$, —$C(O)OR^8$, $NR^9C(O)OR^{13}$, —$OC(O)R^8$, —$NR^9SO_2R^{13}$, —$SO_2NR^8R^9$, —$NR^9C(O)R^8$, —$C(O)NR^8R^9$, —$NR^{10}C(O)NR^8R^9$, —$NR^{10}C(NCN)NR^8R^9$, —$NR^8R^9$, alkyl, alkenyl, alkynyl, cycloalkyl, cycloalkylalkyl, —$S(O)_j(alkyl)$, —$S(O)_j(CR^{11}R^{12})_m$-aryl, arylalkyl, heteroarylalkyl, heterocyclyl, heterocyclylalkyl, —$O(CR^{11}R^{12})_n$-heterocyclyl or —$NR^9(CR^{11}R^{12})_n$-heterocyclyl, wherein at least one of $R^3$, $R^4$, $R^5$, $R^6$ and $R^7$ is aryl, heteroaryl, X-aryl or X-heteroaryl, and wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, oxime, halogen, cyano, nitro, fluoromethyl, difluoromethyl, trifluoromethyl, fluoromethoxy, difluoromethoxy, trifluoromethoxy, azido, alkyl, alkenyl, alkynyl, cycloalkyl, cycloalkylalkyl, —OR$^8$, —C=NOR$^8$, —C(O)R$^8$, —C(O)OR$^8$, —OC(O)R$^8$, —C(O)NR$^8$R$^9$, —NR$^8$R$^9$, —NR$^9$C(O)OR$^{13}$, —NR$^9$C(O)R$^8$, —NR$^{10}$C(O)NR$^8$R$^9$, —NR$^{10}$C(NCN)NR$^8$R$^9$, —O(CR$^{11}$R$^{12}$)$_n$-aryl, —NR$^9$(CR$^{11}$R$^{12}$)$_m$-aryl, —O(CR$^{11}$R$^{12}$)$_n$-heteroaryl, —NR$^9$(CR$^{11}$R$^{12}$)$_m$-heteroaryl, —O(CR$^{11}$R$^{12}$)$_n$-heterocyclyl, —NR$^9$(CR$^{11}$R$^{12}$)$_n$-heterocyclyl, —S(O)$_j$(alkyl), —S(O)$_j$(CR$^{11}$R$^{12}$)$_m$-aryl, —SO$_2$NR$^8$R$^9$, —NR$^9$SO$_2$R$^{13}$, aryl, heteroaryl, arylalkyl, heteroarylalkyl, heterocyclyl and heterocyclylalkyl;

X is O, O(CR$^{11}$R$^{12}$)$_n$, NR$^9$, (CR$^{11}$R$^{12}$)$_n$, CR$^{11}$=CR$^{12}$, or S(O)$_j$(CR$^{11}$R$^{12}$)$_m$, with the proviso that when R$^5$ is CH$_2$-phenyl, then R$^3$, R$^4$, R$^6$ and R$^7$ are not hydrogen;

R$^8$ is hydrogen, trifluoromethyl, alkyl, alkenyl, alkynyl, cycloalkyl, cycloalkylalkyl, aryl, arylalkyl, heteroaryl, heteroarylalkyl, heterocyclyl, heterocyclylalkyl, phosphate, or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted from oxo, halogen, cyano, nitro, trifluoromethyl, difluoromethoxy, trifluoromethoxy, azido, —NR'SO$_2$R'''', —SO$_2$NR'R'', —C(O)R', C(O)OR', —OC(O)R', —NR'C(O)OR'''', —NR'C(O)R'', —C(O)NR'R'', —SR', —S(O)R'''', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl;

R$^9$, R$^{10}$, R$^{11}$ and R$^{12}$ are independently hydrogen or alkyl, and

R$^{13}$ is trifluoromethyl, alkyl, cycloalkyl, aryl, arylalkyl, heteroaryl, heteroarylalkyl, heterocyclyl, heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR'SO$_2$R'''', —SO$_2$NR'R'', —C(O)R', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or R$^8$ and R$^9$ together with the atoms to which they are attached form a 4 to 10 membered saturated, partially unsaturated, or fully unsaturated heterocyclic ring, wherein said heterocyclic ring is optionally substituted with one or more groups independently selected from halogen, cyano, nitro, trifluoromethyl, difluoromethoxy, trifluoromethoxy, azido, —NR'SO$_2$R'''', —SO$_2$NR'R'', —C(O)R'''', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or R$^9$ and R$^{10}$ together with the atoms to which they are attached form a 4 to 10 membered saturated, partially unsaturated, or fully unsaturated heterocyclic ring, wherein said heterocyclic ring is optionally substituted with one or more groups independently selected from halogen, cyano, nitro, trifluoromethyl, difluoromethoxy, trifluoromethoxy, azido, —NR'SO$_2$R'''', —SO$_2$NR'R'', —C(O)R'''', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or R$^9$ and R$^{11}$ together with the atoms to which they are attached form a 4 to 10 membered saturated, partially unsaturated, or fully unsaturated heterocyclic ring, wherein said heterocyclic ring is optionally substituted with one or more groups independently selected from halogen, cyano, nitro, trifluoromethyl, difluoromethoxy, trifluoromethoxy, azido, —NR'SO$_2$R'''', —SO$_2$NR'R'', —C(O)R'''', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or R$^9$ and R$^{13}$ together with the atoms to which they are attached form a 4 to 10 membered saturated, partially unsaturated, or fully unsaturated heterocyclic ring, wherein said heterocyclic ring is optionally substituted with one or more groups independently selected from halogen, cyano, nitro, trifluoromethyl, difluoromethoxy, trifluoromethoxy, azido, —NR'SO$_2$R'''', —SO$_2$NR'R'', —C(O)R'''', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or R$^{11}$ and R$^{12}$ together with the atoms to which they are attached form a 4 to 10 membered saturated, partially unsaturated, or fully unsaturated carbocyclic ring, wherein said carbocyclic ring is optionally substituted with one or more groups independently selected from halogen, cyano, nitro, trifluoromethyl, difluoromethoxy, trifluoromethoxy, azido, —NR'SO$_2$R'''', —SO$_2$NR'R'', —C(O)R'''', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl;

R', R'' and R''' independently are hydrogen, alkyl, alkenyl, aryl and arylalkyl, and R'''' is alkyl, alkenyl, aryl and arylalkyl, or any two of R', R'', R''' or R'''' together with the atoms to which they are attached form a 4 to 10 membered carbocyclic, aryl, heteroaryl or heterocyclic ring, wherein any of said alkyl, alkenyl, and arylalkyl, and any of said carbocyclic, aryl, heteroaryl and heterocyclic rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

m is 0, 1, 2, 3, 4 or 5;

n is 1, 2, 3, 4 or 5; and j is 0, 1 or 2.

2. The compound of claim 1, wherein R¹ is H and R² is

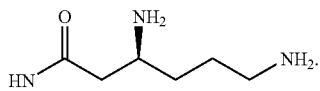

3. The compound of claim 1, wherein R¹ is OH and R² is

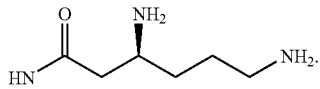

4. The compound of claim 1, wherein at least one of $R^3$, $R^4$, $R^5$, $R^6$ and $R^7$ is aryl or heteroaryl.

5. The compound of claim 4, wherein said aryl or heteroaryl is selected from phenyl, naphthyl, 2-pyridyl, 3-pyridyl, 4-pyridyl, 2-pyrimidyl, 4-pyrimidyl, 5-pyrimidyl, 1-isoquinolyl, 3-isoquinolyl, 4-isoquinolyl, 2-thienyl, 3-thienyl, 2-benzo[b]thienyl, 3-benzo[b]thienyl, 4-isoxazolyl, and substituted forms thereof.

6. The compound of claim 5, wherein R¹ is H and R² is

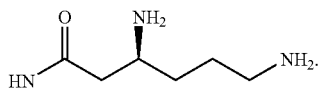

7. The compound of claim 5, wherein said aryl or heteroaryl is substituted with one or more groups independently selected from halogen, alkyl, and heteroalkyl.

8. The compound of claim 7, wherein said aryl or heteroaryl is substituted with one or more groups independently selected from F, Cl, $CF_3$, $CH_3$, $OCH_3$, and $OCF_3$.

9. The compound of claim 1, wherein at least one of $R^3$, $R^4$, $R^5$, $R^6$ and $R^7$ is X-aryl or X-heteroaryl.

10. The compound of claim 9, wherein said X-aryl is selected from O-phenyl, S-phenyl, $OCH_2$-phenyl, S—$CH_2$-phenyl, $CH_2$-phenyl, $CH_2CH_2$-phenyl, CH=CH-phenyl, $CH_2SO_2$-phenyl, NH-phenyl and substituted forms thereof.

11. The compound of claim 10, wherein R¹ is H and R² is

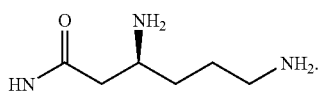

12. The compound of claim 10, wherein said X-aryl is substituted with one or more groups independently selected from halogen, alkyl, and heteroalkyl.

13. The compound of claim 12, wherein said X-aryl is substituted with one or more groups independently selected from F, Cl, $CF_3$, $CH_3$, $OCH_3$, and $OCF_3$.

14. The compound according to claim 1, wherein R¹ is H, R² is

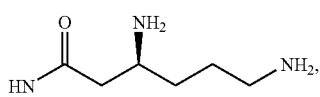

$R^3$, $R^5$, $R^6$ and $R^7$ are H, and $R^4$ is phenyl, 4-chlorophenyl, 4-trifluoromethylphenyl, 3-trifluoromethylphenyl, 4-toly, or 4-trifluoromethoxyphenyl.

15. The compound according to claim 1, wherein R¹ is H, R² is

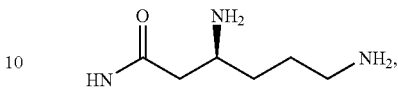

$R^3$, $R^5$, $R^6$ and $R^7$ are H, and $R^4$ is 1-naphthyl or 2-naphthyl.

16. The compound according to claim 1, wherein R¹ is H, R² is

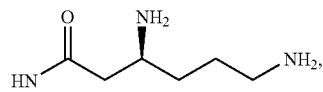

$R^3$, $R^5$, $R^6$ and $R^7$ are H, and $R^4$ is 2-pyridyl, 3-pyridyl, or 4-pyridyl.

17. The compound according to claim 1, wherein R¹ is H, R² is

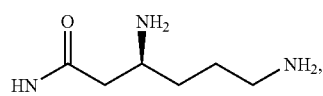

$R^3$, $R^5$, $R^6$ and $R^7$ are H, and $R^4$ is 5-pyrimidyl.

18. The compound according to claim 1, wherein R¹ is H, R² is

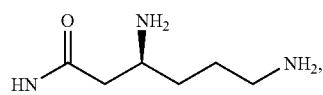

$R^3$, $R^5$, $R^6$ and $R^7$ are H, and $R^4$ is 4-isoquinolyl.

19. The compound according to claim 1, wherein R¹ is H, R² is

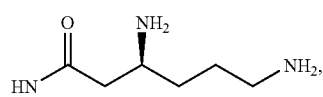

$R^3$, $R^5$, $R^6$ and $R^7$ are H, and $R^4$ is 2-thienyl, 3-thienyl, or 2-chloro-3-thienyl.

20. The compound according to claim 1, wherein R¹ is H, R² is

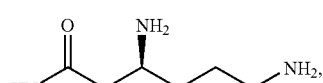

$R^3$, $R^5$, $R^6$ and $R^7$ are H, and $R^4$ is 3-benzo[b]thienyl or 2-benzo[b]thienyl.

21. The compound according to claim 1, wherein $R^1$ is H, $R^2$ is

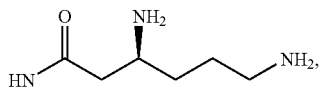

$R^3$, $R^5$, $R^6$ and $R^7$ are H, and $R^4$ is 3,5-dimethyl-4-isoxazolyl or phenoxy.

22. The compound according to claim 1, wherein $R^1$ is H, $R^2$ is

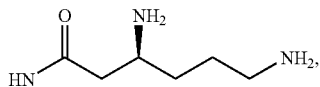

$R^3$, $R^4$, $R^6$ and $R^7$ are H, and $R^5$ is phenyl, 4-chlorophenyl, 4-trifluoromethylphenyl, or 3,5-ditrifluoromethylphenyl.

23. The compound according to claim 1, wherein $R^1$ is H, $R^2$ is

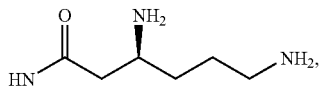

$R^3$, $R^4$, $R^6$ and $R^7$ are H, and $R^5$ is 1-naphthyl or 2-naphthyl.

24. The compound according to claim 1, wherein $R^1$ is H, $R^2$ is

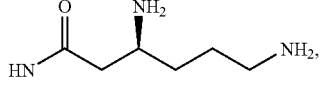

$R^3$, $R^4$, $R^6$ and $R^7$ are H, and $R^5$ is 2-pyridyl, 3-pyridyl, or 4-pyridyl.

25. The compound according to claim 1, wherein $R^1$ is H, $R^2$ is

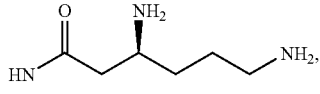

$R^3$, $R^4$, $R^6$ and $R^7$ are H, and $R^5$ is 2-thienyl.

26. The compound according to claim 1, wherein $R^1$ is H, $R^2$ is

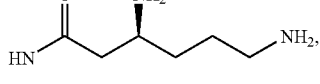

$R^3$, $R^4$, $R^6$ and $R^7$ are H, and $R^5$ is phenoxy, 4-chlorophenyoxy or 4-methylphenoxy.

27. The compound according to claim 1, wherein $R^1$ is H, $R^2$ is

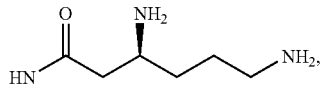

$R^3$, $R^4$, $R^6$ and $R^7$ are H, and $R^5$ is 3,5-difluoromethylphenyl.

28. The compound according to claim 1, wherein $R^1$ is H, $R^2$ is

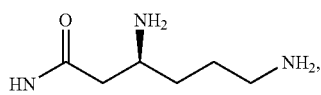

$R^3$, $R^4$, $R^6$ and $R^7$ are H, and $R^5$ is 4-fluorophenoxy, 4-trifluoromethylphenoxy, or 3-trifluoromethylphenoxy.

29. The compound according to claim 1, wherein $R^1$ is H, $R^2$ is

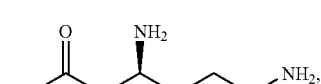

$R^3$, $R^4$, $R^6$ and $R^7$ are H, and $R^5$ is benzenethiolate or 4-methylbenzenethiolate.

30. The compound according to claim 1, wherein $R^1$ is H, $R^2$ is

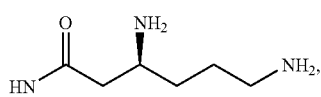

$R^3$, $R^4$, $R^6$ and $R^7$ are H, and $R^5$ is $CH_2$=CHPh or $CH_2CH_2Ph$.

31. The compound according to claim 1, wherein $R^1$ is H, $R^2$ is

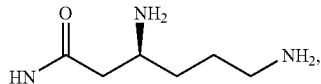

$R^3$, $R^4$, $R^6$ and $R^7$ are H, and $R^5$ is $CH_2SO_2Ph$, NHPh, $OCH_2Ph$ or $SCH_2Ph$.

32. The compound according to claim 1, wherein $R^1$ is H, $R^2$ is

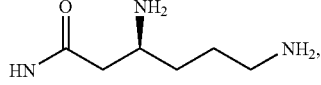

$R^4$, $R^5$, $R^6$ and $R^7$ are H, and $R^3$ is selected from phenyl, 4-chlorophenyl and phenoxy.

33. A composition comprising one or more compounds of claim 1.

34. The composition of claim 33, wherein $R^3$ is aryl, heteroaryl, X-aryl or X-heteroaryl, and $R^4$, $R^5$, $R^6$ and $R^7$ are H.

35. The composition of claim 33, wherein $R^4$ is aryl, heteroaryl, X-aryl or X-heteroaryl, and $R^3$, $R^5$, $R^6$ and $R^7$ are H.

36. The composition of claim 33, wherein $R^5$ is aryl, heteroaryl, X-heteroaryl, $CH_2SO_2Ph$, NHPh, $OCH_2Ph$ or $CH_2SPh$, and $R^3$, $R^4$, $R^6$ and $R^7$ are H.

37. A compound of claim 1, prepared by the method comprising reacting capreomycin sulfate with a reagent having the formula

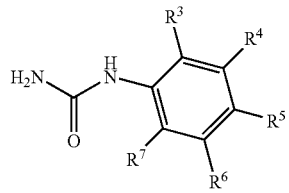

in the presence of an acid, wherein said capreomycin is a mixture of capreomycin IA, capreomycin IB, capreomycin IIA, and capreomycin IIB.

38. The compound of claim 1, prepared by the method comprising reacting capreomycin IB with a reagent having the formula

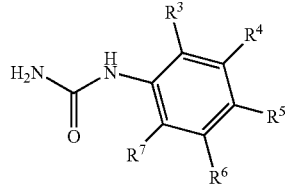

in the presence of an acid.

39. The compound of claim 9, wherein said X-heteroaryl is selected from O-pyridinyl, O-pyrimidinyl, O-pyridazinyl, S-pyridinyl, S-pyrimidinyl, S-pyridazinyl, NH-pyridinyl, NH-pyrimidinyl, and NH-pyridazinyl.

40. The compound according to claim 1, wherein $R^1$ is H, $R^2$ is

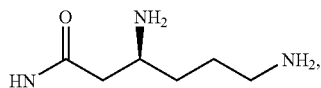

$R^3$, $R^5$, $R^6$ and $R^7$ are H, and $R^4$ is 5-chlorothien-2-yl, 1-phenylmethyl, 4-methylphenoxy, 4-fluorophenoxy, 4-chlorophenoxy, naphthylene-2yloxy, 3-methylphenoxy, 3-flurophenoxy, 3,4-dichlorophenoxy, 3,4-difluorophenoxy, 4-isopropylphenoxy or 3,4-dimethylphenoxy.

41. The compound according to claim 1, wherein $R^1$ is H, $R^2$ is

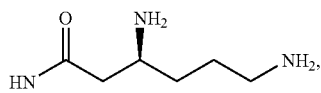

$R^3$, $R^4$, $R^6$ and $R^7$ are H, and $R^5$ is 3,5-bis-trifluoromethylphenoxy, 3-methoxyphenoxy or phenylthiomethyl.

42. The compound according to claim 1, wherein $R^1$ is H, $R^2$ is

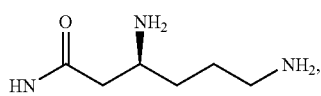

$R^4$, $R^5$, and $R^7$ are H, $R^3$ is methyl, and $R^6$ is phenyl.

43. The compound according to claim 1, wherein $R^1$ is H, $R^2$ is

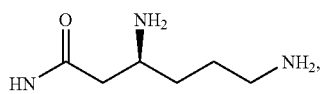

$R^3$, $R^6$ and $R^7$ are H, $R^5$ is 4-chlorophenoxy, and $R^4$ is Cl, F, Me or OMe.

44. The compound according to claim 1, wherein $R^1$ is H, $R^2$ is

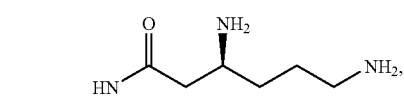

$R^4$, $R^6$ and $R^7$ are H, $R^5$ is phenoxy, and $R^3$ is Me or OMe.

* * * * *

UNITED STATES PATENT AND TRADEMARK OFFICE
CERTIFICATE OF CORRECTION

PATENT NO.        : 7,294,616 B2
APPLICATION NO. : 11/261717
DATED             : November 13, 2007
INVENTOR(S)       : Joseph P. Lyssikatos and Steven M. Wenglowsky It is certified that error appears in the above-identified patent and that said Letters Patent is hereby corrected as shown below:

In column 85, line 41 and 42, claim 10, delete "S-$CH_2$-phenyl" and insert --$CH_2$S-phenyl--.

Signed and Sealed this

Twelfth Day of August, 2008

JON W. DUDAS
*Director of the United States Patent and Trademark Office*